US010696677B2

(12) United States Patent
Maitra et al.

(10) Patent No.: US 10,696,677 B2
(45) **Date of Patent: *Jun. 30, 2020**

(54) DIARYL PURINE DERIVATIVES WITH IMPROVED BIOAVAILABILITY

(71) Applicant: Research Triangle Institute, Research Triangle Park, NC (US)

(72) Inventors: Rangan Maitra, Cary, NC (US); Robert W. Wiethe, Durham, NC (US); Yanan Zhang, Apex, NC (US); George S. Amato, Cary, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/472,155

(22) PCT Filed: Dec. 20, 2017

(86) PCT No.: PCT/US2017/067602

§ 371 (c)(1),
(2) Date: Jun. 20, 2019

(87) PCT Pub. No.: WO2018/119076

PCT Pub. Date: Jun. 28, 2018

(65) Prior Publication Data

US 2019/0352305 A1 Nov. 21, 2019

Related U.S. Application Data

(60) Provisional application No. 62/437,280, filed on Dec. 21, 2016.

(51) Int. Cl.

| | |
|---|---|
| ***C07D 473/34*** | (2006.01) |
| ***C07D 471/10*** | (2006.01) |
| ***A61K 31/52*** | (2006.01) |
| ***A61P 1/16*** | (2006.01) |

(52) U.S. Cl.

CPC ............ *C07D 473/34* (2013.01); *A61K 31/52* (2013.01); *A61P 1/16* (2018.01); *C07D 471/10* (2013.01)

(58) Field of Classification Search

CPC .... C07D 401/04; C07D 473/32; A61K 31/52; A61P 1/16

USPC .......................... 544/276; 514/263.22, 263.4

See application file for complete search history.

(56) References Cited

U.S. PATENT DOCUMENTS

| | | | | |
|---|---|---|---|---|
| 7,129,239 | B2 | 10/2006 | Griffith | |
| 8,252,791 | B2 | 8/2012 | McElroy et al. | |
| 9,133,128 | B2 | 9/2015 | Fulp et al. | |
| 9,187,480 | B2 | 11/2015 | Maitra et al. | |
| 9,458,160 | B2 * | 10/2016 | Maitra | C07D 473/34 |
| 2008/0287505 | A1 | 11/2008 | McElroy et al. | |
| 2015/0031689 | A1 * | 1/2015 | Maitra | C07D 473/34 514/228.5 |
| 2016/0046630 | A1 | 2/2016 | Maitra et al. | |

FOREIGN PATENT DOCUMENTS

| | | | |
|---|---|---|---|
| WO | 2004037823 | A1 | 5/2004 |
| WO | 2010019762 | A1 | 2/2010 |
| WO | 2012174362 | A1 | 12/2012 |
| WO | 2013123335 | A1 | 8/2013 |

OTHER PUBLICATIONS

Mallat et al. J Hepatol. Oct. 2013;59(4):891-6.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Chorvat, Robert J. 2013. "Peripherally Restricted CB1 receptor blockers." Bioorganic & Medicinal Chemistry Letters. vol. 23, 4751-4760.
Chorvat, Robert J. et al. 2012. "JD-5006 and JD-5037: Peripherally restricted (PR) cannabinoid-1 receptor blockers related to SLV-319 (Ibipinabant) as metabolic disorder therapeutics devoid of CNS liabilities". Bioorganic & Medicinal Chemistry Letters. vol. 22, 6173-6180.
Fulp, Alan et al. 2012. "Diphenyl Purine Derivatives as Peripherally Selective Cannabinoid Receptor 1 Antagonists". J. Med. Chem. vol. 55, 10022-10032.
International Search report and Written Opinion issued in counterpart PCT Application No. PCT/US2017/067602 dated May 15, 2018.
Kuang, Guanglin et al. 2012. "In silico investigation of interactions between human cannabinoid receptor-1 and its antagonists." J. Mol. Model. vol. 18, 3831-3845.
Otenabant. Wikipedia. Accessed Jul. 20, 2015 (five (5) pages).
International Preliminary Report on Patentability issued in counterpart PCT Application No. PCT/US2017/067602 dated Jun. 25, 2019 (nine (9) pages).

* cited by examiner

*Primary Examiner* — Venkataraman Balasubramanian
(74) *Attorney, Agent, or Firm* — Nathan P. Letts; Olive Law Group, PLLC

(57) ABSTRACT

This disclosure is directed to various compounds and methods of preparation of improved compounds that are capable of functioning as cannabinoid receptor 1 (CB1) antagonists with reduced central nervous system (CNS) side effects. The application is also directed to pharmaceutical compositions containing one or more of these compounds, which may also contain one or more additional therapeutic agents. It is also directed to methods of treatment of various conditions that may be responsive to antagonism of the CB1 receptors, including, but not limited to, metabolic syndromes (including liver disease, obesity, and diabetes).

20 Claims, 1 Drawing Sheet

DIARYL PURINE DERIVATIVES WITH IMPROVED BIOAVAILABILITY

CROSS REFERENCE TO RELATED APPLICATIONS

Figure 1A:
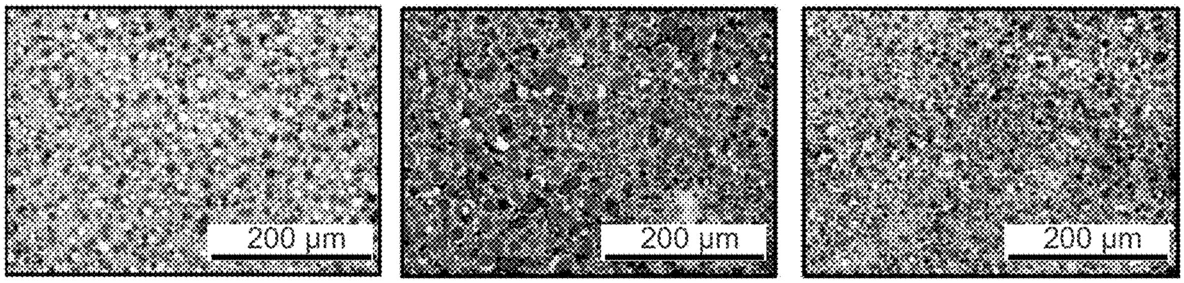

This application claims the benefit of U.S. Provisional Appn. 62/437,280 filed Dec. 21, 2016, Maitra et al., entitled "DIARYL PURINE DERIVATIVES WITH IMPROVED BIOAVAILABILITY", which is hereby incorporated by reference in its entirety.

STATEMENT REGARDING FEDERALLY SPONSORED RESEARCH OR DEVELOPMENT

This application is a § 371 U.S. National Stage of International Application PCT/US2017/067602, filed Dec. 20, 2017, which claims the benefit of U.S. Provisional Appn. 62/437,280 filed Dec. 21, 2016, Maitra et al., entitled "DIARYL PURINE DERIVATIVES WITH IMPROVED BIOAVAILABILITY", which is hereby incorporated by reference in their entireties.

1. FIELD

The present disclosure provides various compounds and methods of preparation of improved compounds that are capable of functioning as cannabinoid receptor 1 (CB1) antagonists with reduced central nervous system (CNS) side effects. The application is also directed to pharmaceutical compositions containing one or more of these compounds, which may also contain one or more additional therapeutic agents. It is also directed to methods of treatment of various conditions that may be responsive to antagonism of the CB1 receptors, including, but not limited to, metabolic syndromes (including liver disease, obesity, and diabetes).

2. BACKGROUND

2.1. Introduction

Cannabinoid receptors (CBRs) belong to the endocannabinoid (EC) system, which consists of receptors, transporters, endocannabinoids, and enzymes involved in synthesis and degradation of endocannabinoids. The EC system regulates many important physiological processes and several components of the EC system are under evaluation as targets to treat a diverse array of indications including obesity, liver disease, diabetes, pain and inflammation. To date, two different cannabinoid receptors have been identified (referred to as CB1 and CB2). CB1 and CB2 receptors fall within the class of G protein-coupled receptors, and primarily function to activate inhibitory G proteins (Gi/o).

The CB1 receptor is prominently expressed in the central nervous system (CNS) and also in peripheral tissues. Accordingly, drugs targeting the CB1 receptors have been developed over the years to treat various metabolic disorders including obesity and diabetes. The first drug selective for CB1 that was developed for medical use was rimonabant, an inverse agonist/antagonist. Rimonabant was designed to treat obesity and other related disorders that have both CNS and peripheral components. Although rimonabant has demonstrated clinical efficacy in clinical trials, it was withdrawn from European markets and denied FDA approval in the United States due to CNS-related side effects including anxiety, depression and suicidal ideation. The development of other related compounds (e.g., taranabant, otenabant, and ibipinabant) was discontinued based on these noted side effects. Accordingly, it would be beneficial to provide CB1 antagonists that are effective, but that do not result in such CNS-related side effects.

Literature examples of CB1 antagonists may be found in U.S. Pat. Nos. 8,252,791 (McElroy & Chorvat), 7,129,239 (Griffith); PCT Pub. Nos. WO 2013/123335 (Maitra et al.), WO 2012/174362 (Fulp et al.); Chorvat et al. 2013 *Bioorg Med Chem Lt* 23 4751-4760, Chorvat et al. 2012 *Bioorg Med Chem Lt* 22 6173-6180, Fulp et al. 2012 *J Med Chem* 55 10022-10032. The contents of which are hereby incorporated by reference in their entireties.

3. SUMMARY OF THE DISCLOSURE

In embodiment 1, this disclosure is directed to a compound represented by the Formula I:

I

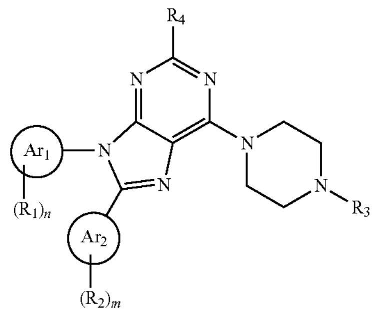

or a pharmaceutically acceptable salt, a prodrug, or a salt of a prodrug, wherein each $Ar_1$ and $Ar_2$ is independently aryl or heteroaryl; each $R_1$ and $R_2$ is independently $C_{1-8}$ alkoxy, $C_{1-8}$ alkyl, $C_{3-8}$ cycloalkyl, $C_{3-6}$ heterocycle, —$CONR_5R_6$, —$COR_7$, cyano, H, halo, —$NR_5R_6$, —$NR_8COR_7$, —$NR_8CONR_5R_6$, —$NR_8SO_2R_7$, —$NR_8SO_2NR_5R_6$, —$SO_2NR_5R_6$ or —$SO_2R_7$; $R_3$ is aryl, $C_{1-8}$ alkyl(aryl), $C_{1-8}$ alkyl(heterocycle), $C_{1-8}$ alkyl(heterocycle), $C_{2-8}$ alkenyl, $C_{1-8}$ alkyl, $C_{3-8}$ alkynyl, $C_{3-8}$ cycloalkyl, —C(=$NR_9$)$NR_{10}R_{11}$, —C(=$NR_9$)$R_{12}$, —$CONR_{10}R_{11}$, —CON($R_{11}$)$SO_2R_{12}$, —$COR_{12}$, —$CO_2R_{12}$, heteroaryl, heterocycle, —$SO_2NR_{10}R_{11}$ or —$SO_2R_{12}$; $R_4$ is independently $C_{1-8}$ alkoxy, $C_{1-8}$ alkyl, $C_{3-8}$ cycloalkyl, or H; each $R_5$, $R_6$, $R_8$ $R_{10}$ and $R_{11}$ is independently aryl, $C_{1-8}$ alkyl, $C_{1-8}$ alkyl(aryl), $C_{1-8}$ alkyl(heteroaryl), $C_{1-8}$ alkyl(heterocycle), $C_{1-8}$ alkyl ($C_{3-8}$ cycloalkyl), $C_{3-8}$ cycloalkyl, H, heteroaryl or heterocycle; or $R_5$ and $R_6$ together make a 3-8 member ring which may be substituted with one or more heteroatoms; or $R_5$ and $R_8$ together make a 4-8 member ring which may be substituted with one or more heteroatoms; or $R_{10}$ and $R_{11}$ together make a 3-8 member ring which may be substituted with one or more heteroatoms; each $R_7$ and $R_{12}$ is independently aryl, $C_{1-8}$ alkyl, $C_{1-8}$ alkyl(aryl), $C_{1-8}$ alkyl(heteroaryl), $C_{1-8}$ alkyl (heterocycle), $C_{1-8}$ alkyl($C_{3-8}$ cycloalkyl), $C_{3-8}$ cycloalkyl, heteroaryl or heterocycle; or $R_7$ and $R_8$ together make a 4-8 member ring which may be substituted with one or more heteroatoms; or $R_{11}$ and $R_{12}$ together make a 4-8 member ring which may be substituted with one or more heteroatoms; $R_9$ is $C_{1-8}$ alkoxy, $C_{1-8}$ alkyl, $C_{3-8}$ cycloalkyl, cyano, H, or hydroxy; and wherein n and m are independently integers from 0 to 5.

In embodiment 2, the compound of Formula I wherein $R_4$ is H.

In embodiment 3, the compound of Formula I or embodiments 1-2, wherein $Ar_1$ is phenyl or a 6-membered heteroaryl ring.

In embodiment 4, the compound of Formula I or any of embodiments 1-3, wherein $Ar_1$ is meta and/or para substituted.

In embodiment 5, the compound of Formula I or any of embodiments 1-4, wherein $Ar_2$ is phenyl or a 6-membered heteroaryl ring.

In embodiment 6, the compound of Formula I or any of embodiments 1-5, wherein $Ar_2$ is ortho substituted.

In embodiment 7, the compound of Formula I or any of embodiments 1-6, wherein $R_1$ is F, Cl, $CF_3$, CN, $OCF_3$ or $OCHF_2$.

In embodiment 8, the compound of Formula I or any of embodiments 1-7, wherein $R_2$ is F, Cl, $CF_3$ or Me.

In embodiment 9, the compound of Formula I or any of embodiments 1-8, wherein $R_3$ is $C_{1-8}$ alkyl(aryl) or $C_{1-8}$ alkyl(heteroaryl).

In embodiment 10, the compound of Formula I or any of embodiments 1-8, wherein $R_3$ is —$CONR_{10}R_{11}$.

In embodiment 11, the compound of Formula I or any of embodiments 1-8, 10, wherein $R_{10}$ is aryl, heteroaryl, $C_{1-8}$ alkyl, $C_{3-8}$ cycloalkyl, or $C_{1-6}$ alkyl($C_{3-8}$ cycloalkyl).

In embodiment 12, the compound of Formula I or any of embodiments 1-8, 10, 11, wherein $R_{11}$ is H.

In embodiment 13, the compound of Formula I or any of embodiments 1-12 wherein n and m are independently 1 or 2.

In embodiment 14, the compound of Formula I or any of embodiments 1-12 wherein both n and m are 1.

In embodiment 15, the compound of Formula I or any of embodiments 1-14, having structures 3, 6, 42-53, 56-89, 94-123 shown in Table 2.

In embodiment 16, the disclosure also provides a compound represented by the Formula II:

II

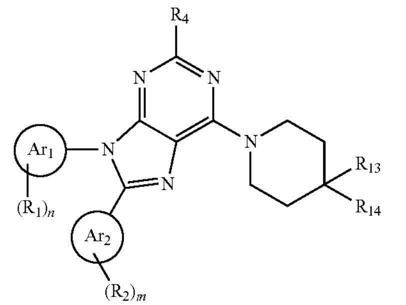

or a pharmaceutically acceptable salt, a prodrug, or a salt of a prodrug, wherein both $Ar_1$ and $Ar_2$ is heteroaryl or $Ar_1$ is heteroaryl and $Ar_2$ is aryl or $Ar_1$ is aryl and $Ar_2$ is heteroaryl; each $R_1$ and $R_2$ is independently $C_{1-8}$ alkoxy, $C_{1-8}$ alkyl, $C_{3-8}$ cycloalkyl, $C_{3-6}$ heterocycle, —$CONR_5R_6$, —$COR_7$, cyano, H, halo, —$NR_5R_6$, —$NR_8COR_7$, —$NR_8CONR_5R_6$, —$NR_8SO_2R_7$, —$NR_8SO_2NR_5R_6$, —$SO_2NR_5R_6$ or —$SO_2R_7$; $R_4$ is $C_{1-8}$ alkoxy, $C_{1-8}$ alkyl, $C_{3-8}$ cycloalkyl, or H; $R_{13}$ is —C(=$NR_9$)$R_{12}$, —C(=$NR_9$)$NR_{10}R_{11}$, heteroaryl, $NHR_{15}$ or $NR_{15}R_{19}$; $R_{14}$ is aryl, $C_{1-8}$ alkyl, $C_{3-8}$ cycloalkyl, $C_{3-6}$ heterocycle, heteroaryl or H; or $R_{13}$ and $R_{14}$ together make a 3-8 member ring which may be substituted with one or more heteroatoms; $R_{15}$ is aryl, $C_{1-8}$ alkyl(aryl), $C_{1-8}$ alkyl(heteroaryl), $C_{1-8}$ alkyl(heterocycle), $C_{2-8}$ alkenyl, $C_{2-8}$ alkyl, $C_{3-8}$ alkynyl, $C_{3-8}$ cycloalkyl, —C(=$NR_9$)$NR_{10}R_{11}$, —C(=$NR_9$)$R_{12}$, —$CONR_{10}R_{11}$, —CON($R_{11}$)$SO_2R_{12}$, —$COR_{12}$, —$CO_2R_{12}$, heteroaryl, heterocycle, —$SO_2NR_{10}R_{11}$ or —$SO_2R_{12}$; each $R_5$, $R_6$, $R_8$, $R_{10}$, $R_{11}$, and $R_{19}$ is independently aryl, $C_{1-8}$ alkyl, $C_{1-8}$ alkyl(aryl), $C_{1-8}$ alkyl(heteroaryl), $C_{1-8}$ alkyl(heterocycle), $C_{1-8}$ alkyl($C_{3-8}$ cycloalkyl), $C_{3-8}$ cycloalkyl, H, heteroaryl or heterocycle; or $R_5$ and $R_6$ together make a 3-8 member ring which may be substituted with one or more heteroatoms; or $R_5$ and $R_8$ together make a 4-8 member ring which may be substituted with one or more heteroatoms; or $R_{10}$ and $R_{11}$ together make a 3-8 member ring which may be substituted with one or more heteroatoms; each $R_7$ and $R_{12}$ is independently aryl, $C_{1-8}$ alkyl, $C_{1-8}$ alkyl(aryl), $C_{1-8}$ alkyl(heteroaryl), $C_{1-8}$ alkyl (heterocycle), $C_{1-8}$ alkyl($C_{3-8}$ cycloalkyl), $C_{3-8}$ cycloalkyl, heteroaryl or heterocycle; or $R_7$ and $R_8$ together make a 4-8 member ring which may be substituted with one or more heteroatoms; or $R_{11}$ and $R_{12}$ together make a 4-8 member ring which may be substituted with one or more heteroatoms; $R_9$ is $C_{1-8}$ alkoxy, $C_{1-8}$ alkyl, $C_{3-8}$ cycloalkyl, cyano, H, or hydroxy; and wherein n and m are independently integers from 0 to 5.

In embodiment 17, the disclosure provides the compound of Formula II wherein $R_4$ is H.

In embodiment 18, the disclosure provides the compound of Formula II or any of embodiments 16-17, wherein $Ar_1$ is phenyl or a 6-membered heteroaryl ring.

In embodiment 19, the disclosure provides the compound of Formula II or any of embodiments 16-18, wherein $Ar_1$ is meta or para substituted.

In embodiment 20, the disclosure provides the compound of Formula II or any of embodiments 16-19, wherein $Ar_2$ is phenyl or a 6-membered heteroaryl ring.

In embodiment 21, the disclosure provides the compound of Formula II or any of embodiments 16-20, wherein $Ar_2$ is ortho substituted.

In embodiment 22, the disclosure provides the compound of Formula II or any of embodiments 16-21, wherein $R_1$ is F, Cl, $CF_3$, CN, $OCF_3$ or $OCHF_2$.

In embodiment 23, the disclosure provides the compound of Formula II or any of embodiments 16-22, wherein $R_2$ is F, Cl, $CF_3$ or Me.

In embodiment 24, the disclosure provides the compound of Formula II or any of embodiments 16-23, wherein $R_{13}$ is $NHR_{15}$ or $NR_{15}R_{19}$.

In embodiment 25, the disclosure provides the compound of Formula II or any of embodiments 16-24, wherein $R_{15}$ is —$COR_{12}$, —$CO_2R_{12}$ or —$SO_2R_{12}$.

In embodiment 26, the disclosure provides the compound of Formula II or any of embodiments 16-24, wherein $R_{15}$ is —$CONR_{10}R_{11}$.

In embodiment 27, the disclosure provides the compound of Formula II or any of embodiments 16-24, wherein $R_{15}$ is —C(=$NR_9$)$NR_{10}R_{11}$ or —C(=$NR_9$)$R_{12}$.

In embodiment 28, the disclosure provides the compound of Formula II or any of embodiments 16-27, wherein $R_{10}$ is aryl, heteroaryl, $C_{1-8}$ alkyl, $C_{3-8}$ cycloalkyl, or $C_{1-6}$ alkyl ($C_{3-8}$ cycloalkyl).

In embodiment 29, the disclosure provides the compound of Formula II or any of embodiments 16-28, wherein $R_{11}$ is H.

In embodiment 30, the disclosure provides the compound of Formula II or any of embodiments 16-29, wherein $R_{14}$ is H.

In embodiment 31, the disclosure provides the compound of Formula II or any of embodiments 16-30, wherein n and m are independently 1 or 2.

In embodiment 32, the disclosure provides the compound of Formula II or any of embodiments 16-30, wherein both n and m are 1.

In embodiment 33, the disclosure provides the compound of Formula II or any of embodiments 16-32, having structures 8, 10-17, 20, 21, 34, 35, 54, 55, 90-93 shown in Table 2.

In embodiment 34, the disclosure also provides a compound represented by the Formula III:

III

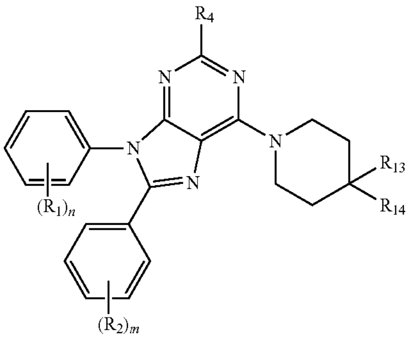

or a pharmaceutically acceptable salt, a prodrug, or a salt of a prodrug, wherein each $R_1$ and $R_2$ is independently $C_{1-8}$ alkoxy, $C_{1-8}$ alkyl, $C_{3-8}$ cycloalkyl, $C_{3-6}$ heterocycle, —$CONR_5R_6$, —$COR_7$, cyano, H, halo, —$NR_5R_6$, —$NR_8COR_7$, —$NR_8CONR_5R_6$, —$NR_8SO_2R_7$, —$NR_8SO_2NR_5R_6$, —$SO_2NR_5R_6$ or —$SO_2R_7$; $R_4$ is $C_{1-8}$ alkoxy, $C_{1-8}$ alkyl, $C_{3-8}$ cycloalkyl, or H; $R_{13}$ is —C(═$NR_9$)$R_{12}$, —C(═$NR_9$)$NR_{10}R_{11}$, heteroaryl, $NHR_{15}$ or $NR_{15}R_{19}$; $R_{14}$ is aryl, $C_{1-8}$ alkyl, $C_{3-8}$ cycloalkyl, $C_{3-6}$ heterocycle, heteroaryl or H; or $R_{13}$ and $R_{14}$ together make a 3-8 member ring which may be substituted with one or more heteroatoms; $R_{15}$ is aryl, $C_{1-8}$ alkyl(aryl), $C_{1-8}$ alkyl(heteroaryl), $C_{1-8}$ alkyl(heterocycle), $C_{2-8}$ alkenyl, $C_{2-8}$ alkyl, $C_{3-8}$ alkynyl, $C_{3-8}$ cycloalkyl, —C(═$NR_9$)$NR_{10}R_{11}$, —C(═$NR_9$)$R_{12}$, —$CONR_{16}R_{11}$, —CON($R_{11}$)$SO_2R_{12}$, —$COR_{17}$, heteroaryl, heterocycle, —$SO_2NR_{16}R_{11}$ or —$SO_2R_{18}$; each $R_5$, $R_6$, $R_8$, $R_{10}$, $R_{11}$, and $R_{19}$ is independently aryl, $C_{1-8}$ alkyl, $C_{1-8}$ alkyl(aryl), $C_{1-8}$ alkyl(heteroaryl), $C_{1-8}$ alkyl(heterocycle), $C_{1-8}$ alkyl($C_{3-8}$ cycloalkyl), $C_{3-8}$ cycloalkyl, H, heteroaryl or heterocycle; or $R_5$ and $R_6$ together make a 3-8 member ring which may be substituted with one or more heteroatoms; or $R_5$ and $R_8$ together make a 4-8 member ring which may be substituted with one or more heteroatoms; or $R_{10}$ and $R_{11}$ together make a 3-8 member ring which may be substituted with one or more heteroatoms; or $R_{11}$ and $R_{16}$ together make a 3-8 member ring which may be substituted with one or more heteroatoms; each $R_7$ and $R_{12}$ is independently aryl, $C_{1-8}$ alkyl, $C_{1-8}$ alkyl(aryl), $C_{1-8}$ alkyl(heteroaryl), $C_{1-8}$ alkyl(heterocycle), $C_{1-8}$ alkyl($C_{3-8}$ cycloalkyl), $C_{3-8}$ cycloalkyl, heteroaryl or heterocycle; or $R_7$ and $R_8$ together make a 4-8 member ring which may be substituted with one or more heteroatoms; or $R_{11}$ and $R_{12}$ together make a 4-8 member ring which may be substituted with one or more heteroatoms; $R_9$ is $C_{1-8}$ alkoxy, $C_{1-8}$ alkyl, $C_{3-8}$ cycloalkyl, cyano, H, or hydroxyl; $R_{16}$ and $R_{18}$ is independently aryl, $C_{1-8}$ alkyl(aryl), $C_{1-8}$ alkyl(heteroaryl), $C_{1-8}$ alkyl(heterocycle), heteroaryl or heterocycle; $R_{17}$ is $C_{1-8}$ alkyl(heteroaryl), $C_{1-8}$ alkyl(heterocycle), heteroaryl or heterocycle; and wherein n and m are independently integers from 0 to 5.

In embodiment 35, the disclosure provides the compound of Formula III or embodiment 34 wherein $R_4$ is H.

In embodiment 36, the disclosure provides the compound of Formula III or any of embodiments 34-35, wherein $R_1$ is at the meta and/or para positions.

In embodiment 37, the disclosure provides the compound of Formula III or any of embodiments 34-36, wherein at least one $R_2$ is in the ortho position.

In embodiment 38, the disclosure provides the compound of Formula III or any of embodiments 34-37, wherein $R_1$ is F, Cl, $CF_3$, CN, $OCF_3$ or $OCHF_2$.

In embodiment 39, the disclosure provides the compound of Formula III or any of embodiments 34-38, wherein $R_2$ is F, Cl, $CF_3$ or Me.

In embodiment 40, the disclosure provides the compound of Formula III or any of embodiments 34-39, wherein $R_{13}$ is $NHR_{15}$ or $NR_{15}R_{19}$.

In embodiment 41, the disclosure provides the compound of Formula III or any of embodiments 34-40, wherein $R_{15}$ is —$CONR_{16}R_{11}$.

In embodiment 42, the disclosure provides the compound of Formula III or any of embodiments 34-40, wherein $R_{15}$ is —$COR_{17}$ or —$SO_2R_{18}$.

In embodiment 43, the disclosure provides the compound of Formula III or any of embodiments 34-40, wherein $R_{15}$ is —C(═$NR_9$)$NR_{10}R_{11}$ or —C(═$NR_9$)$R_{12}$.

In embodiment 44, the disclosure provides the compound of Formula III or any of embodiments 34-43, wherein $R_{10}$ is aryl, heteroaryl, $C_{1-8}$ alkyl, $C_{3-8}$ cycloalkyl, or $C_{1-6}$ alkyl ($C_{3-8}$ cycloalkyl).

In embodiment 45, the disclosure provides the compound of Formula III or any of embodiments 34-44, wherein $R_{11}$ is H.

In embodiment 46, the disclosure provides the compound of Formula III or any of embodiments 34-45, wherein $R_{14}$ is H.

In embodiment 47, the disclosure provides the compound of Formula III or any of embodiments 34-41, 44-45 wherein $R_{16}$ is aryl, $C_{1-8}$ alkyl(aryl), $C_{1-8}$ alkyl(heteroaryl) or heteroaryl.

In embodiment 48, the disclosure provides the compound of Formula III or any of embodiments 34-40, 42, 44-46 wherein $R_{17}$ is $C_{1-8}$ alkyl(heteroaryl) or heteroaryl.

In embodiment 49, the disclosure provides the compound of Formula III or any of embodiments 34-40, 42, 44-46, wherein $R_{18}$ is aryl, $C_{1-8}$ alkyl(aryl), $C_{1-8}$ alkyl(heteroaryl) or heteroaryl.

In embodiment 50, the disclosure provides the compound of Formula III or any of embodiments 34-49, wherein n and m are independently 1 or 2.

In embodiment 51, the disclosure provides the compound of Formula III or any of embodiments 34-49, wherein both n and m are 1.

In embodiment 52, the disclosure provides the compound of Formula III or any of embodiments 34-51, having structures 1, 2, 4, 5, 7, 9, 18, 19, 22-33, 36-41, 124-129 shown in Table 2.

In embodiment 53, the disclosure provides a pharmaceutical composition, comprising a compound of any of embodiments 1-52 and one or more pharmaceutically acceptable carriers.

In embodiment 54, the disclosure provides a method for treating or delaying the progression of disorders that are alleviated by antagonizing the CB1 receptor, the method comprising administering a compound of any of embodiments 1-53.

In embodiment 55, the disclosure provides the method of embodiment 54, wherein the disorder is diabetes, dyslipidemia, inflammation, liver diseases, obesity, or pain. The liver disease may be a fatty liver disease such as alcoholic steatosis or nonalcoholic steatohepatitis (NASH).

In embodiment 56, the disclosure provides the method of any of embodiments 54-55, wherein the compound is formulated or co-administered with a second agent wherein the second agent is an anti-depressant, a blood pressure lowering agent, or a lipid lowering agent.

In embodiment 57, the disclosure provides for the use in a treatment of an CB1 receptor related disorder of compound represented by the Formula I, II or III or any of embodiments 1-52.

4. BRIEF DESCRIPTION OF THE FIGURES

Figure 1B:
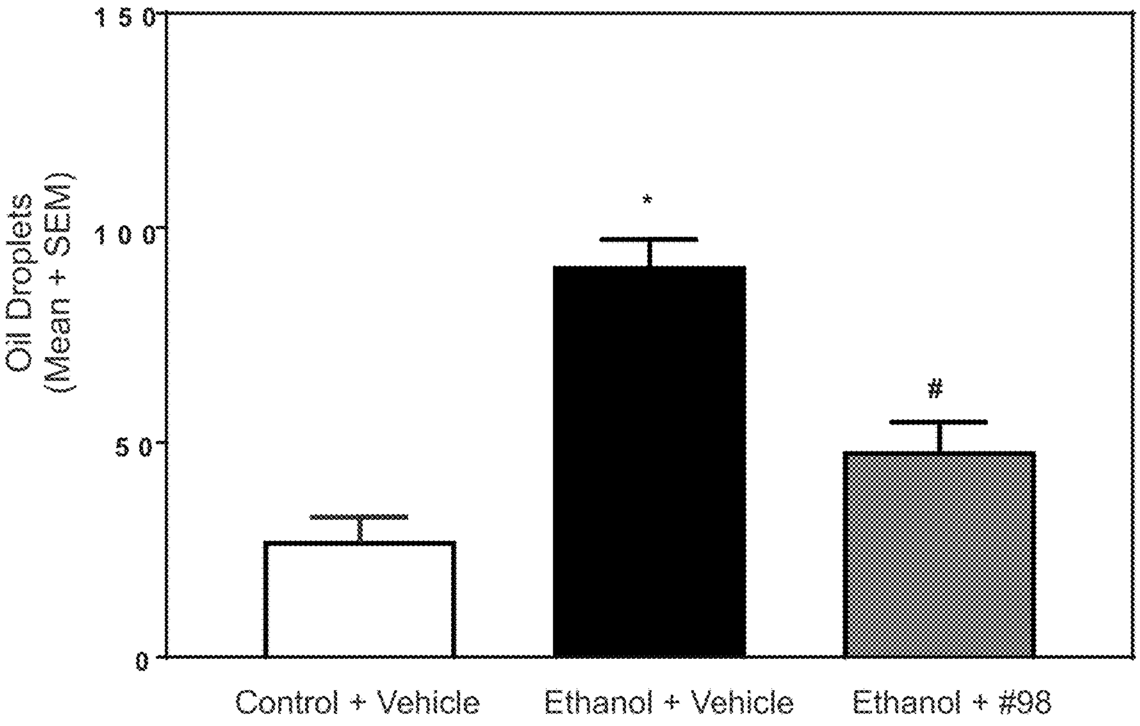

FIG. 1A-1B. Oil Red O staining of liver sections indicate reduction of steatosis upon treatment with compound 98. (FIG. 1A) Representative liver sections from mice receiving control diet without ethanol+vehicle (left panel), ethanol containing diet+vehicle (center panel) or ethanol containing diet+98 (right panel). (FIG. 1B) Quantification (Image J software) of lipid droplets in liver sections indicated statistically significant reduction of liver steatosis upon treatment with 98 (ANOVA, *, p<0.001 vs control+vehicle; #, p<0.01 vs ethanol+vehicle).

5. DETAILED DESCRIPTION OF THE DISCLOSURE

This disclosure provides a compound of the Formula I, II or III. The disclosure also provides compounds as shown in Table 2.

In addition, the disclosure also provides compounds having the following structures.

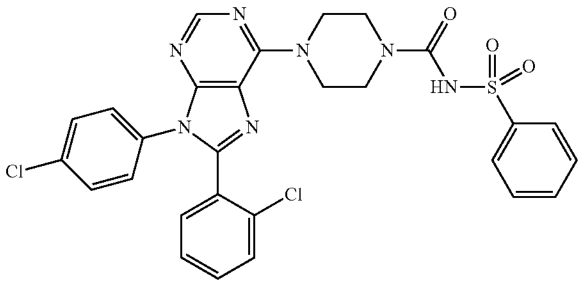

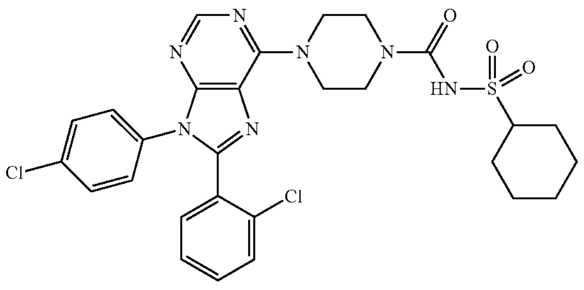

-continued

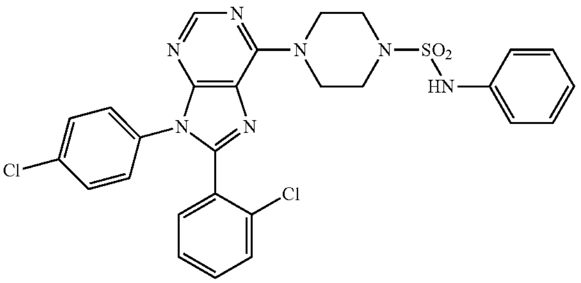

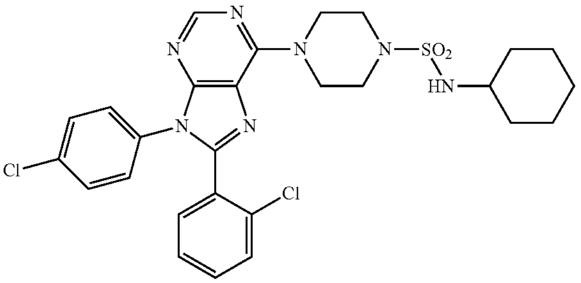

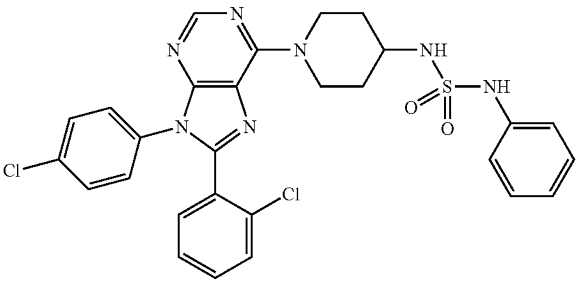

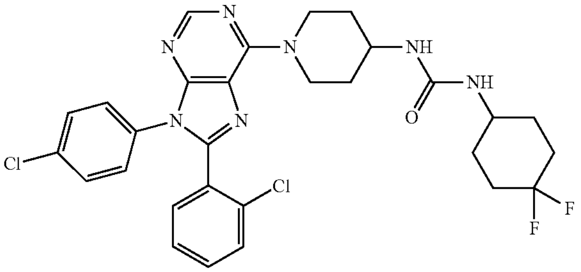

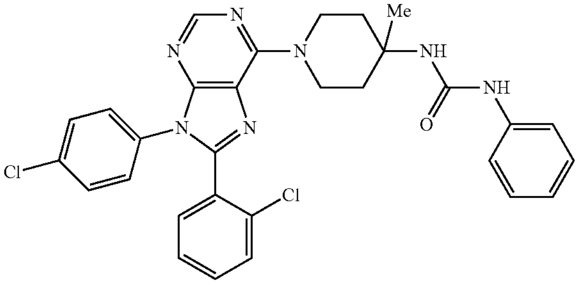

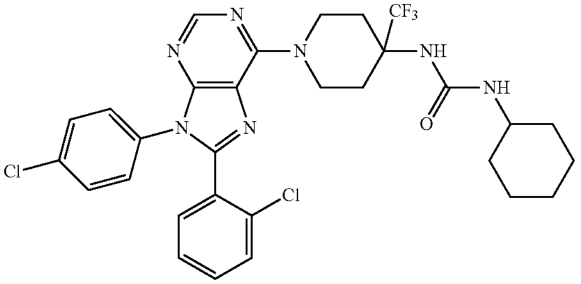

-continued

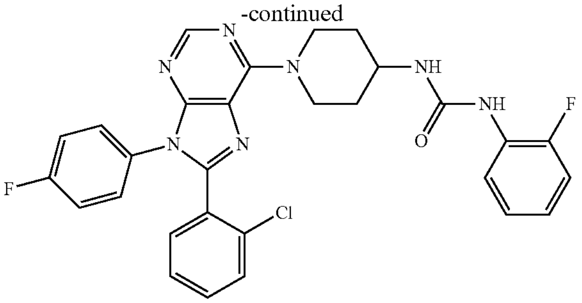

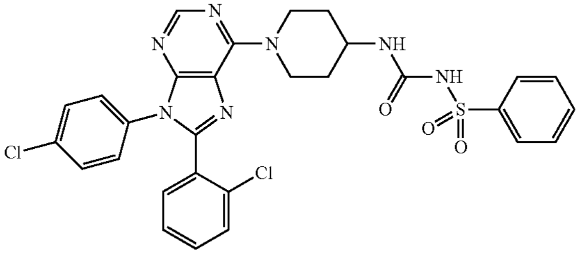

5.1. Definitions

While the following terms are believed to be well understood by one of ordinary skill in the art, the following definitions are set forth to facilitate explanation of the presently disclosed subject matter.

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. The alkenyl group may be substituted or unsubstituted. In certain embodiments, an alkenyl group has from 2 to 20 carbon atoms and in other embodiments from 2 to 8 carbon atoms. Where the alkenyl group is attached to a nitrogen or other heteroatom, the first two carbons of the chain will be saturated, e.g., $N(CH_2)_2CH{=}CCHR$.

"Alkoxy" refers to a radical —OR where R represents an alkyl, alkyl, cycloalkyl, aryl, or heteroaryl group as defined herein. Representative examples include, but are not limited to, methoxy, ethoxy, propoxy, butoxy, cyclohexyloxy, and the like. The alkoxy group may be substituted or unsubstituted.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted; for example with one or more halogens, e.g., difluoro or trifluoro substituents is as in a difluoromethyl or a trifluoromethyl group. In certain embodiments, an alkyl group comprises from 1 to 20 carbon atoms. Alternatively, an alkyl group may comprise from 1 to 8 carbon atoms.

"Alkyl(aryl)" refers to an acyclic alkyl group in which one of the hydrogen atoms bonded to a carbon atom, typically a terminal or $sp^3$ carbon atom, is replaced with an aryl group. Typical alkyl(aryl) groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In certain embodiments, an alkyl(aryl) group can be $(C_{6-20})$ alkyl(aryl) e.g., the alkyl group may be $(C_{1-10})$ and the aryl moiety may be $(C_{5-10})$.

"Alkoxy(aryl)" refers to an acyclic alkoxy group in which one of the hydrogen atoms bonded to a carbon atom, typically a terminal or $sp^3$ carbon atom, is replaced with an aryl group. Typical alkoxy(aryl) groups include, but are not limited to, benzyloxy, 2-phenylethanoxy and the like. In certain embodiments, an alkoxy(aryl) group can be $(C_{6-20})$ alkoxyl(aryl) e.g., the alkoxy group may be $(C_{1-10})$ and the aryl moiety may be $(C_{5-10})$. The alkyl(aryl) group may be substituted or unsubstituted.

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, ethynyl, propynyl, butenyl, 2-pentynyl, 3-pentynyl, 2-hexynyl, 3-hexynyl and the like. The alkynyl group may be substituted or unsubstituted. In certain embodiments, an alkynyl group has from 3 to 20 carbon atoms and in other embodiments from 3 to 8 carbon atoms. Where the alkynyl group is attached to a nitrogen or other heteroatom, the first two carbons of the chain will be saturated, e.g., $N(CH_2)_2CH{\equiv}CCHR$. The alkyl(aryl) group may be substituted or unsubstituted.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; bicyclic ring systems wherein at least one ring is carbocyclic and aromatic, for example, naphthalene, indane; or two aromatic ring systems, for example benzyl phenyl, biphenyl, diphenylethane, diphenylmethane. The aryl group may be substituted or unsubstituted, for example with a halogen, such as fluorine.

"Cycloalkoxy" refers to a saturated or unsaturated cyclic alkyl group containing one or more oxygen atoms in the ring. Typical cycloalkoxy groups include, but are not limited to, groups derived from cyclopropane, cyclobutane, cyclopentane, cyclohexane, and the like such as dioxolane, oxetane, oxirane, tetrahydrofuran. The cycloalkoxy group may be substituted or unsubstituted. In certain embodiments, the cycloalkyl group can be $C_{2-10}$ cycloalkoxy, such as, for example, $C_4$ cycloalkoxy.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. The cycloalkyl group may be substituted or unsubstituted. In certain embodiments, the cycloalkyl group can be $C_{3-10}$ cycloalkyl, such as, for example, $C_6$ cycloalkyl. The cycloalkyl group may also be a bridged bicyclic cycloalkyl group, a fused cycloalkyl group or a spiro cycloalkyl group. Non-limiting examples of bridged bicyclic cycloalkyl groups are bicyclo[2.2.1]heptane, bicyclo[2.2.1]hexane, bicycle[2.2.2]octane. An example of a fused cycloalkyl group is bicyclo[4.4.0]decane or decalin. Non-limiting examples of spiro cycloalkyl groups are spiro [3.3] heptane, spiro [4.3] octane, or spiro [5.4] decane.

"Disease" refers to any disease, disorder, condition, symptom, or indication.

"Halogen" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. The heteroaryl group may be substituted or unsubstituted.

For example, heteroaryl includes a 5- to 7-membered heteroaromatic ring fused to a 5- to 7-membered cycloalkyl ring and a 5- to 7-membered heteroaromatic ring fused to a saturated 5- to 7-membered heterocycle. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Typical heteroaryl groups include, but are not limited to, groups derived from acridine, arsindole, benzodioxin, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, piperidine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heterocyle" refers to a monovalent saturated cyclic group derived by the removal of one hydrogen atom from a single atom of a parent heterocylic ring system. Heterocycle encompasses: 3- to 7-membered saturated monocyclic rings containing one or more, for example, from 1 to 3, heteroatoms chosen from N, O, and S, with the remaining ring atoms being carbon. The heterocycle may be substituted or unsubstituted. Non-limiting examples of heterocycles are: azepane, azetidine, aziridine, dioxolane, dithiolane, homopiperazine imidazolidine isothiazolidine, isoxazolidine, morpholine, oxane, oxazolidine oxepane, oxetane, oxirane, oxolane, piperazine, piperidine, pyrazolidine, pyrrolidine, thiane, thiazolidine, thiepane, thietane, thiirane, thiolane, or thiomorpholine groups. The heterocycle group may be bicyclic such as a heterospiro compound, e.g., heterospiro [3.3] heptanyl, heterospiro [3.4] octanyl, or heterospiro [5.5] undecanyls. The heterocycle group may be substituted or unsubstituted.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Prodrug" refers to a precursor or derivative form of a pharmaceutically active substance that is less bioactive compared to the parent drug and is capable of being enzymatically activated or converted into the more active parent form. Prodrug forms of the compounds described herein may be designed to improve bioavailability or stability or reduce toxicity. For example, compounds of the disclosure having free amino, amido, carboxylic, hydroxyl, or thiol groups can be converted into prodrugs. See Rautio et al., 2008 Nat Rev Drug Dis 7 255-270. For instance, free carboxyl groups can be derivatized as amides, carbamates, esters, or N-Mannich bases. Free hydroxy groups may be derivatized using groups including but not limited to carbonates, dimethylaminoacetates, ethers, hemisuccinates, phosphate esters, and phosphoryloxymethyloxycarbonyls, as outlined in Fleisher et al., 1996 Advanced Drug Delivery Reviews 19, 115-130. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in Robinson et al., 1996 J Med Chem 39 10-18. Free amines can also be derivatized as amides, carbamates, imines, N-Mannich bases, oximes, phosphonamides, or sulfonamides. Carbonyls may be derivatized to imine or oxime prodrugs. Thiols may be derivatized as esters or ethers. Prodrugs may also include compounds wherein an amino acid residue, or a polypeptide chain of two or more (e.g., two, three or four) amino acid residues is covalently joined through an amide or ester bond to a free amino, hydroxy or carboxylic acid group of compounds of the disclosure. The amino acid residues include but are not limited to the 20 naturally occurring amino acids commonly designated by three letter symbols and also includes beta-alanine, citrulline, demosine, gamma-aminobutyric acid, homocysteine, homoserine, 4-hydroxyproline, hydroxylysine, isodemosine, 3-methylhistidine, norvalin, methionine sulfone, and ornithine.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subject" includes mammals and humans. The terms "human" and "subject" are used interchangeably herein.

"Substituted" refers to a group in which one or more hydrogen atoms are each independently replaced with the same or different substituent(s). Typical substituents include, but are not limited to, $CO_2H$, cyano, difluoro (including in an alkyl or cyclo chain $—CF_2—$ or $—CHF_2$ at the end of a chain or as a side group), halogen, hydroxyl, $—N_3$, $—H_2$, $—SO_{(1-3)}H$, —SH, or trifluoro (e.g., $—CF_3$. at the end of a chain or as a side group).

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Pairs of the functional groups defined herein may be combined in a chemically rational way. For example, $C_1$-$C_8$ alkyl amino means the functional group $C_1$-$C_8$ alkyl, e.g., $-nC_5H_{11}$, is combined with the functional group, amino, e.g., $—NH_2$ to form in this example $-nC_5H_{10}NH_2$. Similarly, $C_1$-$C_8$ alkoxy aryl means the functional group $C_1$-$C_8$ alkoxy, e.g., $—CH_2CH_2OCH_2CH_3$ or $—OCH_2CH_3$ combined with an aryl group, e.g., $—C_6H_5F$ to form $—CH_2CH_2OCH_2CH_2—C_6H_5F$ or $—OCH_2CH_3—C_6H_5F$, respectively.

Throughout the present specification, the terms "about" and/or "approximately" may be used in conjunction with numerical values and/or ranges. The term "about" is understood to mean those values near to a recited value. For example, "about 40 [units]" may mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

As used herein, the verb "comprise" as is used in this description and in the claims and its conjugations are used in its non-limiting sense to mean that items following the word are included, but items not specifically mentioned are not excluded.

Throughout the specification the word "comprising," or variations such as "comprises" will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Certain compounds according to Formulas I, II and III are compounds with relatively high topological polar surface areas ("TPSA"s). TPSA has been shown to correlate to passive transport through membranes. In certain embodiments, it is desirable to provide compounds with minimal blood-brain barrier penetration. Such compounds may target peripheral receptors and thus reduce potential central nervous system-related side effects. Generally, higher TPSA values correspond to lower penetration into the CNS and may thus be desirable.

A TPSA can be calculated for any given compound to predict that compound's ability to penetrate the blood-brain barrier. Various methods can be used for such calculations and predictions, such as computational models. For example, methods for calculating molecular polar surface area as a sum of fragment based contributions are described in Ertl et al., *J. Med. Chem.* 43: 3714-3417 (2000), which is incorporated herein by reference. In certain embodiments, TPSA values for compounds are calculated using commercially available software from Advanced Chemistry Development (ACD 10, ACD/ChemSketch). In some preferred embodiments, compounds of Formulas I, II and/or III are provided, wherein the TPSAs of such compounds are greater than that of otenabant (i.e., greater than about 50). For example, in certain embodiments, the TPSAs of compounds according to the present disclosure are greater than about 55, greater than about 60, greater than about 65, greater than about 70, or greater than about 75. Certain compounds may exhibit TPSAs of greater than about 80, greater than about 90, or greater than about 100.

Accordingly, in certain embodiments of the present disclosure, compounds are provided which exhibit relatively low penetration through the blood-brain barrier. For example, compounds may preferably exhibit lower penetration through the blood-brain barrier than rimonabant. Penetration of compounds can be measured by any means, including, but not limited to: in vivo methods such as intravenous injection/brain sampling, brain uptake index, brain perfusion, quantitative autoradiography, external registration (MRI, SPECT, PET), microdialysis, or CSF sampling; and in vitro methods such as binding, uptake, and efflux measurements on fresh isolated brain microvessels and endothelial cell cultures. Reviews of various methods for prediction and measurement of blood-brain barrier penetration can be found in Bickel, *NeuroRx*® 2:15-26 (2005) and Liu, *Drug Metabolism and Disposition* 32 (1): 132-139 (2004), which are both incorporated herein by reference.

The compounds disclosed herein as active agents may contain chiral centers, which may be either of the (R) or (S) configuration, or may comprise a mixture thereof. Accordingly, the present disclosure also includes stereoisomers of the compounds described herein, where applicable, either individually or admixed in any proportions. Stereoisomers may include, but are not limited to, enantiomers, diastereomers, racemic mixtures, and combinations thereof. Such stereoisomers can be prepared and separated using conventional techniques, either by reacting enantiomeric starting materials, or by separating isomers of compounds of the present disclosure. Isomers may include geometric isomers. Examples of geometric isomers include, but are not limited to, cis isomers or trans isomers across a double bond. Other isomers are contemplated among the compounds of the present disclosure. The isomers may be used either in pure form or in admixture with other isomers of the compounds described herein.

In some embodiments, the compounds of Formula I, II or III are racemic. In some embodiments, compounds with one or more chiral centers are provided. While racemic mixtures of compounds of the disclosure can be active, selective, and bioavailable, isolated isomers may be of interest as well. The compounds of the present disclosure optionally may be provided in a composition that is enantiomerically enriched, such as a mixture of enantiomers in which one enantiomer is present in excess, in particular to the extent of 95% or more, or 98% or more, including 100%.

Various methods are known in the art for preparing optically active forms and determining activity. Such methods include standard tests described herein other similar tests which are well-known in the art. Examples of methods that can be used to obtain optical isomers of the compounds according to the present disclosure include the following:

i) physical separation of crystals whereby macroscopic crystals of the individual enantiomers are manually separated. This technique may particularly be used when crystals of the separate enantiomers exist (i.e., the material is a conglomerate), and the crystals are visually distinct;

ii) simultaneous crystallization whereby the individual enantiomers are separately crystallized from a solution of the racemate, possible only if the latter is a conglomerate in the solid state;

iii) enzymatic resolutions whereby partial or complete separation of a racemate by virtue of differing rates of reaction for the enantiomers with an enzyme;

iv) enzymatic asymmetric synthesis, a synthetic technique whereby at least one step of the synthesis uses an enzymatic reaction to obtain an enantiomerically pure or enriched synthetic precursor of the desired enantiomer;

v) chemical asymmetric synthesis whereby the desired enantiomer is synthesized from an achiral precursor under conditions that produce asymmetry (i.e., chirality) in the product, which may be achieved using chiral catalysts or chiral auxiliaries;

vi) diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers;

viii) kinetic resolutions comprising partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors whereby the desired enantiomer is obtained from non-chiral starting materials and where the stereochemical integrity is not or is only minimally compromised over the course of the synthesis;

x) chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography whereby the racemate is volatilized and enantiomers are separated by virtue of their differing interactions in the gaseous mobile phase with a column containing a fixed non-racemic chiral adsorbent phase;

xii) extraction with chiral solvents whereby the enantiomers are separated by virtue of preferential dissolution of one enantiomer into a particular chiral solvent; and xiii) transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The terms (R) and (S) as used herein mean that the composition contains a greater proportion of the named isomer of the compound in relation to other isomers. In a preferred embodiment these terms indicate that the composition contains at least 90% by weight of the named isomer and 10% by weight or less of the one or more other isomers; or more preferably about 95% by weight of the named isomer and 5% or less of the one or more other isomers. These percentages are based on the total amount of the compound of the present disclosure present in the composition.

5.2. Deuterated and Other Isotopic Variants

The disclosure also includes all suitable isotopic variations of a compound of the disclosure. An isotopic variation of a compound of the disclosure is defined as one in which at least one atom is replaced by an atom having the same atomic number but an atomic mass different from the atomic mass usually or predominantly found in nature. Examples of isotopes that can be incorporated into a compound of the disclosure include isotopes of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the disclosure, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Substitution with positron emitting isotopes, such as $^{11}C$, $^{18}F$, $^{15}O$ and $^{13}N$, can be useful in Positron Emission Topography (PET) studies.

Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the disclosure can generally be prepared by conventional procedures known by a person skilled in the art such as by the illustrative methods or by the preparations described in the examples hereafter using appropriate isotopic variations of suitable reagents. In another embodiment, the isotope-labeled compounds contain deuterium ($^{2}H$), tritium ($^{3}H$) or $^{14}C$ isotopes. Isotope-labeled compounds of this disclosure can be prepared by the general methods well known to persons having ordinary skill in the art.

Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. Alternatively, deuterium may be also incorporated into a compound using methods such as through reduction such as using $LiAlD_4$ or $NaBD_4$, catalytic hydrogenation or acidic or basic isotopic exchange using appropriate deuterated reagents such as deuterides, $D_2$ and $D_2O$. In addition to the above, PCT publications, WO2014/169280; WO2015/058067; U.S. Pat. Nos. 8,354,557; 8,704,001 and US Patent Application Publication Nos.; 2010/0331540; 2014/0081019; 2014/0341994; 2015/0299166, the methods are hereby incorporated by reference.

5.3. Combinations

In specific embodiments, active agents used in combination with compounds of the present disclosure comprise one or more compounds generally recognized as useful for treating the conditions discussed herein. In one embodiment, the use of two or more drugs, which may be of different therapeutic classes, may enhance efficacy and/or reduce adverse effects associated with one or more of the drugs.

For example, in certain embodiments, the present disclosure relates to the treatment of obesity. Accordingly, in one embodiment, a compound of Formula I, II or III is combined with one or more known anti-obesity drugs for the treatment of obesity. Common therapeutic classes of obesity drugs include those that decrease food intake by either reducing appetite or increasing satiety, those that decrease nutrient absorption, and those that increase energy expenditure. Examples of known antiobesity drugs include: phentermine, which is an appetite suppressant; topiramate, which is an depressant/epilepsy drug that has been shown to interfere with binge eating and may result in decreased weight and decreased blood pressure; Orlistat (Xenical, Alli®), which reduces intestinal fat absorption by inhibiting pancreatic lipase; Sibutramine (Reductil or Meridia), which is an anorectic or appetite suppressant; diethylpropion (diethylcathinone/amfepramone, also sold as Anorex,® Tenuate,® and Tepanil®), which is a stimulant marketed as an appetite suppressant (which functions as a prodrug for ethcathinone); Mazindol (Mazanor, Sanorex), which is a tetracyclic stimulant drug used for short-term treatment of obesity; Rimonabant (Acomplia), which is a compound that is a cannabinoid (CB1) receptor antagonist that acts centrally on the brain to decrease appetite and may also increase energy expenditure; metformin (glucophage) in people with diabetes mellitus type 2; Exenatide (Byetta) and Pramlintide (Symlin), which both delay gastric emptying and promote a feeling of satiety. Other over-the-counter weight loss products including herbal remedies, laxatives, diet pills, diuretic drugs, and/or pyruvate may also be combined with the compounds disclosed herein. The compounds disclosed herein may also be used in combination with non-drug-based therapy, including caloric restriction, exercise, and behavioral therapy.

Combinations of compounds of the present disclosure with other therapeutic agents are also included in the present disclosure, wherein the condition to be treated is any condition that may be responsive to the antagonism of the CB1 receptor.

For example, diabetes may be treated with compounds of the present disclosure, and thus, in one embodiment, a compound of Formula I, II or III is combined with one or more known drugs for the treatment of diabetes. In certain embodiments, diabetes is treated with compounds of the present disclosure in combination with insulin. Diabetes medications generally fall within six classes of drugs that work in different ways to lower blood glucose levels. Specifically, these medications include sulfonylureas, which stimulate the beta cells of the pancreas to release more insulin (e.g., chlorpropamide (Diabinese), glipizide (Glucotrol and Glucotrol XL), glyburide (Micronase, Glynase, and Diabeta, and glimepiride (Amaryl)); meglitinides, which stimulate the beta cells to release insulin (e.g., repaglinide (Prandin) and nateglinide (Starlix)); biguanides, which lower blood glucose levels primarily by reducing the glucose produced by the liver (e.g., metformin (Glucophage)); thiazolidinediones, which help insulin to work better in the muscle and fat, and also reduce glucose production in the liver (e.g., rosiglitazone (Avandia) and pioglitazone (ACTOS)); alpha-glucosidase inhibitors, which help lower blood glucose levels by blocking the breakdown of starches in the intestine and may slow the breakdown of some sugars (e.g., acarbose (Precose) and meglitol (Glyset)); and DPP-4 inhibitors, which prevent the breakdown of GLP-1, which is a naturally occurring compound in the body that reduces blood glucose levels (e.g., sitagliptin (Januvia) and saxagliptin (Onglyza).

Dyslipidemia may also be treated using compounds with the present disclosure. Thus, in one embodiment, a compound of Formula I, II or III is combined with one or more known drugs for the treatment of dyslipidemia. Medications for dyslipidemia typically fall into four classes of compounds capable of lowering lipid levels. These classes include statins, which are 3-hydroxy-3-methylglutaryl coenzyme A (HMG-CoA) reductase inhibitors (e.g.); fibrates, which reduce triglyceride and very low-density lipoprotein production in the liver (e.g., gemfibrozil, clofibrate, and fenofibrate); niacin (also known as nicotinic acid or Vitamin B3), which lowers total cholesterol and triglycerides and may also increase high-density lipoprotein cholesterol; and bile acid sequestering resins, which bind bile acids in the small intestine and prevent their return to the liver (e.g., cholestipol and cholestyramine).

Various liver diseases may be treated using compounds of the present disclosure. Accordingly, in one embodiment, a compound of Formula I, II or III is combined with one or more known drugs for the treatment of various types of liver disease. For example, exemplary medications used to treat fatty liver disease or nonalcoholic steatohepatitis include Actos, Avandia, Xenical, Actigall, Urso, Urso Forte, Orlostat, and Cystadane.

Further, in one embodiment, a compound of Formula I, II or III is combined with one or more known drugs for the treatment of pain and/or inflammation. Many such drugs are well known, and include, for example, acetaminophen (e.g., Tylenol and aspirin-free Excedrin); nonsteroidal anti-inflammatory drugs (NSAIDS, e.g., aspirin, Motrin, and Aleve); topical corticosteroids (e.g., Cortaid and Cortizone); corticosteroids (e.g., Deltasone, Hydeltrasol, and Solu-Medrol); opiods (e.g., morphine, fentanyl, oxycodone, and codeine); antidepressants (e.g., selective serotonin reuptake inhibitors (SSRIs) such as Celexa, Prozac, Paxil, and Zoloft; tricyclic antidepressants such as Elavil, Norpramin, Sinequan, Tofranil, and Pamelor; and selective serotonin and norepinephrine reuptake inhibitors (SSNRIs) such as Effexor and Cymbalta); and anticonvulsants (e.g., Tegretol, Neurontin, and Lyrica).

The compound of Formula I, II or III (and/or pharmaceutically acceptable ester, amide, salt, solvate, prodrug, and/or isomer thereof) and the one or more other therapeutic agents may be contained within a single composition or alternatively may be administered concurrently or sequentially (consecutively) in any order. For sequential administration, each of the compound of Formula I, II or III and the one or more other therapeutic agents can be formulated in its own pharmaceutical composition, each of which is to be administered sequentially, in any order. Alternatively, the compound of Formula I, II or III and the one or more other therapeutic agents can be formulated together. The compositions may be formulated for oral, systemic, topical, intravenous, intraparenteral, intravaginal, intraocular, transbuccal, transmucosal, or transdermal administration.

5.4. Pharmaceutical Compositions

The disclosure also provides pharmaceutical compositions comprising an effective amount of a compound Formula I, II or III (e.g., any of the formulae and/or structures disclosed herein), or a pharmaceutically acceptable salt of said compound; and a pharmaceutically acceptable carrier.

Pharmaceutically acceptable carriers, adjuvants and vehicles that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. If required, the solubility and bioavailability of the compounds of the present disclosure in pharmaceutical compositions may be enhanced by methods well-known in the art. One method includes the use of lipid excipients in the formulation. See "Oral Lipid-Based Formulations Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this disclosure optionally formulated with a poloxamer, such as LUTROL™ and PLURONIC™ (BASF Corporation), or block copolymers of ethylene oxide and propylene oxide. See U.S. Pat. No. 7,014,866 (Infeld et al.); and US Pat. Pubs. 20060094744 (Maryanoff et al.) and 20060079502 (Lang).

The pharmaceutical compositions of the disclosure include those suitable for oral, rectal, nasal, topical (including buccal and sublingual), pulmonary, vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product. In certain embodiments, the compound is administered orally. Compositions of the present disclosure suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this disclosure may be administered in the form of suppositories for rectal administration. These compositions can be prepared by mixing a compound of this disclosure with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g., U.S. Pat. No. 6,803,031 (Rabinowitz & Zaffaroni).

Topical administration of the pharmaceutical compositions of this disclosure is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene or polyoxypropylene compounds, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this disclosure may also be topically applied to the lower intestinal tract by rectal suppository formulation or in a suitable enema formulation. Topically-transdermal patches and iontophoretic administration are also included in this disclosure.

Application of the therapeutics may be local, so as to be administered at the site of interest. Various techniques can be used for providing the compositions at the site of interest, such as injection, use of catheters, trocars, projectiles, pluronic gels, stents, sustained drug release polymers or other devices which provide for internal access. Thus, according to yet another embodiment, the compounds of this disclosure may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562 (Ding & Helmus); 5,886,026 (Hunter et al.); and 5,304,121 (Sahatjian). The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the disclosure provides a method of coating an implantable medical device comprising the step of contacting said device with the coating composition described above. It will be obvious to those skilled in the art that the coating of the device will occur prior to implantation into a mammal.

According to another embodiment, the disclosure provides a method of impregnating an implantable drug release device comprising the step of contacting said drug release device with a compound or composition of this disclosure. Implantable drug release devices include, but are not limited to, biodegradable polymer capsules or bullets, non-degradable, diffusible polymer capsules and biodegradable polymer wafers.

According to another embodiment, the disclosure provides an implantable medical device coated with a compound or a composition comprising a compound of this disclosure, such that said compound is therapeutically active.

According to another embodiment, the disclosure provides an implantable drug release device impregnated with or containing a compound or a composition comprising a compound of this disclosure, such that said compound is released from said device and is therapeutically active. Where an organ or tissue is accessible because of removal from the subject, such organ or tissue may be bathed in a medium containing a composition of this disclosure, a composition of this disclosure may be painted onto the organ, or a composition of this disclosure may be applied in any other convenient way.

5.5. Methods of Use

In a further embodiment, the present disclosure provides a method for treating or delaying the progression of disorders that are alleviated by antagonizing the CB1 receptors in a patient, the method comprising administering a therapeutically effective amount of at least one compound of Formula I, II or III to the patient.

In particular, the present disclosure relates to the field of treating obesity in animals, particularly humans and other mammals, and associated effects of these conditions. It also may relate to the treatment of other conditions that may benefit from the antagonism of CB1 receptors, such as liver diseases, dyslipidemia, pain/inflammation, and metabolic disorder. In some embodiments, the compounds show selectivity for CB1 over other cannabinoid receptors.

Obesity has its common meaning, e.g., the medical condition that exists when an individual has accumulated excess body fat, which may lead to a variety of related health problems, and which is characterized by a body mass index (BMI) of 30 $kg/m^2$ or more. Pre-obesity, also known as overweight, refers to the condition wherein an individual's BMI is between 25 $kg/m^2$ and 30 $kg/m^2$.

The method of treatment generally includes administering a therapeutically effective amount of a compound of Formula I, II or III, optionally in a pharmaceutical composition including one or more pharmaceutically acceptable carriers. The therapeutically effective amount is preferably sufficient to antagonize the CB1 receptor. The therapeutically effective amount is further preferably sufficient to cause some relief to the patient in the symptoms of the disorder for which the patient is being treated.

For example, in one embodiment, a method of treating obesity is provided. In such methods, a therapeutically effective amount of a compound of the present disclosure to treat a patient with pre-obesity or obesity may be that amount capable of antagonizing the CB1 receptor. Such compound may cause the patient to experience decreased appetite and/or may create a sensation of fullness. The method of treating obesity may be used to attain or maintain a patient's weight loss.

In another embodiment, a method of treating liver disease is provided. The liver disease may be, for example, fatty liver disease such as nonalcoholic steatohepatitis (NASH) (e.g., obesity-related steatosis) or alcoholic steatosis. For example, compounds of the present disclosure can, in some embodiments, be used to slow the development of fatty liver (alcoholic or non-alcoholic fatty liver) and, in some cases, prevent the progression of fatty liver to more severe forms of liver disease. In some embodiments, compounds of the present disclosure may function to provide hepatoprotective activity. In some embodiments, the compounds may be capable of modulating lipid levels, reducing cholesterol, free fatty acids, and/or triglycerides.

In some embodiments, a method of treating diabetes is provided. Diabetes can be type 1, type 2, pre-diabetes, gestational diabetes, or latent autoimmune diabetes of adults (LADA). In some cases, the diabetes is associated with a disorder that has caused damage to the pancreas, such as cystic fibrosis, chronic pancreatitis, or haemochromatosis.

In some embodiments, a method of treating metabolic syndrome, a cluster of conditions such as high blood sugar and high triglycerides that can lead to cardiovascular disease, is provided. In certain other embodiments, a method of smoking cessation and/or a method for preventing weight gain in former smokers is provided.

The therapeutically effective dosage amount of any specific formulation will vary somewhat from drug to drug, patient to patient, and will depend upon factors such as the condition of the patient and the route of delivery. When administered conjointly with other pharmaceutically active agents, even less of the compounds of the disclosure may be therapeutically effective. Furthermore, the therapeutically effective amount may vary depending on the specific condition to be treated.

The compounds of the disclosure can be administered once or several times a day. The daily dose can be administered either by a single dose in the form of an individual dosage unit or several smaller dosage units or by multiple administration of subdivided dosages at certain intervals. Possible routes of delivery include buccally, subcutaneously, transdermally, intramuscularly, intravenously, orally, or by inhalation.

The compounds of the disclosure may be used with other types of therapy, including those which are non-drug based. Thus, in some embodiments, the methods of the present disclosure comprise administering to a subject a compound that that is capable of functioning as an antagonist of CB1 receptors in conjunction with one or more other types of non-drug-based therapy.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

6. EXAMPLES

Synthetic and characterization data are provided below for various compounds intended to be encompassed within various embodiments of the disclosure. It is noted that not all of the compounds described within the Experimental Section are included within the general genus structure of Formulas I, II or III as provided above. However, such compounds are intended to be included as further alternative embodiments of the disclosure and the application should be read as such. Thus, the application should be construed as directed not only to compounds that fall within Formulas I, II or III, but also to compounds that are specifically referenced within the Experimental section.

Compounds according to Formulas I, II or III having each of the $R_x$ substituents recited in this table are also intended to be encompassed herein. Thus, these $R_x$ groups can be considered to be, in certain embodiments, components of not only the specific structure provided in Tables 1 and 2, but also components of the broader genus set forth in Formulas I, II or III (i.e., compounds provided on pages 7-8 are included within the present disclosure as well as analogues thereof, comprising other substituents at various locations within the molecule, as provided for within Formulas I, II and III).

6.1. Example 1. Synthesis

Purity and characterization of compounds were established by a combination of HPLC, TLC, and NMR analytical techniques described below. $^1H$ spectra were recorded on a Bruker Avance DPX-300 (300 MHz) spectrometer and were determined in $CHCl_3$-d or MeOH-d4 with tetramethylsilane (TMS) (0.00 ppm) or solvent peaks as the internal reference unless otherwise noted. Chemical shifts are reported in ppm relative to the solvent signal, and coupling constant (J) values are reported in hertz (Hz). Thin-layer chromatography (TLC) was performed on EMD precoated silica gel 60 F254 plates, and spots were visualized with UV light or $I_2$ detection. Low-resolution mass spectra were obtained using a Waters Alliance HT/Micromass ZQ system (ESI).

All test compounds were greater than 95% pure as determined by HPLC on an Agilent 1100 system using an Agilent Zorbax SB-Phenyl, 2.1×150 mm, 5 μm column with gradient elution using the mobile phases (A) $H_2O$ containing 0.05% $CF_3COOH$ and (B) Methanol. A flow rate of 1.0 mL/min was used.

One pathway to piperazine or piperidine substituted purines is to make a 6-chloropurine intermediate, as shown below, and then react it with a small excess of the appropriate piperazine or piperidine.

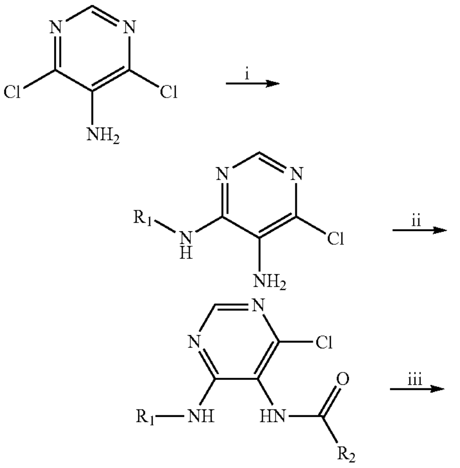

-continued

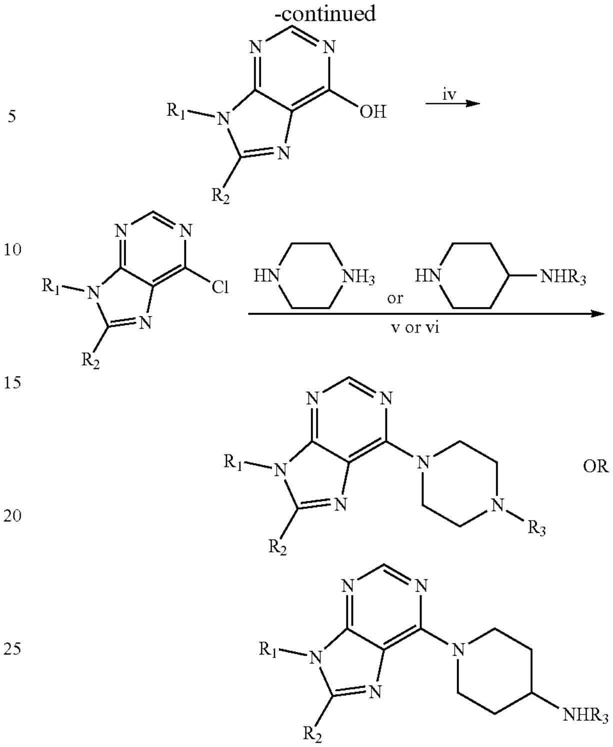

Reagents and conditions: (i) $R_1NH_2$, EtOH, heat; (ii) $R_2COCl$, NMP, heat; (iii) Acid, heat; (iv) $POCl_3$, heat; (v) TEA, EtOH, heat; (vi) $K_2CO_3$, NMP, 80° C., 15 h.

The Boc-piperazine intermediate shown below, was deprotected and then further elaborated to piperazine ureas, amides, sulfonamides and carbamates. Piperidine ureas, amides, sulfonamides and carbamates were made in a similar fashion.

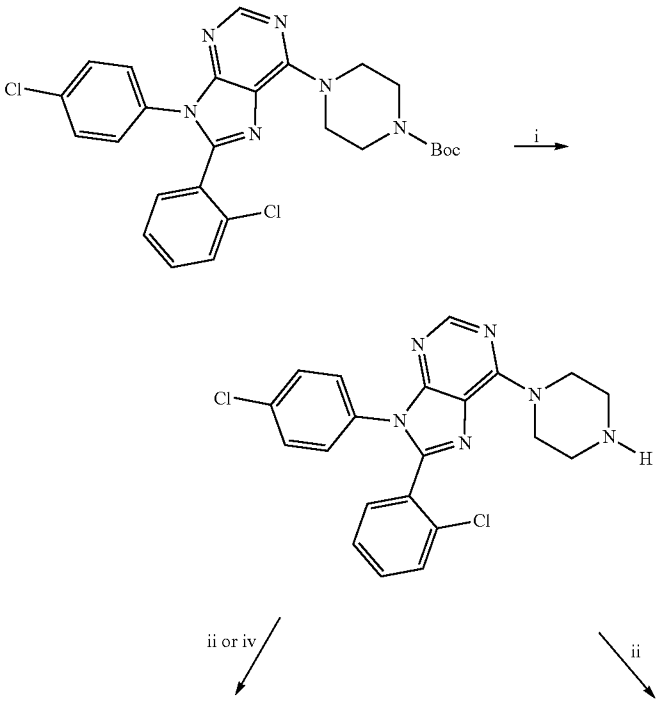

-continued

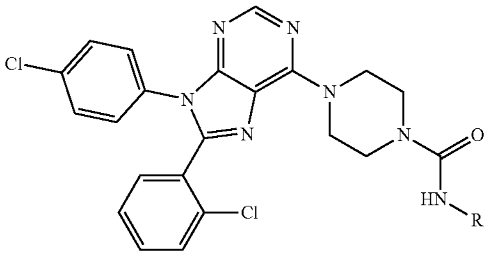

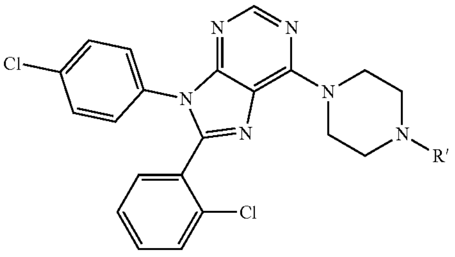

R′ = $SO_2R$, COR or $CO_2R$

Reagents and conditions: (i) TFA, DCM, rt, 3 h; (ii) RCOCl, $RSO_2Cl$, or ROCOCl; DCM, DMAP, TEA, rt, 16 hr; (iii) RNCO, TEA, THF, rt, 15 h; (iv) $RNH_2$, Triphosgene, $NaHCO_3$, DCM, rt, 1 h, then TEA, THF, rt, 15 h.

6.1.1. General Method A for Making Piperazine or Piperidine Substituted Purines To a solution of the appropriate 6-chloropurine (0.25 mmol) in EtOH (5 ml) was added TEA (0.75 mmol, 3 eq., 0.10 ml) and the appropriate piperazine or piperidine (0.31 mmol, 1.25 eq.). The reaction vessel was capped and the mixture stirred at 78° C. overnight. The resulting mixture was concentrated and chromatographed on a 4 g silica gel column using a 0-100% EtOAc/hexanes gradient. TLC and MS were used to identify the fractions with the desired product. The fractions were concentrated and dried under high vacuum overnight to provide the product, most of which were white to off-white solids.

6.1.2. General Method B for Deprotecting t-Boc Protected Piperazines or Piperidines The Boc-amine (1 mmol) was dissolved in DCM (10 ml) and TFA (10 ml) was added. The reaction was stirred at RT under a slow nitrogen stream for 16 hours, then concentrated under vacuum. The crude residue was chromatographed using a 0-100% gradient of EtOAc/MeOH/TEA (90:9:1) in hexanes to provide the amine as the freebase.

6.1.3. General Method C for Making Piperazine or Piperidine Amides and Sulfonamides The amine (1 mmol) was dissolved in DCM (10 ml) and DMAP (0.1 mmol) was added, followed by TEA (2 mmol). The acid chloride or sulfonyl chloride (1.2 mmol) was added and the reaction stirred at RT under nitrogen for 16 hours, then concentrated. The crude residue was chromatographed on a 4 gram silica gel column using a 0-100% gradient of EtOAc in hexanes to provide the purified amide or sulfonamide.

6.1.4. General Method D for Making Piperazine or Piperidine Ureas

To a solution of the appropriate piperazine (0.2 mmol, 1 equiv) in THF (1 mL) was added the appropriate isocyanate (0.24 mmol, 1.2 equiv), followed by triethylamine (0.24 mmol, 1.2 equiv). The mixture was stirred at rt for 15 hours. Water (0.4 mL) was added, followed by ethyl acetate (3 mL) and then saturated $NaHCO_3$ solution (0.8 mL). After 10 minutes, the aqueous layer was removed. Celite® (600 mg) was added to the organic layer and the solvent was evaporated. Flash chromatography using silica gel with an EtOAc/hexanes gradient provided the purified urea.

6.1.5. General Method E for Making Piperazine or Piperidine Ureas

To an ice cold solution of the appropriate amine (0.4 mmol, 2 equiv) in dichloromethane (1 mL) was added $NaHCO_3$ (0.6 mmol, 3 equiv), followed by saturated $NaHCO_3$ solution (0.6 mL). Triphosgene (0.2 mmol, 1 equiv) was added and after 10 minutes, the ice bath was removed and the mixture was stirred at rt for 1 hour (gas evolution). Saturated $NaHCO_3$ solution (0.6 mL) and water (0.3 mL) were added. After 10 minutes, the aqueous layer was removed and the organic layer dried with sodium sulfate (20 minutes). The mixture was filtered, toluene (0.5 ml) was added and most of the solvent evaporated. THF (1 mL) was added followed by the appropriate piperazine or piperidine (0.2 mmol, 1 equiv) and then triethylamine (0.4 mmol, 2 equiv). The mixture was stirred at rt for 15 hours. Ethyl acetate (3 mL) was added, followed by saturated $NaHCO_3$ solution (0.8 mL) and water (0.4 mL). After 10 minutes, the aqueous layer was removed. Celite® (600 mg) was added to the organic layer and the solvent was evaporated. Flash chromatography using silica gel with an EtOAc/hexanes gradient provided the purified urea.

6.1.6. General Method F for Making Piperazine Substituted Purines

To a solution of the appropriate chloropurine (0.2 mmol, 1 equiv) and the appropriate piperazine (0.24 mmol, 1.2 equiv) in NMP (0.8 mL) was added potassium carbonate (0.6 mmol, 3 equiv). The mixture was stirred at rt for 10 minutes and then heated at 80° C. for 15 hours. Ethyl acetate (3 mL) was added, followed by brine (1.6 mL) and water (0.8 mL). The aqueous layer was removed and the organic layer was washed with 0.8 M $NaHCO_3$ solution (2×1 mL). Celite® (600 mg) was added to the organic layer and the solvent was evaporated. Flash chromatography using silica gel with an EtOAc/hexanes gradient provided the purified product.

6.1.7. General Method G for Making Piperazine or Piperidine Ureas

To an ice cold solution of the appropriate piperazine or piperidine (0.2 mmol, 1 equiv) in dichloromethane (1 mL) was added $NaHCO_3$ (0.6 mmol, 3 equiv), followed by saturated $NaHCO_3$ solution (0.6 mL). Triphosgene (0.2 mmol, 1 equiv) was added and after 10 minutes, the ice bath was removed and the mixture was stirred at rt for 1 hour (gas evolution). Saturated $NaHCO_3$ solution (0.6 mL) and water (0.3 mL) were added. After 10 minutes, the aqueous layer was removed and the organic layer dried with sodium sulfate (20 minutes). The mixture was filtered, toluene (0.5 ml) was added and most of the solvent evaporated. THF (1 mL) was added followed by the appropriate amine (0.4 mmol, 2 equiv) and then triethylamine (0.5 mmol, 2.5 equiv). The mixture was stirred at rt for 15 hours. Ethyl acetate (3 mL) was added, followed by saturated $NaHCO_3$ solution (0.8 mL) and water (0.4 mL). After 10 minutes, the aqueous layer was removed. Celite® (600 mg) was added to the organic layer and the solvent was evaporated. Flash chromatography using silica gel with an EtOAc/hexanes gradient provided the purified urea.

6.1.8. General Method H for Making Piperazine or Piperidine Amides

To a solution of the appropriate piperazine or piperidine (0.2 mmol, 1 equiv) in 5 mL of DCM were added triethylamine (0.6 mmol, 3 equiv), N,N,N',N'-Tetramethyl-O-(1H-benzotriazol-1-yl)uronium hexafluorophosphate (HBTU, 0.26 mmol, 1.30 equiv) and the appropriate carboxylic acid (1.25 equiv). The reaction was stirred overnight and then concentrated. The crude material was purified by silica gel column chromatography using a gradient of 0-100% EtOAc/hexanes. The desired fractions were identified by TLC, MS, and NMR and combined and concentrated to provide the purified amide.

6.1.9. General Method I for Making Piperazine or Piperidine Amides or Sulfonamides To a solution of the appropriate piperazine or piperidine (0.2 mmol, 1 equiv) in 1 mL of THF was added the appropriate acid chloride or sulfonyl chloride (0.24 mmol, 1.2 equiv), followed by triethylamine (0.3 mmol, 1.5 equiv). The mixture was stirred at rt for 3 hours. Water (0.4 mL), ethyl acetate (3 mL) and then saturated $NaHCO_3$ solution (0.8 mL) were added. After 10 minutes, the aqueous layer was removed. Celite® (600 mg) was added to the organic layer and the solvent was evaporated. Flash chromatography using silica gel with an EtOAc/hexanes gradient provided the purified amide or sulfonamide.

6.1.10. Synthesis of Specific Compounds

N-{1-[8-(2-Chlorophenyl)-9-(4-chlorophenyl)-9H-purin-6-yl]piperidin-4-yl}-2-fluorobenzene-1-sulfonamide (1). The title compound was prepared by the general procedure I to provide 72 mg (100%) of an off white amorphous solid, mp 185-187° C. $R_f$=0.28 (40% EtOAc/Hexanes; blue with UV). $^1$H NMR (300 MHz, $CDCl_3$) δ 8.35 (s, 1H), 7.86-8.04 (m, 1H), 7.53-7.68 (m, 1H), 7.48 (d, J=7.0 Hz, 1H), 7.29-7.43 (m, 6H), 7.14-7.25 (m, 3H), 5.14-5.43 (m, 2H), 4.83 (d, J=7.7 Hz, 1H), 3.51-3.72 (m, 1H), 3.20-3.38 (m, 2H), 1.86-2.02 (m, 2H), 1.42-1.65 (m, 2H). MS (m/z) 597.8 (M+1). HPLC=>99% at 20.43 minutes.

6-{4-[8-(2-Chlorophenyl)-9-(4-chlorophenyl)-9H-purin-6-yl]piperazin-1-yl}pyridine-3-carbonitrile (3). The title compound was prepared by the general method A to provide 56 mg (42%). $^1$H NMR (300 MHz, $CDCl_3$) δ 8.45 (d, J=1.9 Hz, 1H), 8.43 (s, 1H), 7.66 (dd, J=2.3, 9.0 Hz, 1H), 7.48-7.54 (m, 1H), 7.32-7.43 (m, 5H), 7.17-7.24 (m, 2H), 6.65 (d, J=8.9 Hz, 1H), 4.50 (br s, 4H), 3.84-3.94 (m, 4H). MS (m/z) 527.8 (M+1).

N-{1-[8-(2-Chlorophenyl)-9-(4-chlorophenyl)-9H-purin-6-yl]piperidin-4-yl}-4-fluorobenzene-1-sulfonamide (4). The title compound was prepared by the general procedure I to provide 72 mg (100%) of an off white amorphous solid, mp 196-197° C. $R_f$=0.28 (40% EtOAc/Hexanes; blue with UV). $^1$H NMR (300 MHz, $CDCl_3$) δ 8.35 (s, 1H), 7.93 (dd, J=8.5, 5.1 Hz, 2H), 7.48 (d, J=6.8 Hz, 1H), 7.28-7.42 (m, 5H), 7.10-7.24 (m, 4H), 5.11-5.41 (m, 2H), 4.95 (d, J=7.5 Hz, 1H), 3.43-3.63 (m, 1H), 3.22-3.40 (m, 2H), 1.86-2.01 (m, 2H), 1.41-1.62 (m, 2H). MS (m/z) 597.8 (M+1). HPLC=>99% at 20.47 minutes.

N-{1-[8-(2-Chlorophenyl)-9-(4-chlorophenyl)-9H-purin-6-yl]piperidin-4-yl}-2,4-difluorobenzene-1-sulfonamide (5). The title compound was prepared by the general procedure I to provide 68 mg (92%) of an off white crystalline solid, mp 232-233° C. $R_f$=0.38 (40% EtOAc/Hexanes; blue with UV). $^1$H NMR (300 MHz, $CDCl_3$) δ 8.36 (s, 1H), 7.87-8.10 (m, 1H), 7.21-7.55 (m, 8H), 7.21 (d, J=8.3 Hz, 2H), 5.32 (br s, 2H), 4.89 (d, J=7.5 Hz, 1H), 3.61 (br s, 1H), 3.16-3.46 (m, 2H), 1.89-2.15 (m, 2H), 1.48-1.68 (m, 2H). MS (m/z) 615.3 (M+1). HPLC=>99% at 20.67 minutes.

8-(2-Chlorophenyl)-9-(4-chlorophenyl)-6-[4-(4-fluorophenyl)piperazin-1-yl]-9H-purine (6). The title compound was prepared by the general method A to provide 21.6 mg (17%). $^1$H NMR (300 MHz, $CDCl_3$) δ 8.42 (s, 1H), 7.49-7.58 (m, 1H), 7.30-7.45 (m, 5H), 7.16-7.24 (m, 2H), 6.88-7.07 (m, 4H), 4.53 (br s, 4H), 3.17-3.35 (m, 4H). MS (m/z) 519.6 (M+1).

N-{1-[8-(2-Chlorophenyl)-9-(4-chlorophenyl)-9H-purin-6-yl]piperidin-4-yl}-3,4-difluorobenzene-1-sulfonamide (7). The title compound was prepared by the general procedure I to provide 73 mg (100%) of an off white amorphous solid, mp 183-184° C. $R_f$=0.33 (40% EtOAc/Hexanes; blue with UV). $^1$H NMR (300 MHz, $CDCl_3$) δ 8.35 (s, 1H), 7.62-7.85 (m, 2H), 7.48 (d, J=7.0 Hz, 1H), 7.29-7.43 (m, 6H), 7.18 (d, J=8.5 Hz, 2H), 5.14-5.49 (m, 2H), 4.87 (d, J=7.5 Hz, 1H), 3.43-3.67 (m, 1H), 3.22-3.39 (m, 2H), 1.89-2.04 (m, 2H), 1.42-1.62 (m, 2H). MS (m/z) 615.3 (M+1). HPLC=>99% at 20.91 minutes.

N-{1-[8-(2-Chlorophenyl)-9-[6-(difluoromethoxy)pyridin-3-yl]-9H-purin-6-yl]piperidin-4-yl}-3,4-difluorobenzene-1-sulfonamide (8). The title compound was prepared by the general procedure I to provide 64 mg (82%) of an off white crystalline solid, mp 212-213° C. $R_f$=0.26 (40% EtOAc/Hexanes; blue with UV). $^1$H NMR (300 MHz, $CDCl_3$) δ 8.34 (s, 1H), 8.04 (d, J=2.1 Hz, 1H), 7.60-7.83 (m, 3H), 7.54 (d, J=7.2 Hz, 1H), 7.29-7.48 (m, 5H), 6.94 (d, J=8.7 Hz, 1H), 5.29 (br s, 2H), 4.68 (d, J=7.5 Hz, 1H), 3.45-3.67 (m, 1H), 3.22-3.40 (m, 2H), 1.91-2.05 (m, 2H), 1.43-1.60 (m, 2H). MS (m/z) 648.3 (M+1). HPLC=>98% at 20.25 minutes.

4-[8-(2-Chlorophenyl)-6-{4-[(3,4-difluorobenzene)sulfonamido]piperidin-1-yl}-9H-purin-9-yl]benzamide (9). The title compound was prepared by the general procedure I to provide 69 mg (92%) of an off white crystalline solid, mp 138-140° C. $R_f$=0.18 (2% MeOH/80% EtOAc/Hexanes; blue with UV). $^1$H NMR (300 MHz, $CDCl_3$) δ 8.33 (s, 1H), 7.59-7.90 (m, 4H), 7.48 (d, J=7.2 Hz, 1H), 7.19-7.41 (m, 6H), 6.40 (br s, 2H), 5.79 (d, J=6.2 Hz, 1H), 5.26 (br s, 2H), 3.51 (br s, 1H), 3.20-3.44 (m, 2H), 1.74-2.00 (m, 2H), 1.40-1.69 (m, 2H). MS (m/z) 624.4 (M+1). HPLC=>99% at 17.51 minutes.

N-{1-[8-(2-Chlorophenyl)-9-[6-(trifluoromethyl)pyridin-3-yl]-9H-purin-6-yl]piperidin-4-yl}-3,4-difluorobenzene-1-sulfonamide (10). The title compound was prepared by the general procedure I to provide 68 mg (100%) of an off white crystalline solid, mp 214-215° C. $R_f$=0.28 (40% EtOAc/Hexanes; blue with UV). $^1$H NMR (300 MHz, $CDCl_3$) δ 8.51 (s, 1H), 8.36 (s, 1H), 7.95 (d, J=7.0 Hz, 1H), 7.66-7.84

(m, 3H), 7.61 (dd, J=7.0, 1.7 Hz, 1H), 7.29-7.51 (m, 4H), 5.30 (br s, 2H), 4.63 (d, J=7.5 Hz, 1H), 3.46-3.68 (m, 1H), 3.22-3.43 (m, 2H), 1.91-2.12 (m, 2H), 1.45-1.57 (m, 2H). MS (m/z) 650.4 (M+1), 648.4 (M−1). HPLC=>99% at 20.79 minutes.

N-{1-[8-(2-Chlorophenyl)-9-(5-methyl-1,2-oxazol-3-yl)-9H-purin-6-yl]piperidin-4-yl}-3,4-difluorobenzene-1-sulfonamide (11). The title compound was prepared by the general procedure I to provide 42 mg (81%) of a tan crystalline solid, mp 180-182° C. $R_f$=0.19 (40% EtOAc/Hexanes; blue with UV). $^1$H NMR (300 MHz, $CDCl_3$) δ 8.40 (s, 1H), 7.65-7.85 (m, 2H), 7.60 (d, J=6.2 Hz, 1H), 7.29-7.51 (m, 4H), 6.55 (s, 1H), 5.27 (br s, 2H), 4.66 (d, J=7.7 Hz, 1H), 3.45-3.64 (m, 1H), 3.19-3.41 (m, 2H), 2.46 (s, 3H), 1.88-2.05 (m, 2H), 1.40-1.61 (m, 2H). MS (m/z) 586.4 (M+1), 584.3 (M−1). HPLC=>99% at 20.39 minutes.

N-{1-[8-(2-Chlorophenyl)-9-(1-methyl-1H-pyrazol-4-yl)-9H-purin-6-yl]piperidin-4-yl}-3,4-difluorobenzene-1-sulfonamide (12). The title compound was prepared by the general procedure I to provide 60 mg (85%) of a white crystalline solid, mp 162-164° C. $R_f$=0.11 (2% MeOH/60% EtOAc/Hexanes; blue with UV). $^1$H NMR (300 MHz, $CDCl_3$) δ 8.35 (s, 1H), 7.62-7.85 (m, 3H), 7.33-7.55 (m, 5H), 7.17 (s, 1H), 5.13-5.31 (m, 2H), 3.89 (s, 3H), 3.20-3.58 (m, 3H), 1.85-2.01 (m, 2H), 1.42-1.66 (m, 2H). MS (m/z) 585.4 (M+1), 583.6 (M−1). HPLC=>99% at 18.45 minutes.

N-{1-[8-(2-Chlorophenyl)-9-(1-methyl-1H-pyrazol-3-yl)-9H-purin-6-yl]piperidin-4-yl}-3,4-difluorobenzene-1-sulfonamide (13). The title compound was prepared by the general procedure I to provide 35 mg (60%) of a tan amorphous solid, mp 206-208° C. $R_f$=0.24 (2% MeOH/80% EtOAc/Hexanes; blue with UV). $^1$H NMR (300 MHz, $CDCl_3$) δ 8.39 (s, 1H), 7.65-7.82 (m, 2H), 7.50 (d, J=6.4 Hz, 1H), 7.28-7.43 (m, 5H), 6.19 (s, 1H), 5.13-5.44 (m, 2H), 4.72 (d, J=6.6 Hz, 1H), 3.83 (s, 3H), 3.45-3.63 (m, 1H), 3.18-3.38 (m, 2H), 1.87-2.03 (m, 2H), 1.44-1.59 (m, 2H). MS (m/z) 585.2 (M+1), 583.7 (M−1). HPLC=>98% at 18.45 minutes.

N-{1-[8-(2-Chlorophenyl)-9-[6-(trifluoromethyl)pyridin-3-yl]-9H-purin-6-yl]piperidin-4-yl}pentanamide (14). The title compound was prepared by the general procedure I to provide 51 mg (76%) of an off white crystalline solid, mp 192-193° C. $R_f$=0.28 (2% MeOH/60% EtOAc/Hexanes; blue with UV). $^1$H NMR (300 MHz, $CDCl_3$) δ 8.52 (s, 1H), 8.38 (s, 1H), 7.97 (d, J=7.5 Hz, 1H), 7.77 (d, J=8.5 Hz, 1H), 7.64 (d, J=5.1 Hz, 1H), 7.32-7.52 (m, 3H), 5.47 (br s, 2H), 5.35 (d, J=7.4 Hz, 1H), 4.06-4.28 (m, 1H), 3.32 (br s, 2H), 2.08-2.28 (m, 4H), 1.30-1.69 (m, 6H), 0.92 (t, J=8.1 Hz, 3H). MS (m/z) 558.4 (M+1). HPLC=>99% at 19.73 minutes.

N-{1-[8-(2-Chlorophenyl)-9-[6-(trifluoromethyl)pyridin-3-yl]-9H-purin-6-yl]piperidin-4-yl}benzamide (15). The title compound was prepared by the general procedure I to provide 72 mg (100%) of an off white crystalline solid, mp 220-221° C. $R_f$=0.47 (2% MeOH/60% EtOAc/Hexanes; blue with UV). $^1$H NMR (300 MHz, $CDCl_3$) δ 8.52 (s, 1H), 8.39 (s, 1H), 7.98 (d, J=7.4 Hz, 1H), 7.70-7.84 (m, 3H), 7.64 (d, J=5.4 Hz, 1H), 7.32-7.56 (m, 6H), 6.06 (d, J=7.7 Hz, 1H), 5.53 (br s, 2H), 4.30-4.40 (m, 1H), 3.31-3.45 (m, 2H), 2.20-2.31 (m, 2H), 1.51-1.77 (m, 2H). MS (m/z) 578.7 (M+1). HPLC=>99% at 19.75 minutes.

3-{1-[8-(2-Chlorophenyl)-9-[6-(trifluoromethyl)pyridin-3-yl]-9H-purin-6-yl]piperidin-4-yl}-1-(cyclohexylmethyl)urea (16). The title compound was prepared by the general procedure D to provide 62 mg (100%) of an off white crystalline solid, mp 230-232° C. $R_f$=0.25 (2% MeOH/60% EtOAc/Hexanes; blue with UV). $^1$H NMR (300 MHz, $CDCl_3$) δ 8.51 (s, 1H), 8.36 (s, 1H), 7.96 (d, J=7.4 Hz, 1H), 7.76 (d, J=8.1 Hz, 1H), 7.62 (br s, 1H), 7.31-7.49 (m, 3H), 5.40 (br s, 2H), 4.49 (br s, 1H), 4.38 (d, J=6.8 Hz, 1H), 3.88-4.06 (m, 1H), 3.33 (br s, 2H), 2.99 (br s, 2H), 2.06-2.22 (m, 2H), 1.62-1.78 (m, 7H), 1.36-1.54 (m, 2H), 1.05-1.32 (m, 2H), 0.83-0.98 (m, 2H). MS (m/z) 611.9 (M−1). HPLC=>99% at 20.88 minutes.

3-{1-[8-(2-Chlorophenyl)-9-[6-(difluoromethoxy)pyridin-3-yl]-9H-purin-6-yl]piperidin-4-yl}-1-(cyclohexylmethyl)urea (17). The title compound was prepared by the general procedure D to provide 63 mg (100%) of an off white crystalline solid, mp 141-143° C. $R_f$=0.23 (2% MeOH/60% EtOAc/Hexanes; blue with UV). $^1$H NMR (300 MHz, $CDCl_3$) δ 8.36 (s, 1H), 8.04 (s, 1H), 7.71 (d, J=7.2 Hz, 1H), 7.57 (d, J=6.2 Hz, 1H), 7.33-7.47 (m, 4H), 6.94 (d, J=8.7 Hz, 1H), 5.40 (br s, 2H), 4.38 (br s, 1H), 4.25 (d, J=7.4 Hz, 1H), 3.97 (br s, 1H), 3.25-3.41 (m, 2H), 2.92-3.06 (m, 2H), 2.06-2.22 (m, 2H), 1.65-1.80 (m, 5H), 1.36-1.55 (m, 3H), 1.07-1.33 (m, 3H), 0.79-1.03 (m, 2H). MS (m/z) 611.8 (M+1), 609.7 (M−1). HPLC=>99% at 20.45 minutes.

3-{1-[8-(2-Chlorophenyl)-9-(4-chlorophenyl)-9H-purin-6-yl]piperidin-4-yl}-1-phenylurea (18). The title compound was prepared by the general procedure D to provide 29 mg (47%) of a tan crystalline solid, mp 160-162° C. $R_f$=0.37 (2% MeOH/60% EtOAc/Hexanes; blue with UV). $^1$H NMR (300 MHz, $CDCl_3$) δ 8.36 (s, 1H), 7.49 (d, J=6.4 Hz, 1H), 7.08-7.42 (m, 11H), 6.91-7.05 (m, 2H), 5.32 (br s, 2H), 5.01-5.19 (m, 1H), 3.91-4.10 (m, 1H), 3.26 (br s, 2H), 1.96-2.21 (m, 2H), 1.30-1.48 (m, 2H). MS (m/z) 558.3 (M+1). HPLC=100% at 20.21 minutes.

3-{1-[8-(2-Chlorophenyl)-9-(4-chlorophenyl)-9H-purin-6-yl]piperidin-4-yl}-1-(2-fluorophenyl)urea (19). The title compound was prepared by the general procedure G to provide 55 mg (80%) of an off white amorphous solid, mp 152-154° C. $R_f$=0.50 (2% MeOH/60% EtOAc/Hexanes; blue with UV). $^1$H NMR (300 MHz, $CDCl_3$) δ 8.37 (s, 1H), 8.00 (t, J=7.8 Hz, 1H), 7.50 (d, J=6.6 Hz, 1H), 7.23-7.43 (m, 5H), 7.18 (d, J=8.1 Hz, 2H), 6.84-7.12 (m, 4H), 5.26-5.39 (m, 3H), 3.95-4.13 (m, 1H), 3.19-3.44 (m, 2H), 1.97-2.24 (m, 2H), 1.35-1.50 (m, 2H). MS (m/z) 576.2 (M+1). HPLC=>98% at 20.09 minutes.

3-{1-[8-(2-Chlorophenyl)-9-[6-(trifluoromethyl)pyridin-3-yl]-9H-purin-6-yl]piperidin-4-yl}-1-(2-fluorophenyl)urea (20). The title compound was prepared by the general procedure D to provide 63 mg (100%) of an off white amorphous solid, mp 227-228° C. $R_f$=0.17 (40% EtOAc/Hexanes; blue with UV). $^1$H NMR (300 MHz, $CDCl_3$) δ 8.50 (s, 1H), 8.36 (s, 1H), 7.86-8.12 (m, 2H), 7.75 (d, J=8.1 Hz, 1H), 7.62 (d, J=5.6 Hz, 1H), 7.30-7.51 (m, 3H), 6.80-7.15 (m, 4H), 5.24-5.38 (m, 3H), 3.90-4.22 (m, 1H), 3.33 (br s, 2H), 2.06-2.21 (m, 2H), 1.38-1.54 (m, 2H). MS (m/z) 611.5 (M+1), 609.9 (M−1). HPLC=>99% at 19.89 minutes.

3-{1-[8-(2-Chlorophenyl)-9-[6-(difluoromethoxy)pyridin-3-yl]-9H-purin-6-yl]piperidin-4-yl}-1-(2-fluorophenyl)urea (21). The title compound was prepared by the general procedure D to provide 62 mg (100%) of an off white amorphous solid, mp 140-142° C. $R_f$=0.14 (40% EtOAc/Hexanes; blue with UV). $^1$H NMR (300 MHz, $CDCl_3$) δ 8.35 (s, 1H), 7.90-8.15 (m, 2H), 7.69 (d, J=7.0 Hz, 1H), 7.56 (d, J=6.2 Hz, 1H), 7.29-7.48 (m, 4H), 6.80-7.17 (m, 5H), 5.25-5.45 (m, 3H), 3.90-4.12 (m, 1H), 3.25-3.39 (m, 2H), 2.04-2.27 (m, 2H), 1.35-1.52 (m, 2H). MS (m/z) 610.0 (M+1), 607.7 (M−1). HPLC=>99% at 19.51 minutes.

3-{1-[8-(2-Chlorophenyl)-9-(4-chlorophenyl)-9H-purin-6-yl]piperidin-4-yl}-1-(2,4-difluorophenyl)urea (22). The title compound was prepared by the general procedure G to provide 55 mg (77%) of an off white amorphous solid, mp 140-142° C. $R_f$=0.46 (2% MeOH/60% EtOAc/Hexanes; blue with UV). $^1$H NMR (300 MHz, $CDCl_3$) δ 8.35 (s, 1H), 7.84-7.98 (m, 1H), 7.49 (d, J=6.4 Hz, 1H), 7.23-7.43 (m, 5H), 7.17 (d, J=7.9 Hz, 2H), 6.97 (s, 1H), 6.65-6.86 (m, 2H), 5.46 (d, J=7.0 Hz, 1H), 5.32 (br s, 2H), 4.00 (br s, 1H), 3.32 (br s, 2H), 1.96-2.24 (m, 2H), 1.31-1.50 (m, 2H). MS (m/z) 594.3 (M+1). HPLC=>98% at 20.13 minutes.

3-{1-[8-(2-Chlorophenyl)-9-(4-chlorophenyl)-9H-purin-6-yl]piperidin-4-yl}-1-(4-fluorophenyl)urea (23). The title compound was prepared by the general procedure G to provide 21 mg (33%) of a tan crystalline solid, mp 215-217° C. $R_f$=0.33 (2% MeOH/60% EtOAc/Hexanes; blue with UV). $^1$H NMR (300 MHz, $CDCl_3$) δ 8.36 (s, 1H), 7.49 (d, J=6.4 Hz, 1H), 7.22-7.44 (m, 5H), 7.08-7.22 (m, 4H), 6.94 (t, J=8.5 Hz, 2H), 6.75 (s, 1H), 5.35 (br s, 2H), 4.89 (d, J=7.2 Hz, 1H), 3.92-4.10 (m, 1H), 3.22-3.36 (m, 2H), 1.97-2.23 (m, 2H), 1.34-1.48 (m, 2H). MS (m/z) 576.3 (M+1). HPLC=>98% at 19.79 minutes.

3-{1-[8-(2-Chlorophenyl)-9-(4-chlorophenyl)-9H-purin-6-yl]piperidin-4-yl}-1-[6-(trifluoromethyl)pyridin-3-yl]urea (24). The title compound was prepared by the general procedure G to provide 42 mg (56%) of an off white crystalline solid, mp 140-142° C. $R_f$=0.36 (2% MeOH/60% EtOAc/Hexanes; blue with UV). $^1$H NMR (300 MHz, $CDCl_3$-d) δ 8.37 (s, 1H), 8.34 (s, 1H), 8.22 (d, J=8.3 Hz, 1H), 7.59 (d, J=8.7 Hz, 1H), 7.49 (d, J=6.8 Hz, 1H), 7.27-7.42 (m, 6H), 7.17 (d, J=8.3 Hz, 2H), 5.25-5.50 (m, 2H), 5.03 (d, J=7.7 Hz, 1H), 3.95-4.20 (m, 1H), 3.29-3.46 (m, 2H), 2.05-2.24 (m, 2H), 1.33-1.54 (m, 2H). MS (m/z) 627.5 (M+1). HPLC=>99% at 19.88 minutes.

3-{1-[8-(2-Chlorophenyl)-9-(4-chlorophenyl)-9H-purin-6-yl]piperidin-4-yl}-1-[6-(difluoromethoxy)pyridin-3-yl]urea (25). The title compound was prepared by the general procedure G to provide 70 mg (93%) of an off white amorphous solid, mp 150-152° C. $R_f$=0.39 (2% MeOH/60% EtOAc/Hexanes; blue with UV). $^1$H NMR (300 MHz, $CDCl_3$) δ 8.36 (s, 1H), 7.94 (d, J=2.3 Hz, 1H), 7.85 (dd, J=8.8, 2.3 Hz, 1H), 7.49 (d, J=6.8 Hz, 1H), 7.23-7.44 (m, 6H), 7.16 (d, J=8.5 Hz, 2H), 7.03 (s, 1H), 6.81 (d, J=8.8 Hz, 1H), 5.20-5.52 (m, 2H), 4.99 (d, J=7.7 Hz, 1H), 3.88-4.05 (m, 1H), 3.24-3.40 (m, 2H), 2.03-2.25 (m, 2H), 1.31-1.55 (m, 2H). MS (m/z) 625.9 (M+1). HPLC=>99% at 19.68 minutes.

4-[8-(2-Chlorophenyl)-9-(4-chlorophenyl)-9H-purin-6-yl]-N-(3,4-difluorophenyl)piperazine-1-carboxamide (42). The title compound was prepared by the general procedure G to provide 39 mg (56%) an off white amorphous solid, mp 205-207° C. $R_f$=0.46 (2% MeOH/60% EtOAc/hexanes; blue with UV). $^1$H NMR (300 MHz, $CDCl_3$) δ 8.42 (s, 1H), 7.51 (d, J=6.6 Hz, 1H), 7.30-7.46 (m, 6H), 7.20 (d, J=8.5 Hz, 2H), 6.89-7.12 (m, 2H), 6.58 (s, 1H), 4.44 (br s, 4H), 3.68 (br s, 4H). MS (m/z) 580.4 (M+1). HPLC=>98% at 21.28 minutes.

4-[8-(2-Chlorophenyl)-9-(4-chlorophenyl)-9H-purin-6-yl]-N-(4-fluorophenyl)piperazine-1-carboxamide (43). The title compound was prepared by the general procedure G to provide 71 mg (100%) of an off white amorphous solid, mp 234-235° C. $R_f$=0.42 (2% MeOH/60% EtOAc/hexanes; blue with UV). $^1$H NMR (300 MHz, $CDCl_3$) δ 8.42 (s, 1H), 7.51 (d, J=6.22 Hz, 1H), 7.24-7.45 (m, 7H), 7.20 (d, J=8.1 Hz, 2H), 6.90-7.05 (m, 2H), 6.61 (s, 1H), 4.43 (br s, 4H), 3.67 (br s, 4H). MS (m/z) 561.9 (M+1). HPLC=>99% at 20.44 minutes.

4-[8-(2-Chlorophenyl)-9-(4-chlorophenyl)-9H-purin-6-yl]-N-[6-(difluoromethoxy)pyridin-3-yl]piperazine-1-carboxamide (44). The title compound was prepared by the general procedure G to provide 71 mg (100%) of an off white amorphous solid, mp 118-120° C. $R_f$=0.28 (2% MeOH/60% EtOAc/hexanes; blue with UV). $^1$H NMR (300 MHz, $CDCl_3$) δ 8.42 (s, 1H), 8.07 (d, J=2.3 Hz, 1H), 7.94 (dd, J=8.8, 2.5 Hz, 1H), 7.51 (d, J=7.0 Hz, 1H), 7.30-7.44 (m, 6H), 7.20 (d, J=8.5 Hz, 2H), 6.87 (d, J=8.8 Hz, 1H), 6.57 (s, 1H), 4.46 (br s, 4H), 3.60-3.85 (m, 4H). MS (m/z) 611.9 (M+1). HPLC=>99% at 20.59 minutes.

N-{1-[8-(2-Chlorophenyl)-9-[6-(trifluoromethyl)pyridin-3-yl]-9H-purin-6-yl]piperidin-4-yl}benzamide (45). The title compound was prepared by the general procedure D to provide 59 mg (85%) of an off white crystalline solid, mp 247-249° C. $R_f$=0.52 (2% MeOH/60% EtOAc/hexanes; blue with UV). $^1$H NMR (300 MHz, $CDCl_3$) δ 8.53 (s, 1H), 8.42 (s, 1H), 7.98 (d, J=6.8 Hz, 1H), 7.78 (d, J=8.3 Hz, 1H), 7.64 (d, J=5.2 Hz, 1H), 7.22-7.52 (m, 7H), 7.06 (t, J=6.8 Hz, 1H), 6.41 (s, 1H), 4.47 (br s, 4H), 3.62-3.84 (m, 4H). MS (m/z) 579.4 (M+1). HPLC=>99% at 20.16 minutes.

8-(2-Chlorophenyl)-6-{4-[(2-chlorophenyl)methyl]piperazin-1-yl}-9-[6-(difluoromethoxy)pyridin-3-yl]-9H-purine (46). The title compound was prepared by the general procedure F to provide 91 mg (78%) of a tan crystalline solid, mp 147-149° C. $R_f$=0.35 (40% EtOAc/hexanes; blue w UV). $^1$H NMR (300 MHz, $CDCl_3$) δ 8.37 (s, 1H), 8.05 (d, J=2.3 Hz, 1H), 7.72 (dd, J=8.7, 2.4 Hz, 1H), 7.15-7.66 (m, 9H), 6.94 (d, J=8.7 Hz, 1H), 4.40 (br s, 4H), 3.70 (s, 2H), 2.62-2.76 (m, J=4.7 Hz, 4H). MS (m/z) 582.5 (M+1). HPLC=>98% at 18.53 minutes.

8-(2-Chlorophenyl)-6-{4-[(2-chlorophenyl)methyl]piperazin-1-yl}-9-[6-(trifluoromethyl)pyridin-3-yl]-9H-purine (47). The title compound was prepared by the general procedure F to provide 114 mg (98%) of an off white crystalline solid, mp 189-190° C. $R_f$=0.40 (40% EtOAc/hexanes; blue with UV). $^1$H NMR (300 MHz, $CDCl_3$) δ 8.51 (s, 1H), 8.38 (s, 1H), 7.98 (d, J=7.4 Hz, 1H), 7.77 (d, J=8.3 Hz, 1H), 7.64 (d, J=5.1 Hz, 1H), 7.52 (d, J=6.6 Hz, 1H), 7.32-7.48 (m, 5H), 7.14-7.29 (m, 1H), 4.39 (br s, 4H), 3.70 (s, 2H), 2.69 (br s, 4H). MS (m/z) 584.5 (M+1). HPLC=>99% at 18.73 minutes.

4-[8-(2-chlorophenyl)-6-{4-[(2-chlorophenyl)methyl]piperazin-1-yl}-9H-purin-9-yl]benzamide (48). The title compound was prepared by the general procedure F to provide 88 mg (79%) of a brown tinted crystalline solid, mp 120-122° C. $R_f$=0.25 (2% MeOH/80% EtOAc/hexanes; blue with UV). $^1$H NMR (300 MHz, $CDCl_3$) δ 8.37 (s, 1H), 7.78 (d, J=7.9 Hz, 2H), 7.52 (d, J=6.2 Hz, 2H), 7.15-7.44 (m, 8H), 6.45 (br s, 2H), 4.40 (br s, 4H), 3.69 (s, 2H), 2.69 (br s, 4H). MS (m/z) 558.3 (M+1). HPLC=>99% at 15.41 minutes.

8-(2-chlorophenyl)-6-{4-[(2-chlorophenyl)methyl]piperazin-1-yl}-9-(5-methyl-1,2-oxazol-3-yl)-9H-purine (49). The title compound was prepared by the general procedure F to provide 46 mg (59%) of a tan amorphous solid, mp 79-81° C. $R_f$=0.33 (40% EtOAc/hexanes; blue with UV). $^1$H NMR (300 MHz, $CDCl_3$) δ 8.42 (s, 1H), 7.63 (d, J=6.2 Hz, 1H), 7.51 (d, J=6.8 Hz, 1H), 7.32-7.46 (m, 3H), 7.16-7.31 (m, 3H), 6.58 (s, 1H), 4.38 (br s, 4H), 3.69 (s, 3H), 2.68 (br s, 4H), 2.46 (s, 3H). MS (m/z) 520.5 (M+1). HPLC=>98% at 17.83 minutes.

4-[8-(2-chlorophenyl)-9-(4-chlorophenyl)-9H-purin-6-yl]-N-(1-methyl-1H-pyrazol-3-yl)piperazine-1-carboxamide (50). The title compound was prepared by the general procedure G to provide 48 mg (73%) of a white crystalline solid, mp 230-231° C. $R_f$=0.52 (40% EtOAc/hexanes; blue with UV). $^1$H NMR (300 MHz, $CDCl_3$) δ 8.42 (s, 1H), 7.50 (d, J=7.0 Hz, 1H), 7.31-7.46 (m, 6H), 7.20 (d, J=8.7 Hz, 2H), 4.45 (br s, 4H), 3.91 (br s, 2H), 3.83 (br s, 2H), 1.59 (s, 3H). MS (m/z) no TIC. HPLC=>98% at 21.63 minutes.

8-(2-Chlorophenyl)-6-{4-[(2-chlorophenyl)methyl]piperazin-1-yl}-9-(1-methyl-1H-pyrazol-3-yl)-9H-purine (51). The title compound was prepared by the general procedure F to provide 14 mg (18%) of a tan amorphous solid, mp 150-152° C. $R_f$=0.17 (2% MeOH/60% EtOAc/hexanes; blue with UV). $^1$H NMR (300 MHz, $CDCl_3$) δ 8.42 (s, 1H), 7.47-7.61 (m, 2H), 7.28-7.43 (m, 5H), 7.13-7.24 (m, 1H), 6.12-6.28 (m, 1H), 4.39 (br s, 2H), 3.83 (s, 3H), 3.69 (s, 2H), 2.68 (br s, 4H). MS (m/z) 519.4 (M+1). HPLC=>97% at 16.47 minutes.

4-[8-(2-Chlorophenyl)-9-(4-chlorophenyl)-9H-purin-6-yl]-N-(2-fluorophenyl)piperazine-1-carboxamide (56). The title compound was prepared by the general procedure G to provide 15 mg (22%) of an off white amorphous solid, mp 214-215° C. $R_f$=0.52 (2% MeOH/60% EtOAc/hexanes; blue with UV). $^1$H NMR (300 MHz, $CDCl_3$) δ 8.42 (s, 1H), 8.00-8.19 (m, 1H), 7.52 (d, J=6.8 Hz, 1H), 7.30-7.45 (m, 5H), 7.20 (d, J=8.5 Hz, 2H), 6.89-7.16 (m, 3H), 6.58-6.75 (m, 1H), 4.47 (br s, 4H), 3.60-3.86 (m, 4H). MS (m/z) 562.2 (M+1). HPLC=95% at 20.97 minutes.

4-[8-(2-Chlorophenyl)-9-(4-chlorophenyl)-9H-purin-6-yl]-N-(2,4-difluorophenyl)piperazine-1-carboxamide (57). The title compound was prepared by the general procedure E to provide 15 mg (22%) of an off white crystalline solid, mp 220-221° C. $R_f$=0.48 (2% MeOH/60% EtOAc/hexanes; blue with UV). $^1$H NMR (300 MHz, $CDCl_3$) δ 8.42 (s, 1H), 7.92-8.11 (m, 1H), 7.52 (d, J=6.6 Hz, 1H), 7.30-7.47 (m, 5H), 7.21 (d, J=8.3 Hz, 2H), 6.80-6.95 (m, 2H), 6.51 (s, 1H), 4.47 (br s, 4H), 3.71 (br s, 4H). MS (m/z) 580.4 (M+1). HPLC=>98% at 20.53 minutes.

tert-Butyl 4-[8-(2-Chlorophenyl)-9-(4-chlorophenyl)-9H-purin-6-yl]piperazine-1-carboxylate (58). The title compound was prepared by the general method A to provide 58 mg (80%). $^1$H NMR (300 MHz, $CDCl_3$) δ 8.40 (s, 1H), 7.47-7.56 (m, 1H), 7.30-7.43 (m, 5H), 7.20 (d, J=8.8 Hz, 2H), 4.35 (br s, 4H), 3.52-3.67 (m, 4H), 1.49 (s, 9H). MS (m/z) 525.5 (M+1).

4-{4-[8-(2-Chlorophenyl)-9-(4-chlorophenyl)-9H-purin-6-yl]piperazin-1-yl}phenol (59). The title compound was prepared by the general method A to provide 8.3 mg (6%). $^1$H NMR (300 MHz, $CDCl_3$) δ 8.41 (s, 1H), 7.49-7.56 (m, 1H), 7.29-7.42 (m, 5H), 7.16-7.24 (m, 2H), 6.86-6.96 (m, 2H), 6.73-6.83 (m, 2H), 4.53 (br s, 4H), 3.14-3.30 (m, 4H). MS (m/z) 517.6 (M+1).

8-(2-Chlorophenyl)-9-(4-chlorophenyl)-6-[4-(3-methoxyphenyl)piperazin-1-yl]-9H-purine (60). The title compound was prepared by the general method A to provide 77 mg (85%). $^1$H NMR (300 MHz, $CDCl_3$) δ 8.41 (s, 1H), 7.49-7.58 (m, 1H), 7.30-7.43 (m, 5H), 7.15-7.24 (m, 3H), 6.60 (dd, J=2.0, 8.0 Hz, 1H), 6.52 (t, J=2.3 Hz, 1H), 6.46 (dd, J=2.0, 8.0 Hz, 1H), 4.53 (br s, 4H), 3.80 (s, 3H), 3.29-3.42 (m, 4H), 1.58 (s, 2H). MS (m/z) 531.4 (M+1).

8-(2-Chlorophenyl)-9-(4-chlorophenyl)-6-[4-(2,3-dihydro-1,4-benzodioxin-2-ylcarbonyl)piperazin-1-yl]-9H-purine (61). The title compound was prepared by the general method C to provide 28 mg (19%). $^1$H NMR (300 MHz, $CDCl_3$) δ 8.43 (s, 1H), 7.47-7.57 (m, 1H), 7.31-7.45 (m, 5H), 7.16-7.24 (m, 2H), 6.80-6.98 (m, 4H), 4.89 (dd, J=2.5, 8.0 Hz, 1H), 4.60-4.82 (m, 2H), 4.54 (dd, J=2.5, 12.0 Hz, 1H), 4.37 (dd, J=8.0, 12.0 Hz, 2H), 4.01 (d, J=12.2 Hz, 2H), 3.58-3.82 (m, 2H). MS (m/z) 587.2 (M+1).

4-{4-[8-(2-Chlorophenyl)-9-(4-chlorophenyl)-9H-purin-6-yl]piperazin-1-yl}benzonitrile (62). The title compound was prepared by the general method A to provide 24 mg (30%). $^1$H NMR (300 MHz, $CDCl_3$) δ 8.43 (s, 1H), 7.47-7.59 (m, 3H), 7.28-7.46 (m, 5H), 7.14-7.24 (m, 2H), 6.91 (d, J=9.0 Hz, 2H), 4.53 (br s, 4H), 3.41-3.62 (m, 4H). MS (m/z) 526.3 (M+1).

3-{4-[8-(2-Chlorophenyl)-9-(4-chlorophenyl)-9H-purin-6-yl]piperazin-1-yl}phenol (63). The title compound was prepared by the general method A to provide 22 mg (33%). $^1$H NMR (300 MHz, $CDCl_3$) δ 8.42 (s, 1H), 7.50-7.57 (m, 1H), 7.30-7.45 (m, 5H), 7.17-7.24 (m, 2H), 7.13 (t, J=8.1 Hz, 1H), 6.56 (dd, J=1.9, 8.2 Hz, 1H), 6.43 (t, J=2.2 Hz, 1H), 6.35 (dd, J=2.0, 7.9 Hz, 1H), 5.11 (br s, 1H), 4.52 (br s, 4H), 3.24-3.43 (m, 4H). MS (m/z) 517.4 (M+1).

8-(2-Chlorophenyl)-9-(4-chlorophenyl)-6-[4-(2,4-dimethoxyphenyl)piperazin-1-yl]-9H-purine (64). The title compound was prepared by the general method A to provide 19 mg (14%). $^1$H NMR (300 MHz, $CDCl_3$) δ 8.41 (s, 1H), 7.49-7.57 (m, 1H), 7.30-7.45 (m, 6H), 7.14-7.24 (m, 2H), 6.88 (d, J=8.6 Hz, 1H), 6.51 (d, J=2.6 Hz, 1H), 6.44 (dd, J=2.7, 8.7 Hz, 1H), 4.56 (br s, 4H), 3.87 (s, 3H), 3.79 (s, 3H), 3.04-3.28 (m, 4H). MS (m/z) 561.3 (M+1).

6-{4-[4-(Benzyloxy)phenyl]piperazin-1-yl}-8-(2-chlorophenyl)-9-(4-chlorophenyl)-9H-purine (65). The title compound was prepared by the general method A to provide 17 mg (11%). $^1$H NMR (300 MHz, $CDCl_3$) δ 8.41 (s, 1H), 7.50-7.57 (m, 1H), 7.28-7.47 (m, 10H), 7.15-7.24 (m, 2H), 6.94 (s, 4H), 5.03 (s, 2H), 4.53 (br s, 4H), 3.18-3.29 (m, 4H). MS (m/z) 607.6 (M+1).

8-(2-Chlorophenyl)-9-(4-chlorophenyl)-6-(4-cyclohexylpiperazin-1-yl)-9H-purine (66). The title compound was prepared by the general method A to provide 25 mg (61%). $^1$H NMR (300 MHz, $CDCl_3$) δ 8.38 (s, 1H), 7.49-7.56 (m, 1H), 7.29-7.43 (m, 5H), 7.15-7.24 (m, 2H), 4.37 (br s, 4H), 2.63-2.83 (m, 4H), 2.32 (br s, 1H), 1.71-1.97 (m, 4H), 1.64 (d, J=11.7 Hz, 1H), 1.04-1.33 (m, 5H). MS (m/z) 507.1 (M+1).

8-(2-Chlorophenyl)-9-(4-chlorophenyl)-6-(4-pyridin-2-ylpiperazin-1-yl)-9H-purine (67). The title compound was prepared by the general method A to provide 31 mg (45%). $^1$H NMR (300 MHz, $CDCl_3$) δ 8.42 (s, 1H), 8.18-8.29 (m, 1H), 7.47-7.58 (m, 2H), 7.30-7.42 (m, 5H), 7.15-7.24 (m, 2H), 6.61-6.76 (m, 2H), 4.51 (br s, 4H), 3.66-3.82 (m, 4H). MS (m/z) 502.6 (M+1).

8-(2-Chlorophenyl)-9-(4-chlorophenyl)-6-[4-(2-fluorophenyl)piperazin-1-yl]-9H-purine (68). The title compound was prepared by the general method A to provide 50 mg (39%). $^1$H NMR (300 MHz, $CDCl_3$) δ 8.42 (s, 1H), 7.49-7.58 (m, 1H), 7.30-7.41 (m, 5H), 7.16-7.24 (m, 2H), 6.89-7.14 (m, 4H), 4.56 (br s, 4H), 3.17-3.34 (m, 4H). MS (m/z) 519.4 (M+1).

8-(2-Chlorophenyl)-9-(4-chlorophenyl)-6-[4-(1-phenylethyl)piperazin-1-yl]-9H-purine (69). The title compound was prepared by the general method A to provide 55 mg (49%). $^1$H NMR (300 MHz, $CDCl_3$) δ 8.36 (s, 1H), 7.44-7.55 (m, 1H), 7.27-7.40 (m, 9H), 7.13-7.22 (m, 2H), 4.35 (br s, 3H), 3.44 (q, J=6.7 Hz, 1H), 2.59 (ddt, J=5.0, 11.2, 16.5 Hz, 4H), 1.41 (d, J=6.7 Hz, 3H). MS (m/z) 529.7 (M+1).

8-(2-Chlorophenyl)-9-(4-chlorophenyl)-6-[4-(2-phenylethyl)piperazin-1-yl]-9H-purine (70). The title compound was prepared by the general method A to provide 56 mg (42%). $^1$H NMR (300 MHz, $CDCl_3$) δ 8.39 (s, 1H), 7.49-7.56 (m, 1H), 7.26-7.43 (m, 7H), 7.14-7.25 (m, 5H), 4.42 (br s, 4H), 2.80-2.94 (m, 2H), 2.60-2.77 (m, 6H). MS (m/z) 529.7 (M+1).

8-(2-Chlorophenyl)-9-(4-chlorophenyl)-6-[4-(2-methoxyphenyl)piperazin-1-yl]-9H-purine (71). The title compound was prepared by the general method A to provide 23 mg (17%). $^1$H NMR (300 MHz, $CDCl_3$) δ 8.41 (s, 1H), 7.49-7.59 (m, 1H), 7.30-7.41 (m, 5H), 7.17-7.24 (m, 2H), 7.00-7.09 (m, 1H), 6.85-6.99 (m, 3H), 4.57 (br s, 4H), 3.90 (s, 3H), 3.14-3.31 (m, 4H). MS (m/z) 531.5 (M+1).

8-(2-Chlorophenyl)-9-(4-chlorophenyl)-6-[4-(4-methoxyphenyl)piperazin-1-yl]-9H-purine (72). The title compound was prepared by the general method A to provide 23 mg (42%). $^1$H NMR (300 MHz, $CDCl_3$) δ 8.41 (s, 1H), 7.48-7.60 (m, 1H), 7.30-7.44 (m, 5H), 7.16-7.24 (m, 2H), 6.91-7.02 (m, 2H), 6.80-6.91 (m, 2H), 4.54 (br s, 4H), 3.78 (s, 3H), 3.13-3.34 (m, 4H). MS (m/z) 531.4 (M+1).

8-(2-Chlorophenyl)-9-(4-chlorophenyl)-6-[4-(2-chlorophenyl)piperazin-1-yl]-9H-purine (73). The title compound was prepared by the general method A to provide 67 mg (50%). $^1$H NMR (300 MHz, $CDCl_3$) δ 8.42 (s, 1H), 7.50-7.58 (m, 1H), 7.30-7.45 (m, 6H), 7.16-7.25 (m, 3H), 6.96-7.11 (m, 2H), 4.57 (br s, 4H), 3.13-3.33 (m, 4H). MS (m/z) 537.1 (M+1).

2-{4-[8-(2-Chlorophenyl)-9-(4-chlorophenyl)-9H-purin-6-yl]piperazin-1-yl}benzonitrile (74). The title compound was prepared by the general method A to provide 59 mg (54%). $^1$H NMR (300 MHz, $CDCl_3$) δ 8.42 (s, 1H), 7.60 (dd, J=1.5, 7.9 Hz, 1H), 7.46-7.57 (m, 2H), 7.29-7.44 (m, 5H), 7.16-7.25 (m, 2H), 6.98-7.11 (m, 2H), 4.60 (br s, 4H), 3.26-3.48 (m, 4H). MS (m/z) 526.5 (M+1).

6-[4-(2-Cyanobenzyl)piperazin-1-yl]-8-(2-chlorophenyl)-9-(4-chlorophenyl)-9H-purine (75). The title compound was prepared by the general method A to provide 125 mg (92%) of a solid, mp 127-128° C. $^1$H NMR (300 MHz, $CDCl_3$) δ 8.38 (s, 1H), 7.66 (d, J=7.8 Hz, 1H), 7.56-7.63 (m, 2H), 7.46-7.53 (m, 1H), 7.29-7.43 (m, 6H), 7.13-7.25 (m, 2H), 4.40 (br s, 4H), 3.77 (s, 2H), 2.68 (t, J=4.9 Hz, 4H). MS (m/z) 540.2 (M+1).

8-(2-Chlorophenyl)-9-(4-chlorophenyl)-6-(4-phenylpiperazin-1-yl)-9H-purine (76). The title compound was prepared by the general method A to provide 54 mg (59%). $^1$H NMR (300 MHz, $CDCl_3$) δ 8.42 (s, 1H), 7.48-7.57 (m, 1H), 7.26-7.45 (m, 7H), 7.15-7.24 (m, 2H), 6.99 (d, J=7.91 Hz, 2H), 6.90 (t, J=7.3 Hz, 1H), 4.54 (br s, 4H), 3.25-3.47 (m, 4H). MS (m/z) 501.6 (M+1).

6-[4-(4-Chlorobenzyl)piperazin-1-yl]-8-(2-chlorophenyl)-9-(4-chlorophenyl)-9H-purine (77). The title compound was prepared by the general method A to provide 37 mg (28%). $^1$H NMR (300 MHz, $CDCl_3$) δ 8.42 (s, 1H), 7.48-7.57 (m, 1H), 7.30-7.42 (m, 5H), 7.15-7.26 (m, 4H), 6.83-6.95 (m, 2H), 4.53 (br s, 4H), 3.24-3.41 (m, 4H). MS (m/z) 537.2 (M+1).

8-(2-Chlorophenyl)-9-(4-chlorophenyl)-6-[4-(ethylsulfonyl)piperazin-1-yl]-9H-purine (78). The title compound was prepared by the general method C to provide 7.0 mg (14%). $^1$H NMR (300 MHz, $CDCl_3$) δ 8.41 (s, 1H), 7.46-7.55 (m, 1H), 7.30-7.45 (m, 5H), 7.14-7.23 (m, 2H), 4.48 (br s, 4H), 3.37-3.56 (m, 4H), 2.99 (q, J=7.4 Hz, 2H), 1.80 (br s, 1H), 1.40 (t, J=7.4 Hz, 3H). MS (m/z) 517.4 (M+1).

8-(2-Chlorophenyl)-9-(4-chlorophenyl)-6-[4-(propylsulfonyl)piperazin-1-yl]-9H-purine (79). The title compound was prepared by the general method C to provide 6.1 mg (11%). $^1$H NMR (300 MHz, $CDCl_3$) δ 8.41 (s, 1H), 7.47-7.55 (m, 1H), 7.30-7.45 (m, 5H), 7.14-7.23 (m, 2H), 4.49 (br s, 4H), 3.37-3.53 (m, 4H), 2.84-2.98 (m, 2H), 1.79-1.98 (m, 3H), 1.06 (t, J=7.4 Hz, 3H). MS (m/z) 531.3 (M+1).

8-(2-Chlorophenyl)-9-(4-chlorophenyl)-6-{4-[(1-methylethyl)sulfonyl]piperazin-1-yl}-9H-purine (80). The title compound was prepared by the general method C to provide 3.9 mg (7%). $^1$H NMR (300 MHz, $CDCl_3$) δ 8.41 (s, 1H), 7.47-7.56 (m, 1H), 7.31-7.45 (m, 6H), 7.16-7.23 (m, 2H), 4.46 (br s, 4H), 3.50-3.61 (m, 4H), 3.23 (quin, J=6.8 Hz, 1H), 1.82 (br s, 2H), 1.37 (d, J=6.8 Hz, 6H). MS (m/z) 531.3 (M+1).

8-(2-Chlorophenyl)-9-(4-chlorophenyl)-6-[4-(butylsulfonyl)piperazin-1-yl]-9H-purine (81). The title compound was prepared by the general method C to provide 9.5 mg (17%). $^1$H NMR (300 MHz, $CDCl_3$) δ 8.41 (s, 1H), 7.47-7.56 (m, 1H), 7.30-7.45 (m, 5H), 7.13-7.24 (m, 2H), 4.49 (br s, 4H), 3.35-3.53 (m, 4H), 2.86-3.01 (m, 2H), 1.93 (br s, 1H), 1.73-1.88 (m, 2H), 1.45 (qd, J=7.4, 14.9 Hz, 2H), 0.95 (t, J=7.4 Hz, 3H). MS (m/z) 545.4 (M+1).

8-(2-Chlorophenyl)-9-(4-chlorophenyl)-6-{4-[(2-methylpropyl)sulfonyl]piperazin-1-yl}-9H-purine (82). The title compound was prepared by the general method C to provide 15 mg (27%). $^1$H NMR (300 MHz, $CDCl_3$) δ 8.41 (s, 1H), 7.46-7.54 (m, 1H), 7.30-7.45 (m, 5H), 7.14-7.23 (m, 2H), 4.49 (br s, 4H), 3.31-3.53 (m, 4H), 2.77 (d, J=6.6 Hz, 2H), 2.32 (quind, J=6.7, 13.4 Hz, 1H), 1.96 (br s, 1H), 1.12 (qd, J=6.7 Hz, 6H). MS (m/z) 545.5 (M+1).

8-(2-Chlorophenyl)-9-(4-chlorophenyl)-6-[4-(cyclopropylsulfonyl)piperazin-1-yl]-9H-purine (84). The title compound was prepared by the general method C to provide 18 mg (34%). $^1$H NMR (300 MHz, $CDCl_3$) δ 8.41 (s, 1H), 7.48-7.54 (m, 1H), 7.30-7.46 (m, 5H), 7.14-7.24 (m, 2H), 4.50 (br s, 4H), 3.38-3.56 (m, 4H), 2.27 (tt, J=4.8, 8.0 Hz, 1H), 1.93 (br s, 1H), 1.15-1.22 (m, 2H), 0.93-1.04 (m, 2H). MS (m/z) 529.5 (M+1).

8-(2-Chlorophenyl)-9-(4-chlorophenyl)-6-[4-(methylsulfonyl)piperazin-1-yl]-9H-purine (86). The title compound was prepared by the general method C to provide 10 mg (20%). $^1$H NMR (300 MHz, $CDCl_3$) δ 8.41 (s, 1H), 7.47-7.56 (m, 1H), 7.30-7.46 (m, 5H), 7.15-7.24 (m, 2H), 4.52 (br s, 4H), 3.31-3.48 (m, 4H), 2.81 (s, 3H). MS (m/z) 503.3 (M+1).

8-(2-Chlorophenyl)-9-(4-chlorophenyl)-6-[4-(trifluoroacetyl)piperazin-1-yl]-9H-purine (87). The title compound was prepared by the general method C to provide 11 mg (21%). $^1$H NMR (300 MHz, $CDCl_3$) δ 8.43 (s, 1H), 7.47-7.55 (m, 1H), 7.30-7.43 (m, 5H), 7.15-7.24 (m, 2H), 4.46 (d, J=5.4 Hz, 4H), 3.71-3.95 (m, 4H), 1.96 (br s, 1H). MS (m/z) 521.4 (M+1).

N-{1-[9-(4-Chlorophenyl)-8-(2,4-dichlorophenyl)-9H-purin-6-yl]-4-phenylpiperidin-4-yl}pentanamide (94). The title compound was prepared by the general method C to provide 68 mg (57%). $^1$H NMR (300 MHz, $CDCl_3$) δ 8.40 (s, 1H), 7.48-7.55 (m, 1H), 7.30-7.44 (m, 5H), 7.20 (d, J=8.8 Hz, 2H), 4.37 (br s, 4H), 3.75 (s, 3H), 3.56-3.71 (m, 4H). MS (m/z) 483.3 (M+1).

6-(4-Acetylpiperazin-1-yl)-8-(2-chlorophenyl)-9-(4-chlorophenyl)-9H-purine (95). The title compound was prepared by the general method C to provide 92 mg (78%). $^1$H NMR (300 MHz, $CDCl_3$) δ 8.41 (s, 1H), 7.48-7.56 (m, 1H), 7.31-7.45 (m, 5H), 7.21 (d, J=8.8 Hz, 2H), 4.24-4.60 (m, 4H), 3.56-3.87 (m, 4H), 2.16 (s, 3H). MS (m/z) 467.4 (M+1).

8-(2-Chlorophenyl)-9-(4-chlorophenyl)-6-[4-(2-fluorobenzyl)piperazin-1-yl]-9H-purine (96). The title compound was prepared by the general method A to provide 94 mg (70%). $^1$H NMR (300 MHz, $CDCl_3$) δ 8.37 (s, 1H), 7.47-7.57 (m, 1H), 7.23-7.44 (m, 7H), 7.15-7.22 (m, 2H), 6.95-7.15 (m, 2H), 4.39 (br s, 4H), 3.66 (s, 2H), 2.65 (t, J=4.9 Hz, 4H). MS (m/z) 533.2 (M+1).

8-(2-Chlorophenyl)-9-(4-chlorophenyl)-6-[4-(4-fluorobenzyl)piperazin-1-yl]-9H-purine (97). The title compound was prepared by the general method A to provide 109 mg (82%). $^1$H NMR (300 MHz, $CDCl_3$) δ 8.38 (s, 1H), 7.47-7.55 (m, 1H), 7.27-7.42 (m, 7H), 7.16-7.24 (m, 2H), 7.01 (t, J=8.7 Hz, 2H), 4.38 (br s, 4H), 3.52 (s, 2H), 2.58 (t, J=4.9 Hz, 4H). MS (m/z) 533.4 (M+1).

6-[4-(2-Chlorobenzyl)piperazin-1-yl]-8-(2-chlorophenyl)-9-(4-chlorophenyl)-9H-purine (98). The title compound was prepared by the general method A to provide 113 mg (82%). $^1$H NMR (300 MHz, $CDCl_3$) δ 8.38 (s, 1H), 7.51 (d, J=6.8 Hz, 2H), 7.29-7.41 (m, 6H), 7.13-7.28 (m, 4H), 4.40 (br s, 4H), 3.69 (s, 2H), 2.68 (t, J=4.9 Hz, 4H). MS (m/z) 549.4 (M+1).

6-[4-(3-Chlorobenzyl)piperazin-1-yl]-8-(2-chlorophenyl)-9-(4-chlorophenyl)-9H-purine (99). The title compound was prepared by the general method A to provide 105 mg (77%). $^1$H NMR (300 MHz, $CDCl_3$) δ 8.38 (s, 1H), 7.45-7.56 (m, 1H), 7.28-7.41 (m, 6H), 7.13-7.25 (m, 5H), 4.39 (br s, 4H), 3.53 (s, 2H), 2.60 (t, J=4.9 Hz, 4H). MS (m/z) 549.2 (M+1).

8-(2-Chlorophenyl)-9-(4-chlorophenyl)-6-[4-(2-methylbenzyl)piperazin-1-yl]-9H-purine (100). The title compound was prepared by the general method A to provide 115 mg (87%). $^1$H NMR (300 MHz, $CDCl_3$) δ 8.38 (s, 1H), 7.45-7.56 (m, 1H), 7.25-7.42 (m, 6H), 7.09-7.23 (m, 5H), 4.36 (br s, 4H), 3.51 (s, 2H), 2.60 (t, J=4.9 Hz, 4H), 2.39 (s, 3H). MS (m/z) 529.6 (M+1).

8-(2-Chlorophenyl)-9-(4-chlorophenyl)-6-[4-(4-methylbenzyl)piperazin-1-yl]-9H-purine (101). The title compound was prepared by the general method A to provide 110 mg (83%). $^1$H NMR (300 MHz, $CDCl_3$) δ 8.37 (s, 1H), 7.45-7.56 (m, 1H), 7.27-7.41 (m, 5H), 7.07-7.25 (m, 6H), 4.38 (br s, 4H), 3.53 (s, 2H), 2.59 (t, J=4.9 Hz, 4H), 2.33 (s, 3H). MS (m/z) 529.7 (M+1).

8-(2-Chlorophenyl)-9-(4-chlorophenyl)-6-[4-(4-methoxybenzyl)piperazin-1-yl]-9H-purine (102). The title compound was prepared by the general method A to provide 102 mg (75%). $^1$H NMR (300 MHz, $CDCl_3$) δ 8.37 (s, 1H), 7.45-7.56 (m, 1H), 7.28-7.42 (m, 5H), 7.25 (d, J=8.1 Hz, 2H), 7.19 (d, J=8.8 Hz, 2H), 6.86 (d, J=8.6 Hz, 2H), 4.37 (br s, 4H), 3.80 (s, 3H), 3.51 (s, 2H), 2.59 (t, J=4.9 Hz, 4H). MS (m/z) 545.5 (M+1).

8-(2-Chlorophenyl)-9-(4-chlorophenyl)-6-(4-pentanoylpiperazin-1-yl)-9H-purine (103). The title compound was prepared by the general method C to provide 78 mg (61%). $^1$H NMR (300 MHz, $CDCl_3$) δ 8.41 (s, 1H), 7.47-7.56 (m, 1H), 7.30-7.45 (m, 5H), 7.15-7.25 (m, 2H), 4.19-4.71 (m, J=19.7 Hz, 4H), 3.57-3.89 (m, 4H), 2.34-2.45 (m, 2H), 1.66 (quin, J=7.6 Hz, 2H), 1.39 (qd, J=7.4, 14.9 Hz, 2H), 0.94 (t, J=7.4 Hz, 3H). MS (m/z) 509.4 (M+1).

8-(2-Chlorophenyl)-9-(4-chlorophenyl)-6-(4-pyridin-4-ylpiperazin-1-yl)-9H-purine (104). The title compound was prepared by the general method A to provide 59 mg (47%). $^1$H NMR (300 MHz, $CDCl_3$) δ 8.42 (s, 1H), 8.31 (d, J=6.4 Hz, 2H), 7.47-7.57 (m, 1H), 7.30-7.45 (m, 5H), 7.21 (d, J=8.8 Hz, 2H), 6.71 (d, J=6.5 Hz, 2H), 4.52 (br s, 4H), 3.38-3.70 (m, 4H). MS (m/z) 502.6 (M+1).

8-(2-Chlorophenyl)-9-(4-chlorophenyl)-6-[4-(pyridin-4-ylmethyl)piperazin-1-yl]-9H-purine (105). The title compound was prepared by the general method A to provide 106 mg (82%). $^1$H NMR (300 MHz, $CDCl_3$) δ 8.56 (d, J=5.8 Hz, 2H), 8.38 (s, 1H), 7.47-7.56 (m, 1H), 7.26-7.42 (m, 7H), 7.14-7.23 (m, 2H), 4.40 (br s, 4H), 3.57 (s, 2H), 2.61 (t, J=4.9 Hz, 4H). MS (m/z) 516.4 (M+1).

8-(2-Chlorophenyl)-9-(4-chlorophenyl)-6-[4-(1-pyridin-4-ylethyl)piperazin-1-yl]-9H-purine (106). The title compound was prepared by the general method A to provide 71 mg (54%). $^1$H NMR (300 MHz, $CDCl_3$) δ 8.55 (d, J=6.0 Hz, 2H), 8.37 (s, 1H), 7.44-7.53 (m, 1H), 7.25-7.42 (m, 7H), 7.13-7.23 (m, 2H), 4.37 (br s, 4H), 3.45 (q, J=6.7 Hz, 1H), 2.45-2.73 (m, 4H), 1.38 (d, J=6.7 Hz, 3H). MS (m/z) 530.6 (M+1).

8-(2-Chlorophenyl)-9-(4-chlorophenyl)-6-[4-(2-pyridin-4-ylethyl)piperazin-1-yl]-9H-purine (107). The title compound was prepared by the general method A to provide 39 mg (30%). $^1$H NMR (300 MHz, $CDCl_3$) δ 8.41 (s, 1H), 7.49-7.59 (m, 1H), 7.30-7.41 (m, 5H), 7.17-7.24 (m, 2H), 7.00-7.09 (m, 1H), 6.85-6.99 (m, 3H), 4.57 (br s, 4H), 3.90 (s, 3H), 3.14-3.31 (m, 4H). MS (m/z) 530.6 (M+1).

8-(2-Chlorophenyl)-9-(4-chlorophenyl)-6-[4-(2-cyclohexylethyl)piperazin-1-yl]-9H-purine (108). The title compound was prepared by the general method A to provide 60 mg (46%). MS (m/z) 515.3 (M+1). $^1$H NMR (300 MHz, $CDCl_3$) δ 8.41 (s, 1H), 7.48-7.60 (m, 1H), 7.30-7.44 (m, 5H), 7.16-7.24 (m, 2H), 6.91-7.02 (m, 2H), 6.80-6.91 (m, 2H), 4.54 (br s, 4H), 3.78 (s, 3H), 3.13-3.34 (m, 4H).

8-(2-Chlorophenyl)-9-(4-chlorophenyl)-6-{4-[2-(trifluoromethyl)benzyl]piperazin-1-yl}-9H-purine (111). The title compound was prepared by the general method A to provide 102 mg (70%) of a solid, mp 119-121° C. $^1$H NMR (300 MHz, $CDCl_3$) δ 8.39 (s, 1H), 7.86 (d, J=7.8 Hz, 1H), 7.64 (d, J=7.8 Hz, 1H), 7.44-7.58 (m, 2H), 7.28-7.42 (m, 6H), 7.15-7.25 (m, 2H), 4.40 (br s, 4H), 3.73 (s, 2H), 2.65 (t, J=4.9 Hz, 4H). MS (m/z) 583.9 (M+1). HPLC=100% at 19.83 minutes.

8-(2-Chlorophenyl)-9-(4-chlorophenyl)-6-{4-[2-(trifluoromethoxy)benzyl]piperazin-1-yl}-9H-purine (112). The title compound was prepared by the general method A to provide 81 mg (54%) of a solid, mp 110-111° C. $^1$H NMR (300 MHz, $CDCl_3$) δ 8.38 (s, 1H), 7.54-7.66 (m, 1H), 7.45-7.54 (m, 1H), 7.23-7.43 (m, 8H), 7.15-7.22 (m, 2H), 4.39 (br s, 4H), 3.65 (s, 2H), 2.64 (t, J=4.9 Hz, 4H). $^{13}$C NMR (75 MHz, $CDCl_3$) δ 153.9, 153.2, 152.3, 148.0, 147.9, 145.6, 134.2, 134.2, 133.1, 132.5, 131.4, 131.1, 130.7, 130.0, 129.7, 129.4, 128.4, 128.0, 126.9, 126.7, 122.3, 120.6, 120.6, 119.7, 118.9, 56.0, 53.1, 45.3. $^{19}$F NMR (282 MHz, $CDCl_3$) δ−56.91. MS (m/z) 599.6 (M+1). HPLC=95% at 20.15 min.

8-(2-Chlorophenyl)-9-(4-chlorophenyl)-6-{4-[(1,5-dimethyl-1H-pyrazol-4-yl)methyl]piperazin-1-yl}-9H-purine (114). The title compound was prepared by the general method A to provide 144 mg (105%) of a solid, mp 138-139° C. $^1$H NMR (300 MHz, $CDCl_3$) δ 8.37 (s, 1H), 7.45-7.57 (m, 1H), 7.27-7.42 (m, 6H), 7.19 (d, J=8.7 Hz, 2H), 4.37 (br s, 4H), 3.77 (s, 3H), 3.41 (s, 2H), 2.57 (t, J=4.8 Hz, 4H), 2.24 (s, 3H). $^{13}$C NMR (75 MHz, $CDCl_3$) δ 153.8, 153.1, 152.2, 145.6, 139.2, 137.0, 134.2, 134.2, 133.1, 132.5, 131.4, 130.0, 129.6, 129.3, 128.0, 126.9, 119.7, 114.0, 52.7, 52.4, 45.3, 36.2, 9.6. MS (m/z) 533.3 (M+1). HPLC=99% at 17.99 min.

8-(2-Chlorophenyl)-9-(4-chlorophenyl)-6-{4-[(5-methyl-1,2,4-oxadiazol-3-yl)methyl]piperazin-1-yl}-9H-purine (115). The title compound was prepared by the general method A to provide 96 mg (74%) of a pale yellow film. $^1$H NMR (300 MHz, $CDCl_3$) δ 8.38 (s, 1H), 7.46-7.56 (m, 1H), 7.29-7.43 (m, 5H), 7.19 (d, J=8.7 Hz, 2H), 4.44 (br s, 4H), 3.74 (s, 2H), 2.74 (t, J=4.9 Hz, 4H), 2.60 (s, 3H). $^{13}$C NMR (75 MHz, $CDCl_3$) δ 176.8, 167.2, 153.8, 153.1, 152.3, 145.7, 134.2, 134.2, 133.0, 132.5, 131.4, 130.0, 129.6, 129.4, 128.0, 126.9, 119.7, 53.2, 52.9, 45.0, 12.3. MS (m/z) 521.4 (M+1). HPLC=99% at 17.88 min.

4-[8-(2-Chlorophenyl)-9-(4-chlorophenyl)-9H-purin-6-yl]-N-cyclopentylpiperazine-1-carboxamide (117). The title compound was prepared by the general procedure D to provide 51 mg (63%) of a white crystalline solid, mp 248-250° C. $R_f$=0.22 (1% MeOH/60% EtOAc/hexanes; blue with UV). $^1$H NMR (300 MHz, $CDCl_3$) δ 8.40 (s, 1H), 7.51 (d, J=6.8 Hz, 1H), 7.30-7.44 (m, 5H), 7.20 (d, J=8.7 Hz, 2H), 4.39 (d, J=6.2 Hz, 4H), 4.04-4.23 (m, 1H), 3.42-3.63 (m, 4H), 1.84-2.13 (m, 2H), 1.52-1.77 (m, 5H), 1.30-1.45 (m, 2H). MS (m/z) 536.2 (M+1). HPLC=100% at 20.85 minutes.

4-[8-(2-Chlorophenyl)-9-(4-chlorophenyl)-9H-purin-6-yl]-N-[1-(trifluoromethyl)cyclopentyl]piperazine-1-carboxamide (118). The title compound was prepared by the general procedure E to provide 36 mg (50%) of an off white crystalline solid, mp 202-204° C. $R_f$=0.47 (2% MeOH/60% EtOAc/hexanes; blue with UV). $^1$H NMR (300 MHz, $CDCl_3$) δ 8.40 (s, 1H), 7.51 (d, J=6.8 Hz, 1H), 7.31-7.43 (m, 5H), 7.20 (d, J=8.7 Hz, 2H), 4.50 (s, 1H), 4.40 (br s, 4H), 3.46-3.65 (m, 4H), 2.20-2.35 (m, 2H), 2.01-2.20 (m, 2H), 1.67-1.97 (m, 4H). MS (m/z) 604.4 (M+1). HPLC=99% at 21.64 minutes.

4-[8-(2-chlorophenyl)-9-(4-chlorophenyl)-9H-purin-6-yl]-N-cyclohexylpiperazine-1-carboxamide (119). The title compound was prepared by the general procedure G to provide 43 mg (65%) of a white crystalline solid, mp 228-229° C. $R_f$=0.31 (2% MeOH)/60% EtOAc/hexanes; blue with UV). $^1$H NMR (300 MHz, $CDCl_3$) δ 8.40 (s, 1H), 7.51 (d, J=6.8 Hz, 1H), 7.30-7.44 (m, 5H), 7.20 (d, J=8.7 Hz, 2H), 4.23-4.53 (m, 5H), 3.61-3.79 (m, 1H), 3.46-3.61 (m, 4H), 1.89-2.07 (m, 2H), 1.65-1.81 (m, 2H), 1.29-1.50 (m, 2H), 1.02-1.29 (m, 4H). MS (m/z) 550.4 (M+1). HPLC=100% at 21.49 minutes.

4-[8-(2-chlorophenyl)-9-(4-chlorophenyl)-9H-purin-6-yl]-N-(cyclohexylmethyl)piperazine-1-carboxamide (120). The title compound was prepared by the general procedure G to provide 44 mg (65%) of a white amorphous solid, mp 105-107° C. $R_f$=0.31 (2% MeOH)/60% EtOAc/hexanes; blue with UV). $^1$H NMR (300 MHz, $CDCl_3$) δ 8.40 (s, 1H), 7.51 (d, J=6.6 Hz, 1H), 7.29-7.45 (m, 5H), 7.20 (d, J=8.5 Hz, 2H), 4.61 (t, J=5.5 Hz, 1H), 4.33-4.45 (m, 4H), 3.56 (br s, 4H), 3.11 (dd, J=6.0, 6.0 Hz, 2H), 1.66-1.80 (m, 4H), 1.48 (m, 1H), 1.08-1.34 (m, 4H), 0.82-1.02 (m, 2H). MS (m/z) 564.2 (M+1). HPLC=100% at 22.32 minutes.

4-[8-(2-chlorophenyl)-9-(4-chlorophenyl)-9H-purin-6-yl]-N-phenylpiperazine-1-carboxamide (121). The title compound was prepared by the general procedure G to provide 67 mg (100%) of an off white amorphous solid, mp 121-123° C. $R_f$=0.43 (2% MeOH/60% EtOAc/hexanes; blue with UV). $^1$H NMR (300 MHz, $CDCl_3$) δ 8.42 (s, 1H), 7.51 (d, J=6.8 Hz, 1H), 7.23-7.44 (m, 9H), 7.20 (d, J=8.5 Hz, 2H), 6.96-7.11 (m, 1H), 6.61 (s, 1H), 4.43 (br s, 4H), 3.67 (br s, 4H). MS (m/z) 544.3 (M+1). HPLC=>99% at 20.36 minutes.

4-[8-(2-Chlorophenyl)-9-(4-chlorophenyl)-9H-purin-6-yl]-N-(pyridin-2-yl)piperazine-1-carboxamide (122). The title compound was prepared by the general procedure G to provide 65 mg (99%) of an off white amorphous solid, mp 120-122° C. $R_f$=0.25 (2% MeOH/60% EtOAc/hexanes; blue with UV). $^1$H NMR (300 MHz, $CDCl_3$) δ 8.42 (d, J=3.8 Hz, 1H), 8.21 (br s, 1H), 8.04 (d, J=8.3 Hz, 1H), 7.67 (t, J=7.4 Hz, 1H), 7.52 (d, J=6.4 Hz, 1H), 7.29-7.45 (m, 5H), 7.20 (d, J=8.3 Hz, 2H), 6.89-7.03 (m, 1H), 6.40-6.70 (m, 1H), 4.45 (br s, 4H), 3.74 (br s, 2H), 3.50 (br s, 2H). MS (m/z) 545.7 (M+1). HPLC=>97% at 18.15 minutes.

3-{1-[8-(2-Chlorophenyl)-9-(4-chlorophenyl)-9H-purin-6-yl]piperidin-4-yl}-1-(4,4-difluorocyclohexyl)urea (124). The title compound was prepared by the general procedure G to provide 72 mg (100%) of an off white amorphous solid, mp 228-229° C. $R_f$=0.21 (2% MeOH/60% EtOAc/Hexanes; blue with UV). $^1$H NMR (300 MHz, $CDCl_3$) δ 8.36 (s, 1H), 7.50 (d, J=6.8 Hz, 1H), 7.29-7.43 (m, 5H), 7.18 (d, J=8.5 Hz, 2H), 5.38 (br s, 1H), 4.35-4.53 (m, 2H), 3.83-4.04 (m, 1H), 3.62-3.81 (m, 1H), 3.23-3.42 (m, 2H), 1.67-2.22 (m, 8H), 1.32-1.59 (m, 4H). MS (m/z) 600.6 (M+1), 599.0 (M−1). HPLC=>99% at 19.41 minutes.

3-{1-[8-(2-Chlorophenyl)-9-(4-chlorophenyl)-9H-purin-6-yl]-4-methylpiperidin-4-yl}-1-(4,4-difluorocyclohexyl)urea (125). The title compound was prepared by the general procedure G to provide 71 mg (97%) of an off white amorphous solid, mp 175-177° C. $R_f$=0.21 (2% MeOH/60% EtOAc/Hexanes; blue with UV). $^1$H NMR (300 MHz, $CDCl_3$) δ 8.37 (s, 1H), 7.50 (d, J=6.8 Hz, 1H), 7.30-7.43 (m, 5H), 7.19 (d, J=8.7 Hz, 2H), 4.75 (br s, 2H), 4.27 (d, J=7.7 Hz, 1H), 4.20 (s, 1H), 3.87 (br s, 1H), 3.70 (br s, 2H), 2.10-2.23 (m, 2H), 1.82-2.08 (m, 4H), 1.68-1.80 (m, 4H), 1.34-1.50 (m, 5H). HPLC=>99% at 15.02 minutes.

3-{1-[8-(2-Chlorophenyl)-9-(4-chlorophenyl)-9H-purin-6-yl]piperidin-4-yl}-1-(4,4-difluoro-1-methylcyclohexyl)urea (126). The title compound was prepared by the general procedure G to provide 69 mg (94%) of an off white amorphous solid, mp 160-162° C. $R_f$=0.30 (2% MeOH/60% EtOAc/Hexanes; blue with UV). $^1$H NMR (300 MHz, $CDCl_3$) δ 8.36 (s, 1H), 7.50 (d, J=6.8 Hz, 1H), 7.29-7.44 (m, 5H), 7.18 (d, J=8.7 Hz, 2H), 5.38 (br s, 2H), 4.54 (d, J=7.9 Hz, 1H), 4.31 (s, 1H), 3.80-4.00 (m, 1H), 3.20-3.40 (m, 2H), 2.04-2.22 (m, 4H), 1.73-1.95 (m, 4H), 1.54-1.73 (m, 1H), 1.40-1.53 (m, 2H), 1.38 (s, 3H). HPLC=>99% at 15.10 minutes.

3-{1-[8-(2-Chlorophenyl)-9-(4-chlorophenyl)-9H-purin-6-yl]piperidin-4-yl}-1-[(4,4-difluorocyclohexyl)methyl]urea (127). The title compound was prepared by the general procedure G to provide 64 mg (87%) of an off white amorphous solid, mp 135-137° C. $R_f$=0.21 (2% MeOH/60% EtOAc/Hexanes; blue with UV). $^1$H NMR (300 MHz, $CDCl_3$) δ 8.37 (s, 1H), 7.50 (d, J=6.8 Hz, 1H), 7.29-7.44 (m, 5H), 7.18 (d, J=8.5 Hz, 2H), 5.39 (br s, 2H), 4.54 (t, J=5.8 Hz, 1H), 4.38 (d, J=7.9 Hz, 1H), 3.82-4.04 (m, 1H), 3.19-3.45 (m, 2H), 3.08 (dd, J=6.2, 6.2 Hz, 2H), 2.02-2.23 (m, 4H), 1.41-1.82 (m, 7H), 1.18-1.35 (m, 2H). HPLC=>99% at 14.70 minutes.

3-{1-[8-(2-Chlorophenyl)-9-(4-chlorophenyl)-9H-purin-6-yl]piperidin-4-yl}-1-[(4-fluorophenyl)methyl]urea (128). The title compound was prepared by the general procedure G to provide 71 mg (100%) of a white amorphous solid, mp 184-185° C. $R_f$=0.47 (2% MeOH/80% EtOAc/Hexanes; blue with UV). $^1$H NMR (300 MHz, $CDCl_3$) δ 8.35 (s, 1H), 7.50 (d, J=6.6 Hz, 1H), 7.26-7.44 (m, 5H), 7.12-7.24 (m, 4H), 6.86-7.06 (m, 2H), 5.33 (br s, 2H), 4.98 (br s, 1H), 4.66 (d, J=7.4 Hz, 1H), 4.27 (d, J=5.3 Hz, 2H), 3.93 (br s, 1H), 3.23-3.35 (m, 2H), 2.09 (br s, 2H), 1.30-1.49 (m, 2H). MS (m/z) 590.2 (M+1), 588.5 (M−1). HPLC=>99% at 19.72 minutes.

3-{1-[8-(2-Chlorophenyl)-9-(4-chlorophenyl)-9H-purin-6-yl]-4-methylpiperidin-4-yl}-1-[(2-fluorobenzene)sulfonyl]urea (129). To an ice-cold solution of 2-fluorophenylsulfonamide (42 mg, 2 equiv) in THF (1 mL), 1 M sodium bis(trimethylsilyl)amide/THF (0.26 mL, 2.2 equiv) was added drop-wise (precipitate formed). After 10 minutes, 4-nitrophenyl N-{1-[8-(2-chlorophenyl)-9-(4-chlorophenyl)-9H-purin-6-yl]-4-methylpiperidin-4-yl}carbamate (74 mg, 0.12 mmol; prepared by general procedure I) was added (turned yellow). After 10 minutes, the mixture was stirred at rt for 1 hour (turned orange). Brine (0.6 mL) was added, followed by 2 N HCl (0.18 mL, 3 equivs) and then ethyl acetate (3 mL). The mixture was stirred for 10 minutes and then the aqueous layer was removed. The organic layer was washed with brine (0.5 mL). Celite (600 mg) was added to the organic layer and the solvent was evaporated. Purification by flash chromatography provided 45 mg (58%) of the title compound as an off white amorphous solid, mp 111-113° C. $R_f$=0.44 (2% MeOH/60% EtOAc/Hexanes; blue with UV). $^1$H NMR (300 MHz, $CDCl_3$) δ 8.38 (s, 1H), 7.92

(t, J=7.2 Hz, 1H), 7.55-7.66 (m, 1H), 7.50 (d, J=6.6 Hz, 1H), 7.16-7.44 (m, 10H), 6.57 (s, 1H), 4.99 (br s, 2H), 3.46 (br s, 2H), 2.16 (d, J=13.8 Hz, 2H), 1.58-1.79 (m, 2H), 1.39 (s, 3H). MS (m/z) 654.5 (M+1), 652.6 (M−1). HPLC=96% at 15.05 minutes.

TABLE 1

Characterization of Selective Compounds

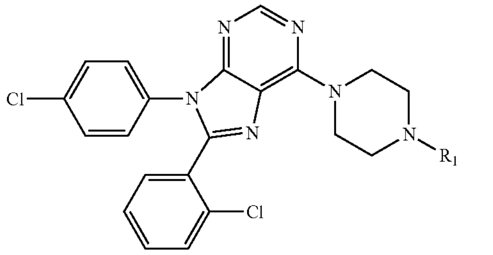

| $R_1$ | MF | MW | MS m/z | MP °C |
|---|---|---|---|---|
| 4-CN-2-Pyr | C27H20Cl2N8 | 527.41 | 527.8 | 244-246 |
| 4-F—Ph | C27H21Cl2FN6 | 519.40 | 519.6 | 180-182 |
| 4-tBoc-piperazine | C26H26Cl2N6O2 | 525.43 | 525.5 | 209-210 |
| 4-Hydroxyphenyl | C27H22Cl2N6O | 517.41 | 517.6 | 298-299 |
| 3-Methoxyphenyl | C28H24Cl2N6O | 531.44 | 531.4 | 171-172 |
| CO-2-(1,4-Benzodioxan) | C30H24Cl2N6O3 | 587.46 | 587.2 | 135-136 |
| 4-Cyanophenyl | C28H21Cl2N7 | 526.42 | 526.3 | 253-254 |
| 3-Hydroxyphenyl | C27H22Cl2N6O | 517.41 | 517.4 | 281-283 |
| 2,4-Dimethoxyphenyl | C29H26Cl2N6O2 | 561.46 | 561.3 | 188-189 |
| 1-Benzyloxyphenyl | C34H28Cl2N6O | 607.53 | 607.6 | 164-166 |
| 1-Cyclohexyl | C27H28Cl2N6 | 507.46 | 507.1 | 174-176 |
| 2-Pyridyl | C26H21Cl2N7 | 502.40 | 502.6 | 203-204 |
| 2-Fluorophenyl | C27H21Cl2FN6 | 519.40 | 519.4 | 211-212 |
| 1-Phenylethyl | C29H26Cl2N6 | 529.46 | 529.7 | 171-172 |
| 2-Phenylethyl | C29H26Cl2N6 | 529.46 | 5297 | 156-157 |

TABLE 1-continued

Characterization of Selective Compounds

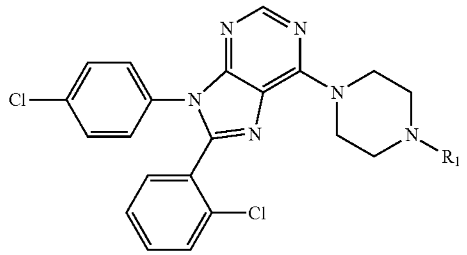

| $R_1$ | MF | MW | MS m/z | MP °C |
|---|---|---|---|---|
| 2-Methoxyphenyl | C28H24Cl2N6O | 531.44 | 531.5 | 177-179 |
| 4-Methoxyphenyl | C28H24Cl2N6O | 531.44 | 531.4 | 185-186 |
| 2-Chlorophenyl | C27H21Cl3N6 | 535.85 | 537.1 | 205-206 |
| 2-Cyanophenyl | C28H21Cl2N7 | 526.42 | 526.5 | 168-169 |
| Phenyl | C27H22Cl2N6 | 501.41 | 501.6 | 199-201 |
| 4-Chlorophenyl | C27H21Cl3N6 | 535.85 | 537.2 | 172-174 |
| $SO_2$—Et | C23H22Cl2N6O2S | 517.43 | 517.4 | 175-176 |
| $SO_2$—Pr | C24H24Cl2N6O2S | 531.46 | 531.3 | 211-212 |
| $SO_2$—iPr | C24H24Cl2N6O2S | 531.46 | 531.3 | 207-209 |
| $SO_2$—Bu | C25H26Cl2N6O2S | 545.48 | 545.4 | 182-184 |
| $SO_2$—iBu | C25H26Cl2N6O2S | 545.48 | 545.5 | 196-197 |
| $SO_2$—cPropyl | C24H22Cl2N6O2S | 529.44 | 529.5 | 202-204 |
| $SO_2$—Me | C22H20Cl2N6O2S | 503.40 | 503.3 | 159-161 |
| $COCF_3$ | C23H17Cl2F3N6O | 521.32 | 521.4 | 210-211 |
| 4-Methoxybenzyl | C29H26Cl2N6O | 545.46 | 545.5 | 138-139 |
| Butylamido | C26H26Cl2N6O | 509.43 | 509.4 | 114-116 |
| 4-Pyridyl | C26H21Cl2N7 | 502.40 | 502.6 | 155-157 |
| 4-Pyridylmethyl | C27H23Cl2N7 | 516.42 | 516.4 | 92-93 |
| 1-Pyridin-4-ylethyl | C28H25Cl2N7 | 530.45 | 530.6 | 105-107 |
| 2-Pyridin-4-ylethyl | C28H25Cl2N7 | 530.45 | 530.6 | 142-143 |
| 2-Cyclohexylethyl | C29H32Cl2N6 | 535.51 | 515.3 | 94-95 |

TABLE 2

Structures of CB1 Receptor Antagonists

| Cmd # | Structure | MF | Name |
|---|---|---|---|
| 1 | | C28H23Cl2FN6O2S | N-{1-[8-(2-Chloro-phenyl)-9-(4-chloro-phenyl)-9H-purin-6-yl]-piperidin-4-yl}-2-fluoro-benzene-1-sulfonamide |
| 2 | 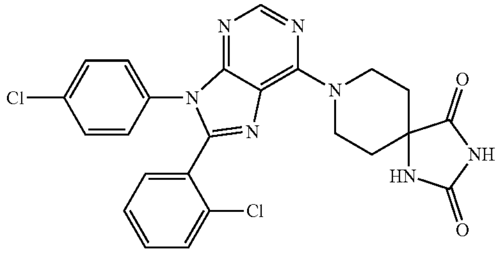 [SMILES: O=C1NC(=O)C2(CCN(c3ncnc4c3nc(-c3ccccc3Cl)n4-c3ccc(Cl)cc3)CC2)N1] | C24H19Cl2N7O2 | 8-[8-(2-chlorophenyl)-9-(4-chlorophenyl)-9H-purin-6-yl]-1,3,8-triazaspiro[4.5]decane-2,4-dione |

TABLE 2-continued

| Structures of CB1 Receptor Antagonists | | | |
|---|---|---|---|
| Cmd # | Structure | MF | Name |
| 3 | 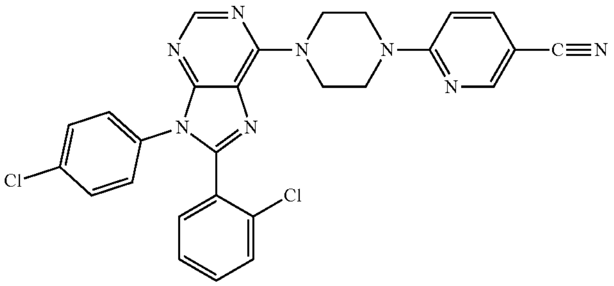 [SMILES: N#Cc1ccc(N2CCN(c3ncnc4c3nc(-c3ccccc3Cl)n4-c3ccc(Cl)cc3)CC2)nc1] | C27H20Cl2N8 | 6-{4-[8-(2-chloro-phenyl)-9-(4-chloro-phenyl)-9H-purin-6-yl]piperazin-1-yl}-pyridine-3-carbonitrile |
| 4 | | C28H23Cl2FN6O2S | N-{1-[8-(2-Chloro-phenyl)-9-(4-chloro-phenyl)-9H-purin-6-yl]piperidin-4-yl}-4-fluorobenzene-1-sulfonamide |
| 5 | | C28H22Cl2F2N6O2S | N-{1-[8-(2-Chloro-phenyl)-9-(4-chloro-phenyl)-9H-purin-6-yl]piperidin-4-yl}-2,4-difluorobenzene-1-sulfonamide |
| 6 | 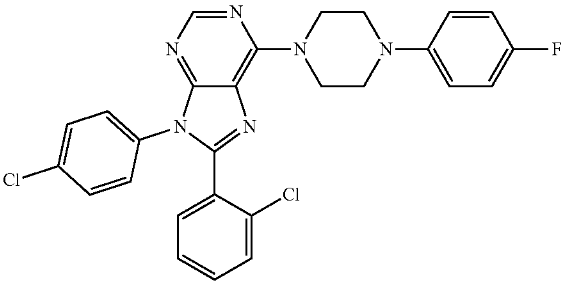 [SMILES: Fc1ccc(N2CCN(c3ncnc4c3nc(-c3ccccc3Cl)n4-c3ccc(Cl)cc3)CC2)cc1] | C27H21Cl2FN6 | 8-(2-chlorophenyl)-9-(4-chlorophenyl)-6-[4-(4-fluorophenyl)-piperazin-1-yl]-9H-purine |
| 7 | | C28H22Cl2F2N6O2S | N-{1-[8-(2-Chloro-phenyl)-9-(4-chloro-phenyl)-9H-purin-6-yl]piperidin-4-yl}-3,4-difluorobenzene-1-sulfonamide |
| 8 | | C28H22ClF4N7O3S | N-{1-[8-(2-Chloro-phenyl)-9-[6-(difluoro-methoxy)pyridin-3-yl]-9H-purin-6-piperidin-4-yl}-3,4-difluoro-benzene-1-sulfonamide |
| 9 | | C29H24ClF2N7O3S | 4-[8-(2-Chlorophenyl)-6-{4-[(3,4-difluoro-benzene)sulfonamido]-piperidin-1-yl}-9H-purin-9-yl]benzamide |
| 10 | | C28H21ClF5N7O2S | N-{1-[8-(2-Chloro-phenyl)-9-[6-(trifluoro-methyl)pyridin-3-yl]-9H-purin-6-yl]piperidin-4-yl}-3,4-difluoro-benzene-1-sulfonamide |
| 11 | | C26H22ClF2N7O3S | N-{1-[8-(2-Chloro-phenyl)-9-(5-methyl-1,2-oxazol-3-yl)-9H-purin-6-yl]piperidin-4-yl}-3,4-difluorobenzene-1-sulfonamide |
| 12 | | C26H23ClF2N8O2S | N-{1-[8-(2-Chloro-phenyl)-9-(1-methyl-1H-pyrazol-4-yl)-9H-purin-6-yl]piperidin-4-yl}-3,4-difluorobenzene-1-sulfonamide |

TABLE 2-continued

| Structures of CB1 Receptor Antagonists | | | |
|---|---|---|---|
| Cmd # | Structure | MF | Name |
| 13 | 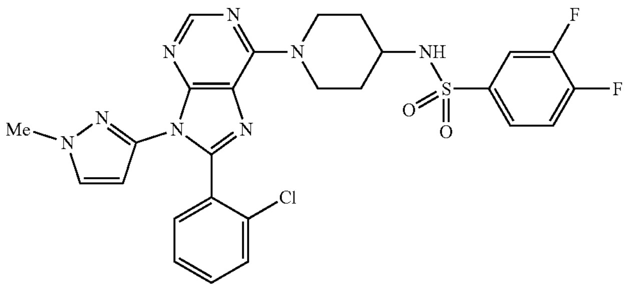 [SMILES: Cn1ccc(-n2c(-c3ccccc3Cl)nc3c(N4CCC(NS(=O)(=O)c5ccc(F)c(F)c5)CC4)ncnc32)n1] | C26H23ClF2N8O2S | N-{1-[8-(2-Chloro-phenyl)-9-(1-methyl-1H-pyrazol-3-yl)-9H-purin-6-yl]piperidin-4-yl}-3,4-difluoro-benzene-1-sulfonamide |
| 14 | 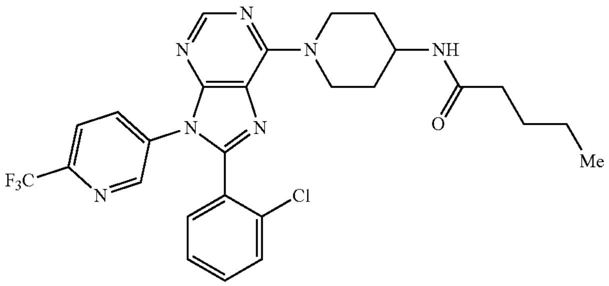 [SMILES: CCCCC(=O)NC1CCN(c2ncnc3c2nc(-c2ccccc2Cl)n3-c2ccc(C(F)(F)F)nc2)CC1] | C27H27ClF3N7O | N-{1-[8-(2-Chloro-phenyl)-9-[6-(trifluoro-methyl)pyridin-3-yl]-9H-purin-6-yl]piperidin-4-yl}pentanamide |
| 15 | 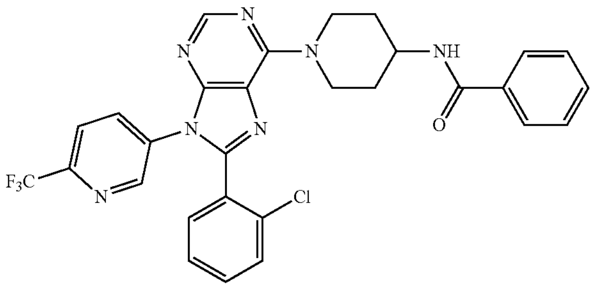 [SMILES: O=C(NC1CCN(c2ncnc3c2nc(-c2ccccc2Cl)n3-c2ccc(C(F)(F)F)nc2)CC1)c1ccccc1] | C29H23ClF3N7O | N-{1-[8-(2-Chloro-phenyl)-9-[6-(trifluoro-methyl)pyridin-3-yl]-9H-purin-6-yl]piperidin-4-yl}benzamide |
| 16 | 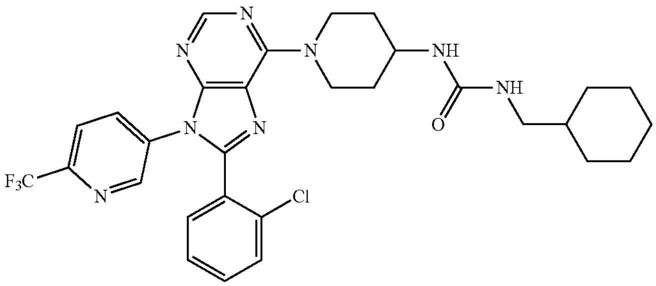 [SMILES: O=C(NCC1CCCCC1)NC1CCN(c2ncnc3c2nc(-c2ccccc2Cl)n3-c2ccc(C(F)(F)F)nc2)CC1] | C30H32ClF3N8O | 3-{1-[8-(2-Chloro-phenyl)-9-[6-(trifluoro-methyl)pyridin3-yl]-9H-purin-6-yl]piperidin-4-yl}-1-(cyclohexyl-methyl)urea |
| 17 | 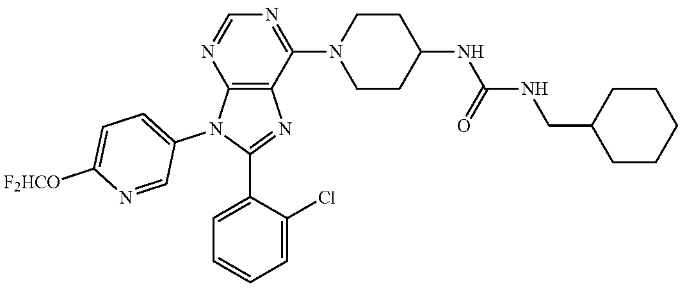 [SMILES: O=C(NCC1CCCCC1)NC1CCN(c2ncnc3c2nc(-c2ccccc2Cl)n3-c2ccc(OC(F)F)nc2)CC1] | C30H33ClF2N8O2 | 3-{1-[8-(2-Chloro-phenyl)-9-[6-(difluoro-methoxy)pyridin-3-yl]-9H-purin-6-yl]piperidin-4-yl}-1-(cyclohexyl-methyl)urea |

TABLE 2-continued

Structures of CB1 Receptor Antagonists

| Cmd # | Structure | MF | Name |
|---|---|---|---|
| 18 | 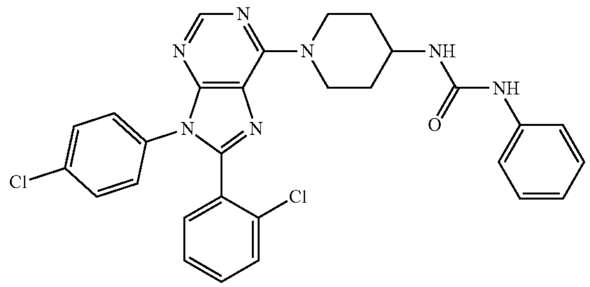 [SMILES: O=C(Nc1ccccc1)NC1CCN(c2ncnc3c2nc(-c2ccccc2Cl)n3-c2ccc(Cl)cc2)CC1] | C29H25Cl2N7O | 3-{1-[8-(2-Chloro-phenyl)-9-(4-chloro-phenyl)-9H-purin-6-yl]piperidin-4-yl}-1-phenylurea |
| 19 | 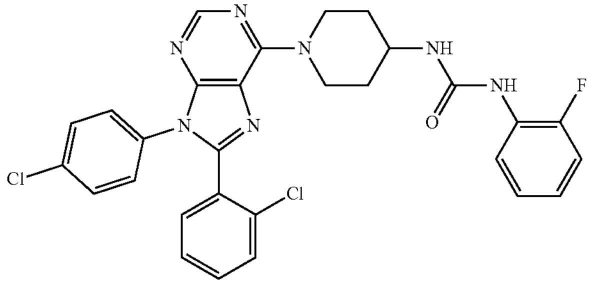 [SMILES: O=C(Nc1ccccc1F)NC1CCN(c2ncnc3c2nc(-c2ccccc2Cl)n3-c2ccc(Cl)cc2)CC1] | C29H24Cl2FN7O | 3-{1-[8-(2-Chloro-phenyl)-9-(4-chloro-phenyl)-9H-purin-6-yl]piperidin-4-yl}-1-(2-fluorophenyl)urea |
| 20 | 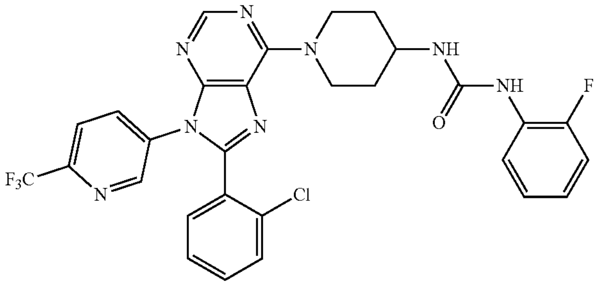 [SMILES: O=C(Nc1ccccc1F)NC1CCN(c2ncnc3c2nc(-c2ccccc2Cl)n3-c2ccc(C(F)(F)F)nc2)CC1] | C29H23ClF4N8O | 3-{1-[8-(2-Chloro-phenyl)-9-[6-(trifluoro-methyl)pyridin3-yl]-9H-purin-6-yl]piperidin-4-yl}-1-(2-fluorophenyl)-urea |
| 21 | 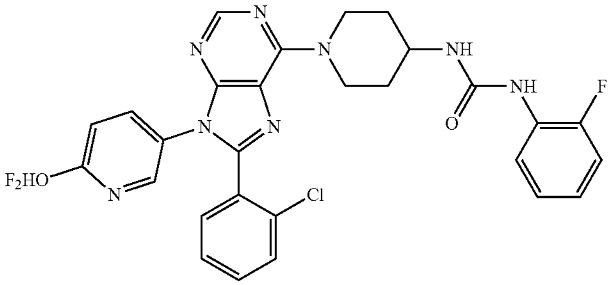 | C29H24ClF3N8O2 | Chlorophenyl)-9-(4-chlorophenyl)-9H-purin-6-yl]piperidin-4-yl}-1-(2,4-difluoro-phenyl)urea |
| 22 | 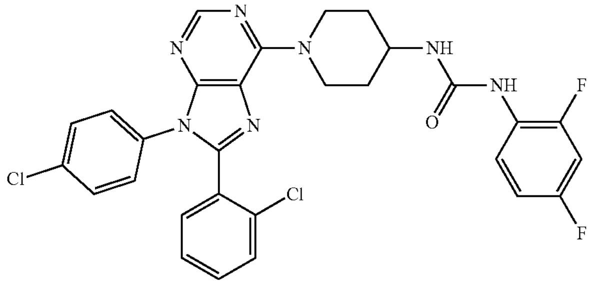 [SMILES: O=C(Nc1ccc(F)cc1F)NC1CCN(c2ncnc3c2nc(-c2ccccc2Cl)n3-c2ccc(Cl)cc2)CC1] | C29H23Cl2F2N7O | 3-{1-[8-(2-Chloro-phenyl)-9-[6-(difluoro-methoxy)pyridin-3-yl]-9H-purin-6-yl]-piperidin-4-yl}-1-(2-fluorophenyl)urea |

TABLE 2-continued

| Structures of CB1 Receptor Antagonists | | | |
|---|---|---|---|
| Cmd # | Structure | MF | Name |
| 23 | 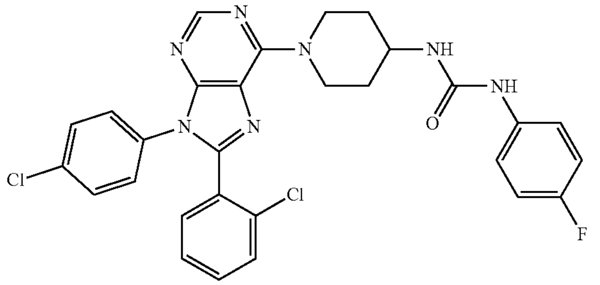 [SMILES: O=C(Nc1ccc(F)cc1)NC1CCN(c2ncnc3c2nc(-c2ccccc2Cl)n3-c2ccc(Cl)cc2)CC1] | C29H24Cl2FN7O | 3-{1-[8-(2-Chloro-phenyl)-9-(4-chloro-phenyl)-9H-purin-6-yl]piperidin-4-yl}-1-(4-fluorophenyl)urea |
| 24 | 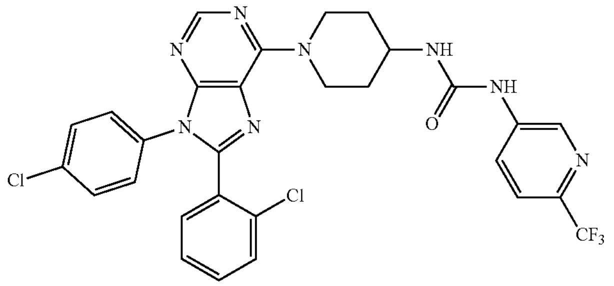 [SMILES: O=C(Nc1ccc(C(F)(F)F)nc1)NC1CCN(c2ncnc3c2nc(-c2ccccc2Cl)n3-c2ccc(Cl)cc2)CC1] | C29H23Cl2F3N8O | 3-{1-[8-(2-Chloro-phenyl)-9-(4-chloro-phenyl)-9H-purin-6-yl]piperidin-4-yl}-1-[6-(trifluoromethyl)-pyridin-3-yl)urea |
| 25 | 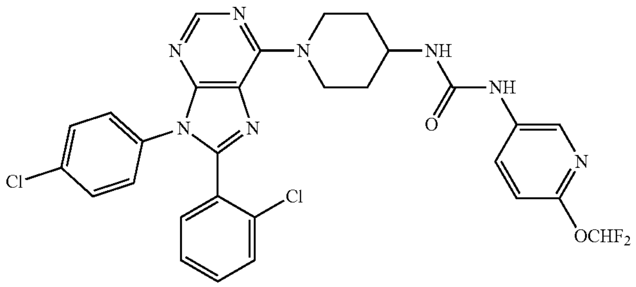 [SMILES: O=C(Nc1ccc(OC(F)F)nc1)NC1CCN(c2ncnc3c2nc(-c2ccccc2Cl)n3-c2ccc(Cl)cc2)CC1] | C29H24Cl2F2N8O2 | 3-{1-[8-(2-Chloro-phenyl)-9-(4-chloro-phenyl)-9H-purin-6-yl]piperidin-4-yl}-1-[6-(difluoromethoxy)-pyridin-3-yl)urea |
| 26 | 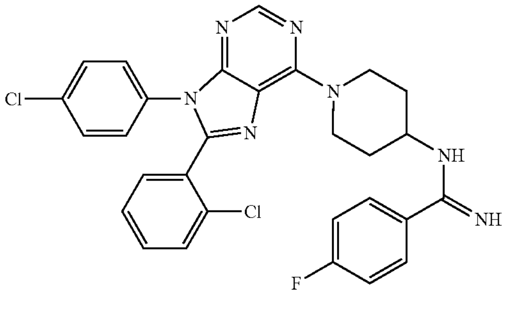 [SMILES: N=C(NC1CCN(c2ncnc3c2nc(-c2ccccc2Cl)n3-c2ccc(Cl)cc2)CC1)c1ccc(F)cc1] | C29H24Cl2F1N7 | N-{1-[8-(2-chloro-phenyl)-9-(4-chloro-phenyl)-9H-purin-6-yl]piperidin-4-yl}-4-fluorobenzenecarbox-imidamide |
| 27 | 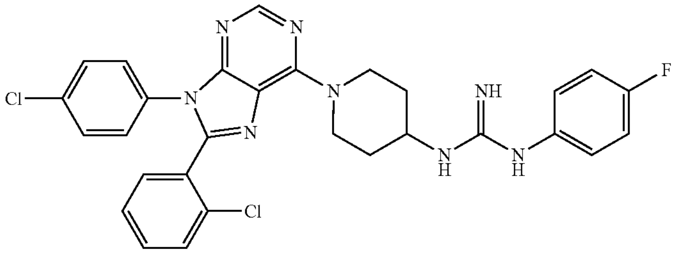 [SMILES: N=C(Nc1ccc(F)cc1)NC1CCN(c2ncnc3c2nc(-c2ccccc2Cl)n3-c2ccc(Cl)cc2)CC1] | C29H25Cl2F1N8 | 1-{1-[8-(2-chloro-phenyl)-9-(4-chloro-phenyl)-9H-purin-6-yl]piperidin-4-yl}-3-(4-fluorophenyl)-guanidine |

TABLE 2-continued

| Structures of CB1 Receptor Antagonists | | | |
|---|---|---|---|
| Cmd # | Structure | MF | Name |
| 28 | 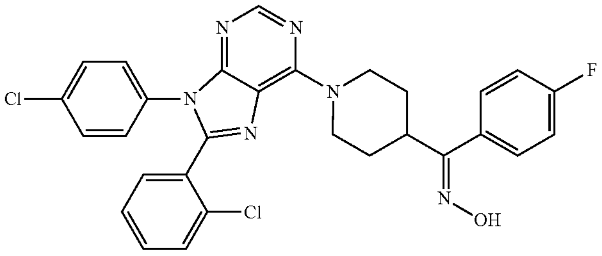 [SMILES: O/N=C(\c1ccc(F)cc1)C1CCN(c2ncnc3c2nc(-c2ccccc2Cl)n3-c2ccc(Cl)cc2)CC1] | C29H23F1N6O1 | (Z)-{1-[8-(2-chloro-phenyl)-9-(4-chloro-phenyl)-9H-purin-6-yl]-piperidin-4-yl}(4-fluoro-phenyl)methanone oxime |
| 29 | | C29H23F1N6O1 | (E)-{1-[8-(2-chloro-phenyl)-9-(4-chloro-phenyl)-9H-purin-6-yl]piperidin-4-yl}(4-fluorophenyl)-methanone oxime |
| 30 | | C29H23Cl2N7 | 6-[4-(1H-benzimidazol-2-yl)piperidin-1-yl]-8-(2-chlorophenyl)-9-(4-chlorophenyl)-9H-purine |
| 31 | | C28H24Cl2N6 | 1-[8-(2-chlorophenyl)-9-(4-chlorophenyl)-9H-purin-6-yl]-N-phenyl-piperidin-4-amine |
| 32 | | C27H23Cl2N7 | N-{1-[8-(2-chloro-phenyl)-9-(4-chloro-phenyl)-9H-purin-6-yl]piperidin-4-yl}-pyridin-2-amine |
| 33 | | C26H22Cl2N8 | N-{1-[8-(2-chloro-phenyl)-9-(4-chloro phenyl)-9H-purin-6-yl]piperidin-4-yl}-pyrimidin-2-amine |
| 34 | 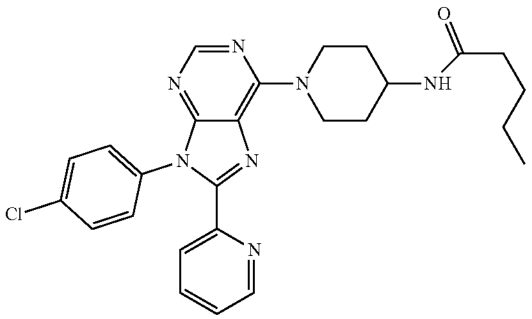 [SMILES: CCCCC(=O)NC1CCN(c2ncnc3c2nc(-c2ccccn2)n3-c2ccc(Cl)cc2)CC1] | C26H28ClN7O | N-{1-[9-(4-chloro-phenyl)-8-pyridin-2-yl-9H-purin-6-yl]-piperidin-4-yl}-pentanamide |
| 35 | 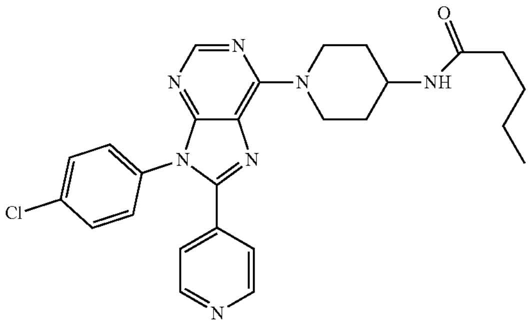 [SMILES: CCCCC(=O)NC1CCN(c2ncnc3c2nc(-c2ccncc2)n3-c2ccc(Cl)cc2)CC1] | C26H28ClN7O | N-{1-[9-(4-chloro-phenyl)-8-pyridin-4-yl-9H-purin-6-yl]-piperidin-4-yl}-pentanamide |
| 36 | | C27H23Cl2N7 | N-{1-[8-(2-chloro-phenyl)-9-(4-chloro phenyl)-9H-purin-6-yl]piperidin-4-yl}-pyridin-4-amine |

TABLE 2-continued

| Structures of CB1 Receptor Antagonists | | | |
|---|---|---|---|
| Cmd # | Structure | MF | Name |
| 37 | 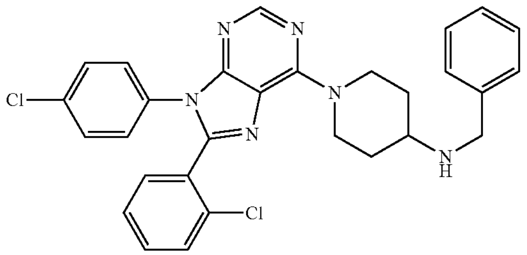 | C29H26Cl2N6 | N-benzyl-1-[8-(2-chlorophenyl)-9-(4-chlorophenyl)-9H-purin-6-yl]piperidin-4-amine |
| 38 | 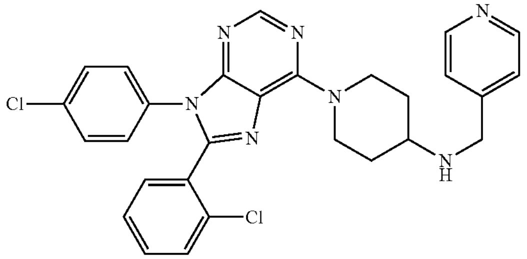 [SMILES: Clc1ccc(-n2c(-c3ccccc3Cl)nc3c(N4CCC(NCc5ccncc5)CC4)ncnc32)cc1] | C28H25Cl2N7 | 1-[8-(2-chlorophenyl)-9-(4-chlorophenyl)-9H-purin-6-yl]-N-(pyridin-4-ylmethyl)-piperidin-4-amine |
| 39 | 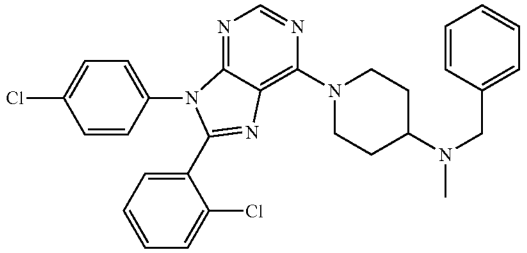 [SMILES: CN(Cc1ccccc1)C1CCN(c2ncnc3c2nc(-c2ccccc2Cl)n3-c2ccc(Cl)cc2)CC1] | C30H28Cl2N6 | N-benzyl-1-[8-(2-chlorophenyl)-9-(4-chlorophenyl)-9H-purin-6-yl]-N-methyl-piperidin-4-amine |
| 40 | 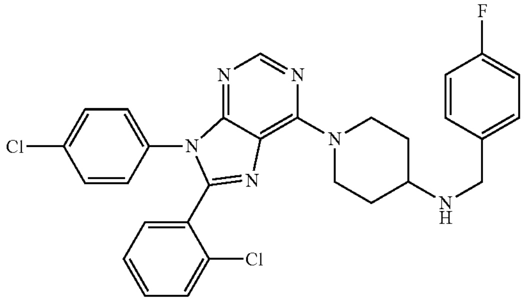 [SMILES: Fc1ccc(CNC2CCN(c3ncnc4c3nc(-c3ccccc3Cl)n4-c3ccc(Cl)cc3)CC2)cc1] | C29H25Cl2FN6 | 1-[8-(2-chlorophenyl)-9-(4-chlorophenyl)-9H-purin-6-yl]-N-(4-fluorobenzyl)piperidin-4-amine |
| 41 | 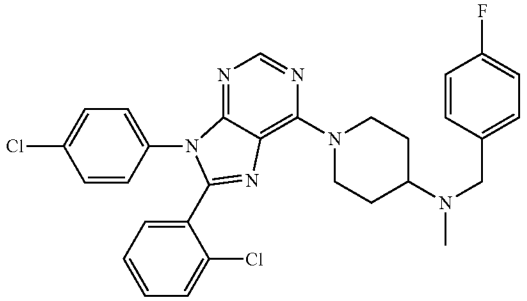 [SMILES: CN(Cc1ccc(F)cc1)C1CCN(c2ncnc3c2nc(-c2ccccc2Cl)n3-c2ccc(Cl)cc2)CC1] | C30H27Cl2FN6 | 1-[8-(2-chlorophenyl)-9-(4-chlorophenyl)-9H-purin-6-yl]-N-(4-fluorobenzyl)-N-methylpiperidin-4-amine |

TABLE 2-continued

| Structures of CB1 Receptor Antagonists | | | |
|---|---|---|---|
| Cmd # | Structure | MF | Name |
| 42 | 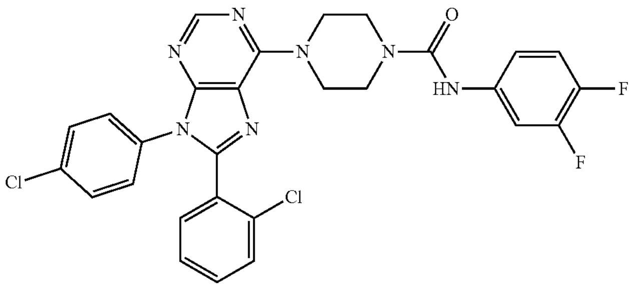 | C28H21Cl2F2N7O | 4-[8-(2-Chlorophenyl)-9-(4-chlorophenyl)-9H-purin-6-yl]-N-(3,4-difluorophenyl)piperazine-1-carboxamide |
| 43 | 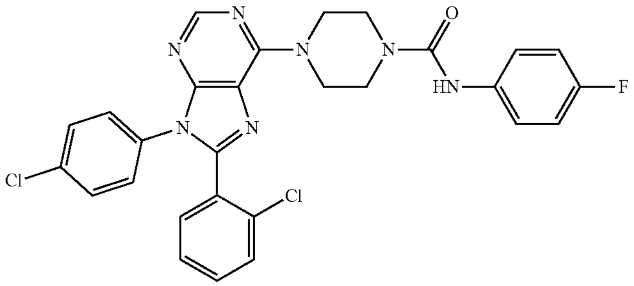 [SMILES: O=C(Nc1ccc(F)cc1)N1CCN(c2ncnc3c2nc(-c2ccccc2Cl)n3-c2ccc(Cl)cc2)CC1] | C28H22Cl2FN7O | 4-[8-(2-Chlorophenyl)-9-(4-chlorophenyl)-9H-purin-6-yl]-N-(4-fluorophenyl)piperazine-1-carboxamide |
| 44 | 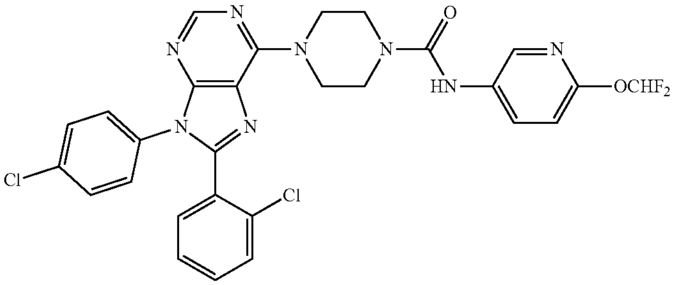 [SMILES: O=C(Nc1ccc(OC(F)F)nc1)N1CCN(c2ncnc3c2nc(-c2ccccc2Cl)n3-c2ccc(Cl)cc2)CC1] | C28H22Cl2F2N8O2 | 4-[8-(2-Chlorophenyl)-9-(4-chlorophenyl)-9H-purin-6-yl]-N-[6-(difluoromethoxy)-pyridin-3-yl]piperazine-1-carboxamide |
| 45 | 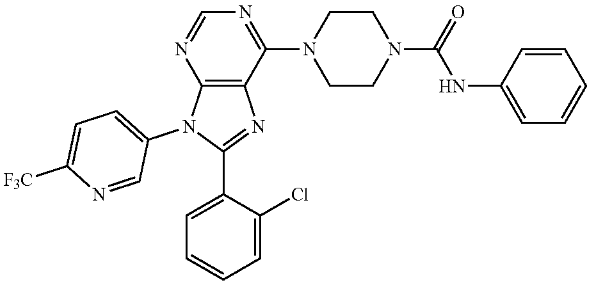 [SMILES: O=C(Nc1ccccc1)N1CCN(c2ncnc3c2nc(-c2ccccc2Cl)n3-c2ccc(C(F)(F)F)nc2)CC1] | C28H22ClF3N8O | N-{1-[8-(2-chlorophenyl)-9-[6-(trifluoromethyl)pyridin-3-yl]-9H-purin-6-yl]piperidin-4-yl}benzamide |
| 46 | 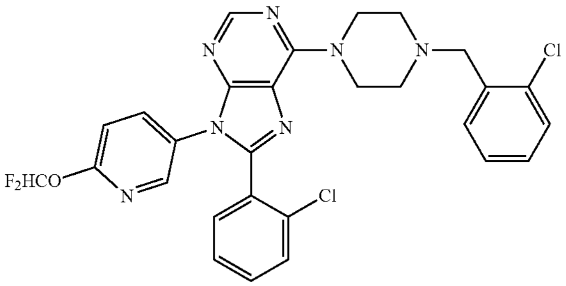 [SMILES: FC(F)Oc1ccc(-n2c(-c3ccccc3Cl)nc3c(N4CCN(Cc5ccccc5Cl)CC4)ncnc32)cn1] | C28H23Cl2F2N7O | 8-(2-chlorophenyl)-6-{4-[(2-chlorophenyl)-methyl]piperazin-1-yl}-9-[6-(difluoromethoxy)-pyridin-3-yl]-9H-purine |

TABLE 2-continued

Structures of CB1 Receptor Antagonists

| Cmd # | Structure | MF | Name |
|---|---|---|---|
| 47 | 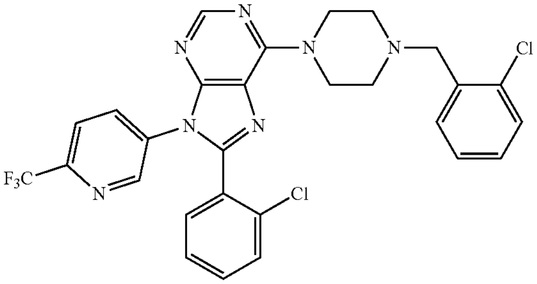 [SMILES: FC(F)(F)c1ccc(-n2c(-c3ccccc3Cl)nc3c(N4CCN(Cc5ccccc5Cl)CC4)ncnc32)cn1] | C28H22Cl2F3N7 | 8-(2-chlorophenyl)-6-{4-[(2-chlorophenyl)-methyl]piperazin-1-yl}-9-[6-(trifluoromethyl)-pyridin-3-yl]-9H-purine |
| 48 | 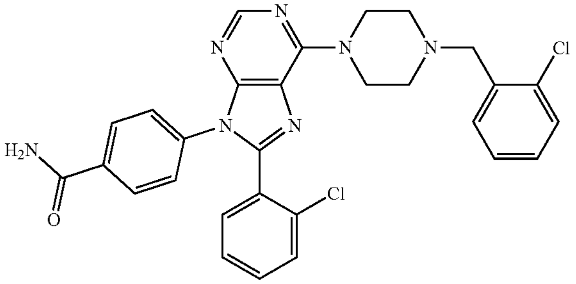 [SMILES: NC(=O)c1ccc(-n2c(-c3ccccc3Cl)nc3c(N4CCN(Cc5ccccc5Cl)CC4)ncnc32)cc1] | C29H25Cl2N7O | 4-[8-(2-chlorophenyl)-6-{4-[(2-chlorophenyl)-methyl]piperazin-1-yl}-9H-purin-9-yl]-benzamide |
| 49 | 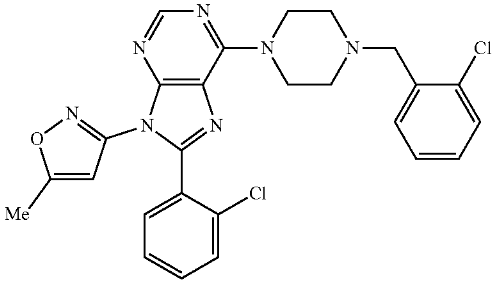 [SMILES: Cc1cc(-n2c(-c3ccccc3Cl)nc3c(N4CCN(Cc5ccccc5Cl)CC4)ncnc32)no1] | C26H23Cl2N70 | 8-(2-chlorophenyl)-6-{4-[(2-chlorophenyl)-methyl]piperazin-1-yl}-9-(5-methyl-1,2-oxazol-3-yl)-9H-purine |
| 50 | 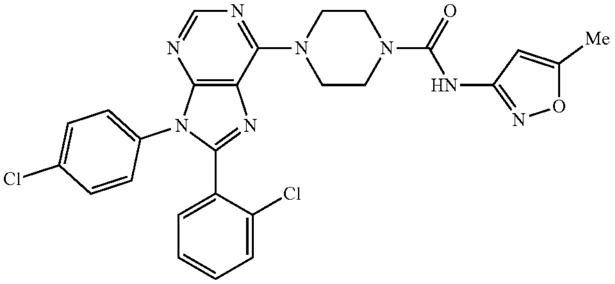 [SMILES: Cc1cc(NC(=O)N2CCN(c3ncnc4c3nc(-c3ccccc3Cl)n4-c3ccc(Cl)cc3)CC2)no1] | C26H22Cl2N8O2 | 4-[8-(2-chlorophenyl)-9-(4-chlorophenyl)-9H-purin-6-yl]-N-(1-methyl-1H-pyrazol-3-yl)piperazine-1-carbox-amide |
| 51 | 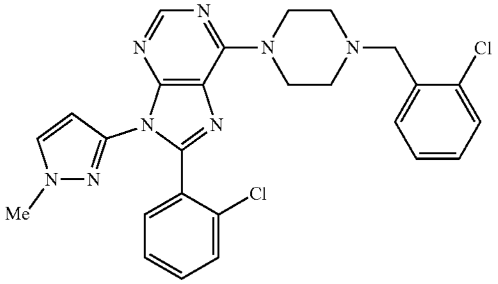 [SMILES: Cn1ccc(-n2c(-c3ccccc3Cl)nc3c(N4CCN(Cc5ccccc5Cl)CC4)ncnc32)n1] | C26H24Cl2N8 | 8-(2-Chlorophenyl)-6-{4-[(2-chlorophenyl)-methyl]-piperazin-1-yl}-9-(1-methyl-1H-pyrazol-3-yl)-9H-purine |
| 52 | | C26H21Cl3N6S | 6-[4-(2-chlorobenzyl)-piperazin-1-yl]-9-(4-chlorophenyl)-8-(3-chlorothiophen-2-yl)-9H-purine |

TABLE 2-continued

Structures of CB1 Receptor Antagonists

| Cmd # | Structure | MF | Name |
|---|---|---|---|
| 53 | | C27H25Cl2N7O | 6-[4-(2-chlorobenzyl)-piperazin-1-yl]-9-(4-chlorophenyl)-8-(3,5-dimethylisoxazol-4-yl)-9H-purine |
| 54 | 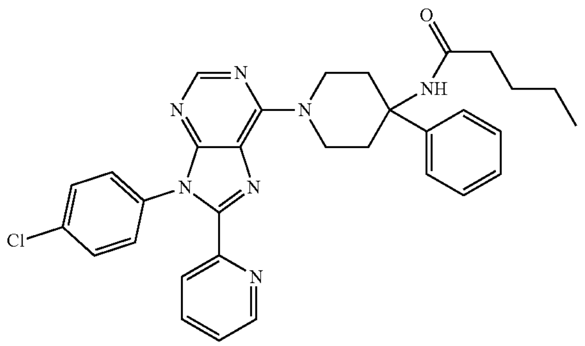 [SMILES: CCCCC(=O)NC1(c2ccccc2)CCN(c2ncnc3c2nc(-c2ccccn2)n3-c2ccc(Cl)cc2)CC1] | C32H32ClN7O | N-{1-[9-(4-chloro-phenyl)-8-pyridin-2-yl-9H-purin-6-yl]-4-phenylpiperidin-4-yl}pentanamide |
| 55 | 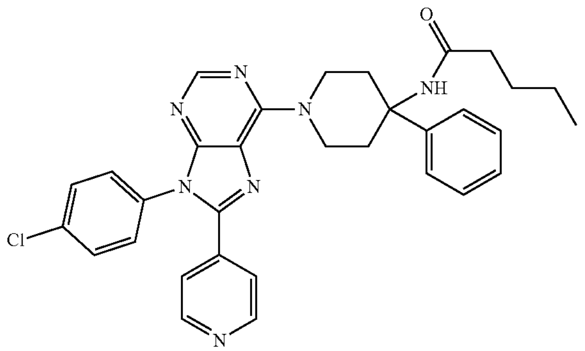 [SMILES: CCCCC(=O)NC1(c2ccccc2)CCN(c2ncnc3c2nc(-c2ccncc2)n3-c2ccc(Cl)cc2)CC1] | C32H32ClN7O | N-{1-[9-(4-chloro-phenyl)-8-pyridin-4-yl-9H-purin-6-yl]-4-phenylpiperidin-4-yl}pentanamide |
| 56 | | C28H22Cl2FN7O | 4-[8-(2-Chlorophenyl)-9-(4-chlorophenyl)-9H-purin-6-yl]-N-(2-fluoro-phenyl)piperazine-1-carboxamide |
| 57 | | C28H21Cl2F2N7O | 4-[8-(2-Chlorophenyl)-9-(4-chlorophenyl)-9H-purin-6-yl]-N-(2,4-difluorophenyl)piper-azine-1-carboxamide |
| 58 | 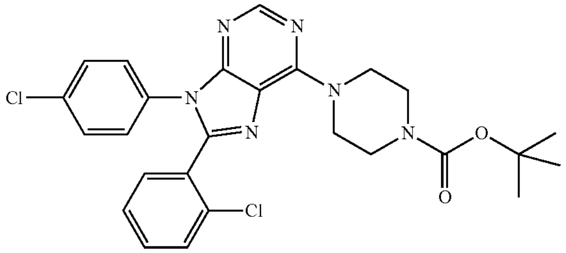 | C32H30Cl2N6O | tert-butyl 4-[8-(2-chlorophenyl)-9-(4-chlorophenyl)-9H-purin-6-yl]piperazine-1-carboxylate |
| 59 | 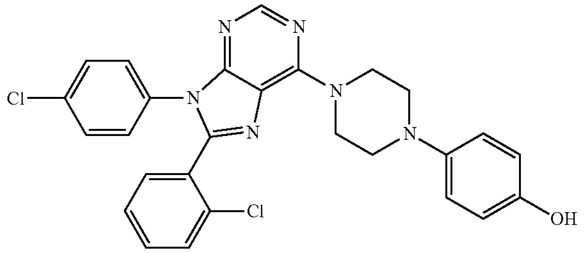 [SMILES: Oc1ccc(N2CCN(c3ncnc4c3nc(-c3ccccc3Cl)n4-c3ccc(Cl)cc3)CC2)cc1] | C27H22Cl2N6O | 4-{4-[8-(2-chloro-phenyl)-9-(4-chloro-phenyl)-9H-purin-6-yl]piperazin-1-yl}-phenol |

TABLE 2-continued

| Structures of CB1 Receptor Antagonists | | | |
|---|---|---|---|
| Cmd # | Structure | MF | Name |
| 60 | 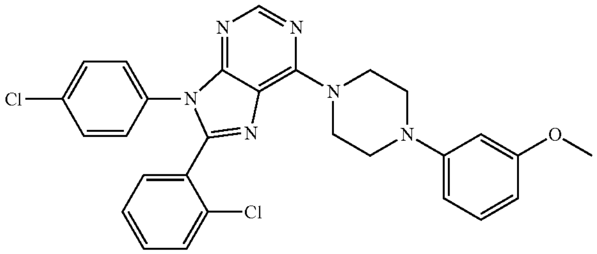 [SMILES: COc1cccc(N2CCN(c3ncnc4c3nc(-c3ccccc3Cl)n4-c3ccc(Cl)cc3)CC2)c1] | C28H24Cl2N6O | 8-(2-chlorophenyl)-9-(4-chlorophenyl)-6-[4-(3-methoxyphenyl)-piperazin-1-yl]-9H-purine |
| 61 | 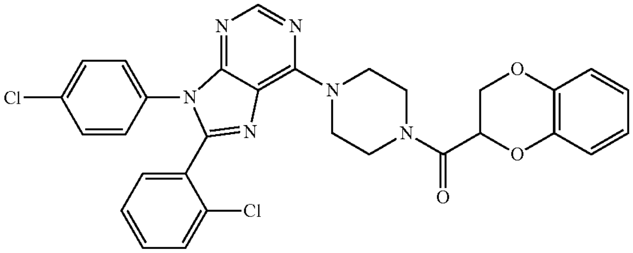 [SMILES: O=C(C1COc2ccccc2O1)N1CCN(c2ncnc3c2nc(-c2ccccc2Cl)n3-c2ccc(Cl)cc2)CC1] | C30H24Cl2N6O3 | 8-(2-chlorophenyl)-9-(4-chlorophenyl)-6-[4-(2,3-dihydro-1,4-benzodioxin-2-yl-carbonyl)piperazin-1-yl]-9H-purine |
| 62 | 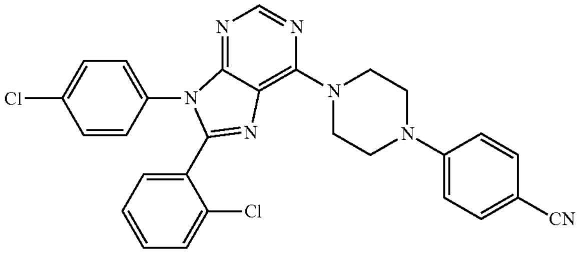 | C28H21Cl2N7 | 4-{4-[8-(2-chloro-phenyl)-9-(4-chloro-phenyl)-9H-purin-6-yl]piperazin-1-yl}-benzonitrile |
| 63 | 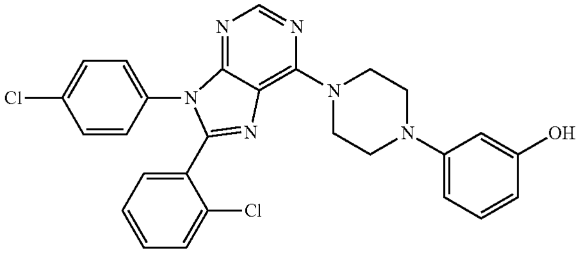 [SMILES: Oc1cccc(N2CCN(c3ncnc4c3nc(-c3ccccc3Cl)n4-c3ccc(Cl)cc3)CC2)c1] | C27H22Cl2N6O | 3-{4-[8-(2-chloro-phenyl)-9-(4-chloro-phenyl)-9H-purin-6-yl]piperazin-1-yl}-phenol |
| 64 | 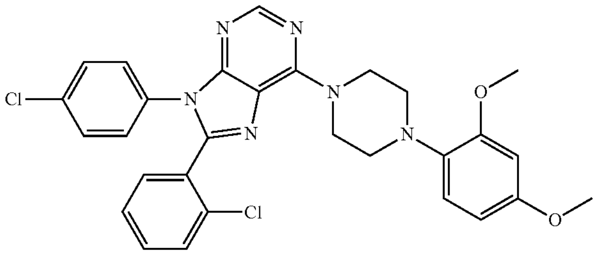 [SMILES: COc1ccc(N2CCN(c3ncnc4c3nc(-c3ccccc3Cl)n4-c3ccc(Cl)cc3)CC2)c(OC)c1] | C29H26Cl2N6O2 | 8-(2-chlorophenyl)-9-(4-chlorophenyl)-6-[4-(2,4-dimethoxyphenyl)-piperazin-1-yl]-9H-purine |

TABLE 2-continued

| Structures of CB1 Receptor Antagonists | | | |
|---|---|---|---|
| Cmd # | Structure | MF | Name |
| 65 | 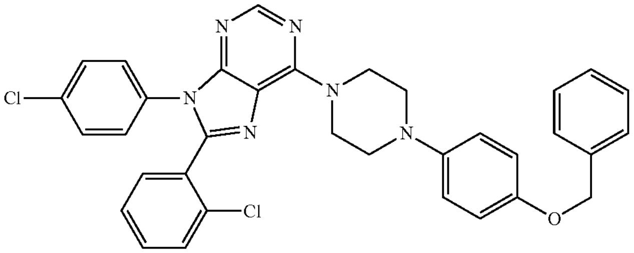 [SMILES: Clc1ccc(-n2c(-c3ccccc3Cl)nc3c(N4CCN(c5ccc(OCc6ccccc6)cc5)CC4)ncnc32)cc1] | C34H28Cl2N6O | 6-{4-[4-(benzyloxy)-phenyl]piperazin-1-yl}-8-(2-chlorophenyl)-9-(4-chlorophenyl)-9H-purine |
| 66 | 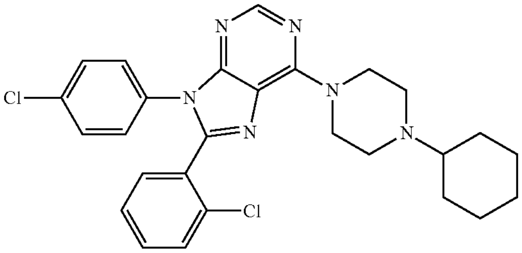 [SMILES: Clc1ccc(-n2c(-c3ccccc3Cl)nc3c(N4CCN(C5CCCCC5)CC4)ncnc32)cc1] | C27H28Cl2N6 | 8-(2-chlorophenyl)-9-(4-chlorophenyl)-6-(4-cyclohexylpiperazin-1-yl)-9H-purine |
| 67 | 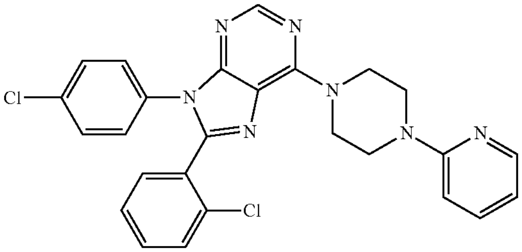 [SMILES: Clc1ccc(-n2c(-c3ccccc3Cl)nc3c(N4CCN(c5ccccn5)CC4)ncnc32)cc1] | C26H21Cl2N7 | 8-(2-chlorophenyl)-9-(4-chlorophenyl)-6-(4-pyridin-2-ylpiperazin-1-yl)-9H-purine |
| 68 | 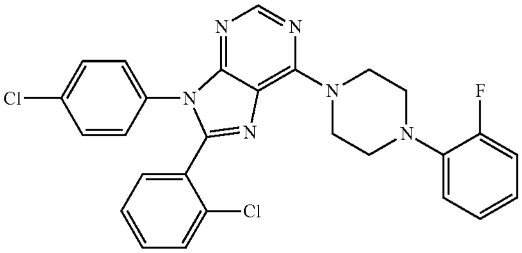 | C27H21Cl2FN6 | 8-(2-chlorophenyl)-9-(4-chlorophenyl)-6-[4-(2-fluorophenyl)-piperazin-1-yl]-9H-purine |
| 69 | 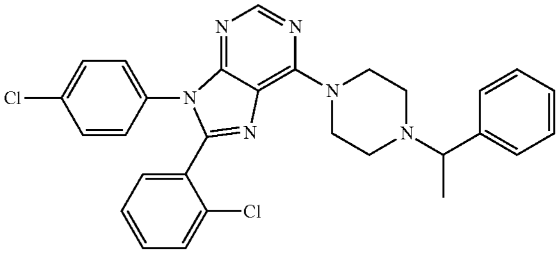 [SMILES: CC(c1ccccc1)N1CCN(c2ncnc3c2nc(-c2ccccc2Cl)n3-c2ccc(Cl)cc2)CC1] | C29H26Cl2N6 | 8-(2-chlorophenyl)-9-(4-chlorophenyl)-6-[4-(1-phenylethyl)-piperazin-1-yl]-9H-purine |
| 70 | 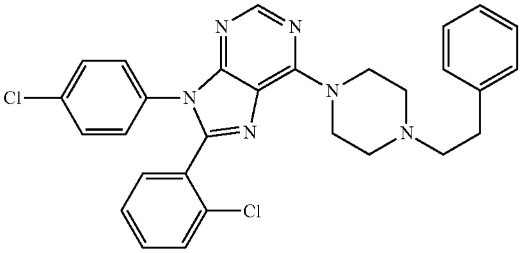 [SMILES: Clc1ccc(-n2c(-c3ccccc3Cl)nc3c(N4CCN(CCc5ccccc5)CC4)ncnc32)cc1] | C29H26Cl2N6 | 8-(2-chlorophenyl)-9-(4-chlorophenyl)-6-[4-(2-phenylethyl)-piperazin-1-yl]-9H-purine |

TABLE 2-continued

| Structures of CB1 Receptor Antagonists | | | |
|---|---|---|---|
| Cmd # | Structure | MF | Name |
| 71 | 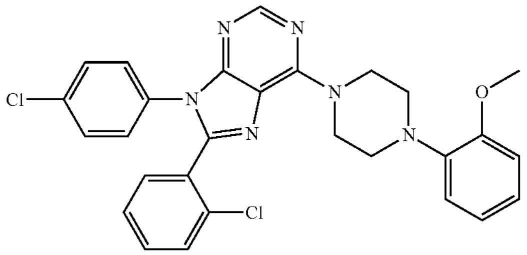 [SMILES: COc1ccccc1N1CCN(c2ncnc3c2nc(-c2ccccc2Cl)n3-c2ccc(Cl)cc2)CC1] | C28H25Cl3N6O | 8-(2-chlorophenyl)-9-(4-chlorophenyl)-6-[4-(2-methoxyphenyl)-piperazin-1-yl]-9H-purine |
| 72 | 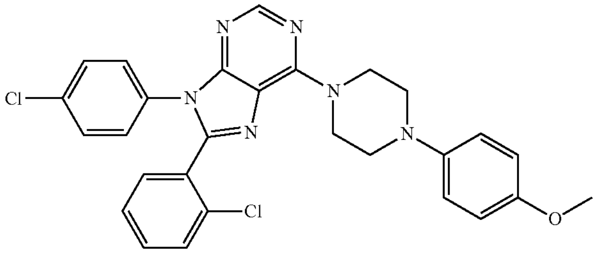 [SMILES: COc1ccc(N2CCN(c3ncnc4c3nc(-c3ccccc3Cl)n4-c3ccc(Cl)cc3)CC2)cc1] | C28H25Cl3N6O | 8-(2-chlorophenyl)-9-(4-chlorophenyl)-6-[4-(4-methoxyphenyl)-piperazin-1-yl]-9H-purine |
| 73 | 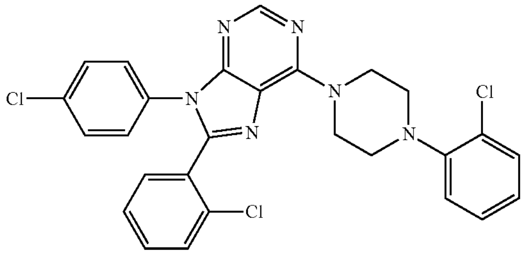 [SMILES: Clc1ccc(-n2c(-c3ccccc3Cl)nc3c(N4CCN(c5ccccc5Cl)CC4)ncnc32)cc1] | C27H21Cl3N6 | 8-(2-chlorophenyl)-9-(4-chlorophenyl)-6-[4-(2-chlorophenyl)-piperazin-1-yl]-9H-purine |
| 74 | 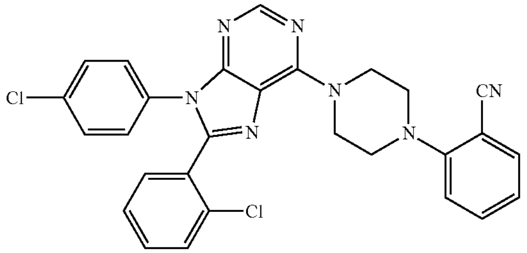 [SMILES: N#Cc1ccccc1N1CCN(c2ncnc3c2nc(-c2ccccc2Cl)n3-c2ccc(Cl)cc2)CC1] | C28H21Cl2N7 | 2-{4-[8-(2-chloro-phenyl)-9-(4-chloro-phenyl)-9H-purin-6-yl]piperazin-1-yl}-benzonitrile |
| 75 | 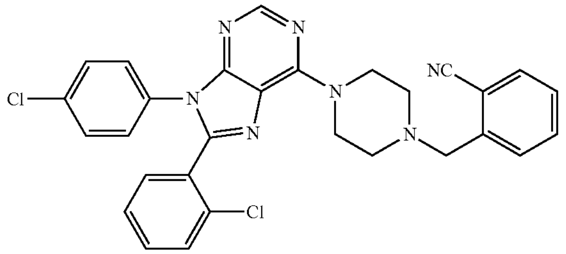 [SMILES: N#Cc1ccccc1CN1CCN(c2ncnc3c2nc(-c2ccccc2Cl)n3-c2ccc(Cl)cc2)CC1] | C29H23Cl2N7 | 6-[4-(2-cyanobenzyl)-piperazin-1-yl]-8-(2-chlorophenyl)-9-(4-chlorophenyl)-9H-purine |

TABLE 2-continued

| Structures of CB1 Receptor Antagonists | | | |
|---|---|---|---|
| Cmd # | Structure | MF | Name |
| 76 | 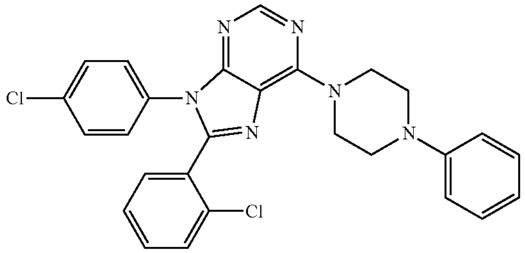 [SMILES: Clc1ccc(-n2c(-c3ccccc3Cl)nc3c(N4CCN(c5ccccc5)CC4)ncnc32)cc1] | C27H22Cl2N6 | 8-(2-chlorophenyl)-9-(4-chlorophenyl)-6-(4-phenylpiperazin-1-yl)-9H-purine |
| 77 | 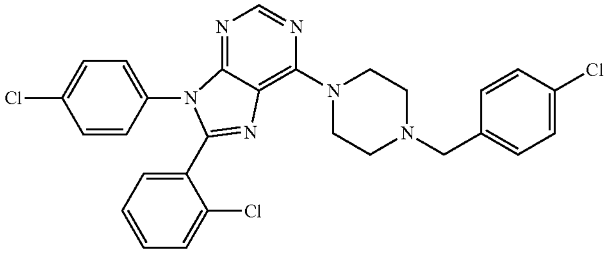 [SMILES: Clc1ccc(CN2CCN(c3ncnc4c3nc(-c3ccccc3Cl)n4-c3ccc(Cl)cc3)CC2)cc1] | C27H21Cl3N6 | 6-[4-(4-chlorobenzyl)-piperazin-1-yl]-8-(2-chlorophenyl)-9-(4-chlorophenyl)-9H-purine |
| 78 | 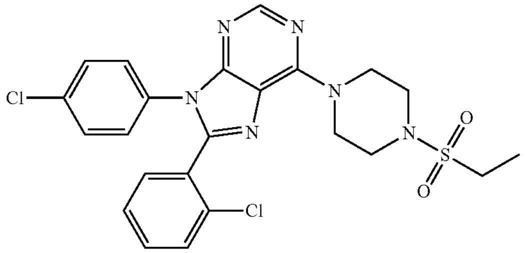 [SMILES: CCS(=O)(=O)N1CCN(c2ncnc3c2nc(-c2ccccc2Cl)n3-c2ccc(Cl)cc2)CC1] | C23H22Cl2N6O2S | 8-(2-chlorophenyl)-9-(4-chlorophenyl)-6-[4-(ethylsulfonyl)-piperazin-1-yl]-9H-purine |
| 79 | 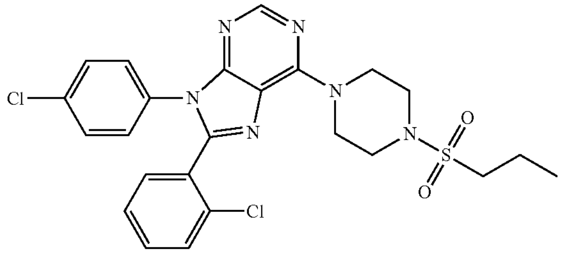 [SMILES: CCCS(=O)(=O)N1CCN(c2ncnc3c2nc(-c2ccccc2Cl)n3-c2ccc(Cl)cc2)CC1] | C24H24Cl2N6O2S | 8-(2-chlorophenyl)-9-(4-chlorophenyl)-6-[4-(propylsulfonyl)-piperazin-1-yl]-9H-purine |
| 80 | 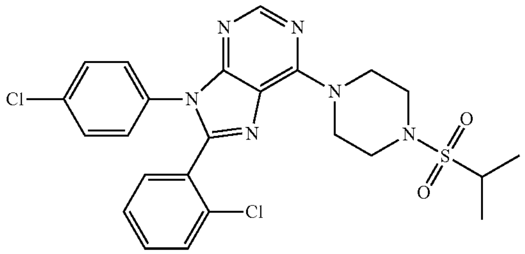 [SMILES: CC(C)S(=O)(=O)N1CCN(c2ncnc3c2nc(-c2ccccc2Cl)n3-c2ccc(Cl)cc2)CC1] | C24H24Cl2N6O2S | 8-(2-chlorophenyl)-9-(4-chlorophenyl)-6-{4-[(1-methylethyl)-sulfonyl]piperazin-1-yl}-9H-purine |
| 81 | 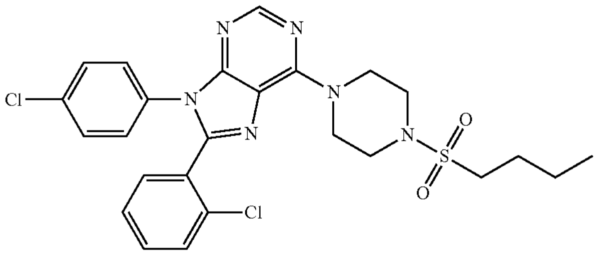 [SMILES: CCCCS(=O)(=O)N1CCN(c2ncnc3c2nc(-c2ccccc2Cl)n3-c2ccc(Cl)cc2)CC1] | C25H26Cl2N6O2S | 8-(2-chlorophenyl)-9-(4-chlorophenyl)-6-[4-(butylsulfonyl)-piperazin-1-yl]-9H-purine |

TABLE 2-continued

Structures of CB1 Receptor Antagonists

| Cmd # | Structure | MF | Name |
| --- | --- | --- | --- |
| 82 | 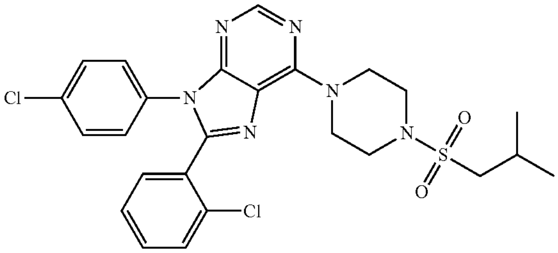 [SMILES: CC(C)CS(=O)(=O)N1CCN(c2ncnc3c2nc(-c2ccccc2Cl)n3-c2ccc(Cl)cc2)CC1] | C25H26Cl2N6O2S | 8-(2-chlorophenyl)-9-(4-chlorophenyl)-6-{4-[(2-methylpropyl)-sulfonyl]piperazin-1-yl}-9H-purine |
| 83 | 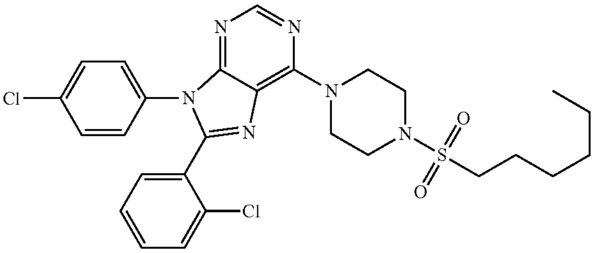 [SMILES: CCCCCCS(=O)(=O)N1CCN(c2ncnc3c2nc(-c2ccccc2Cl)n3-c2ccc(Cl)cc2)CC1] | C27H30Cl2N6O2S | 8-(2-chlorophenyl)-9-(4-chlorophenyl)-6-[4-(hexylsulfonyl)-piperazin-1-yl]-9H-purine |
| 84 | 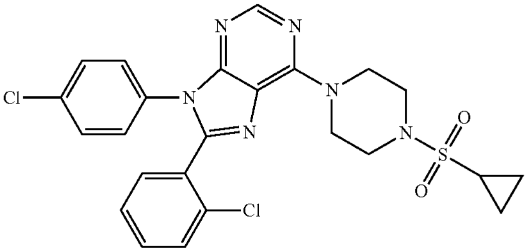 [SMILES: O=S(=O)(C1CC1)N1CCN(c2ncnc3c2nc(-c2ccccc2Cl)n3-c2ccc(Cl)cc2)CC1] | C24H22Cl2N6O2S | 8-(2-chlorophenyl)-9-(4-chlorophenyl)-6-[4-(cyclopropylsulfonyl)-piperazin-1-yl]-9H-purine |
| 85 | 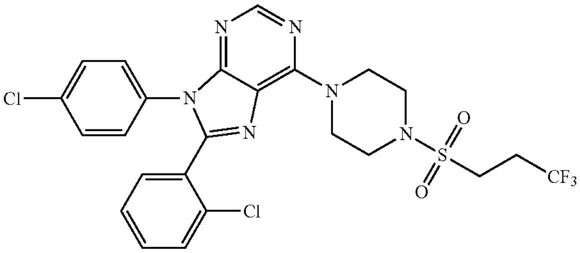 [SMILES: O=S(=O)(CCC(F)(F)F)N1CCN(c2ncnc3c2nc(-c2ccccc2Cl)n3-c2ccc(Cl)cc2)CC1] | C24H21Cl2F3N6O2S | 8-(2-chlorophenyl)-9-(4-chlorophenyl)-6-{4-[(3,3,3-trifluoropropyl)-sulfonyl]piperazin-1-yl}-9H-purine |
| 86 | 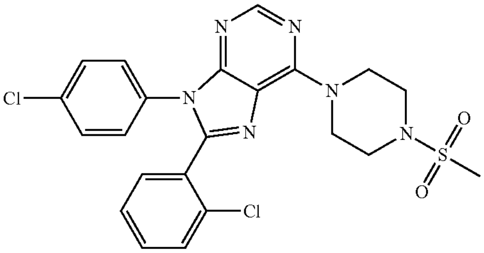 [SMILES: CS(=O)(=O)N1CCN(c2ncnc3c2nc(-c2ccccc2Cl)n3-c2ccc(Cl)cc2)CC1] | C22H20Cl2N6O2S | 8-(2-chlorophenyl)-9-(4-chlorophenyl)-6-[4-(methylsulfonyl)-piperazin-1-yl]-9H-purine |

TABLE 2-continued

Structures of CB1 Receptor Antagonists

| Cmd # | Structure | MF | Name |
|---|---|---|---|
| 87 | 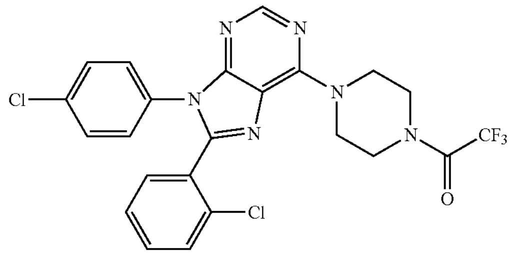 [SMILES: O=C(N1CCN(c2ncnc3c2nc(-c2ccccc2Cl)n3-c2ccc(Cl)cc2)CC1)C(F)(F)F] | C23H17Cl2F3N6O1 | 8-(2-chlorophenyl)-9-(4-chlorophenyl)-6-[4-(trifluoroacetyl)-piperazin-1-yl]-9H-purine |
| 88 | 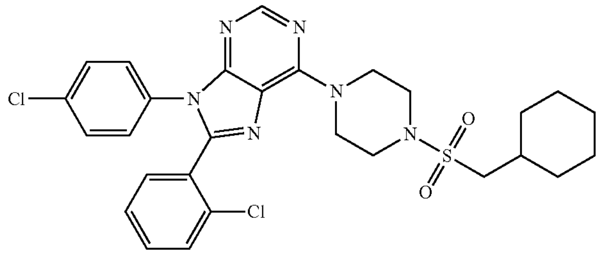 [SMILES: O=S(=O)(CC1CCCCC1)N1CCN(c2ncnc3c2nc(-c2ccccc2Cl)n3-c2ccc(Cl)cc2)CC1] | C26H28Cl2N6O2S | 8-(2-chlorophenyl)-9-(4-chlorophenyl)-6-[4-(pentylsulfonyl)-piperazin-1-yl]-9H-purine |
| 89 | 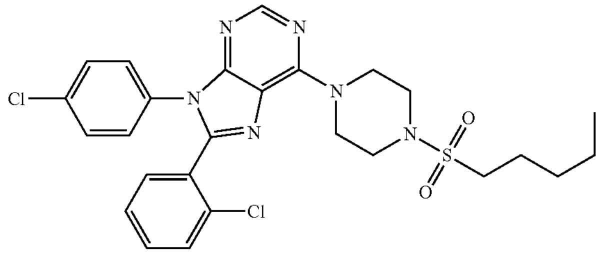 | C28H30Cl2N6O2S | 8-(2-chlorophenyl)-9-(4-chlorophenyl)-6-{4-[(cyclohexylmethyl)-sulfonyl]piperazin-1-yl}-9H-purine |
| 90 | 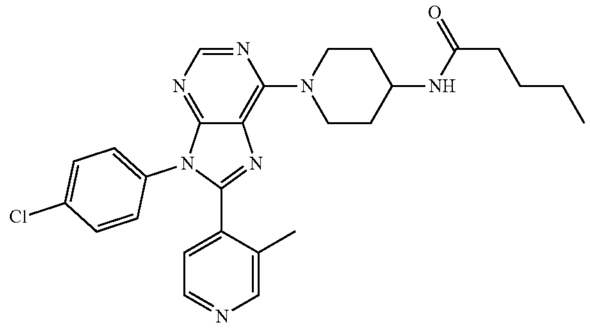 | C27H30ClN7O | N-{1-[9-(4-chloro-phenyl)-8-(3-methyl-pyridin-4-yl)-9H-purin-6-yl]piperidin-4-yl}-pentanamide |
| 91 | 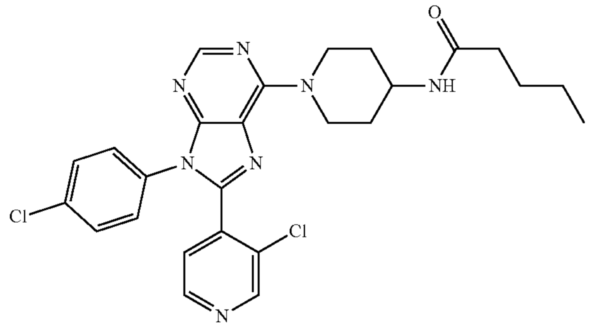 [SMILES: CCCCC(=O)NC1CCN(c2ncnc3c2nc(-c2ccncc2C)n3-c2ccc(Cl)cc2)CC1] | C26H27Cl2N7O | N-{1-[9-(4-chloro-phenyl)-8-(3-chloro-pyridin-4-yl)-9H-purin-6-yl]piperidin-4-yl}pentanamide |

TABLE 2-continued

| Structures of CB1 Receptor Antagonists | | | |
|---|---|---|---|
| Cmd # | Structure | MF | Name |
| 92 | 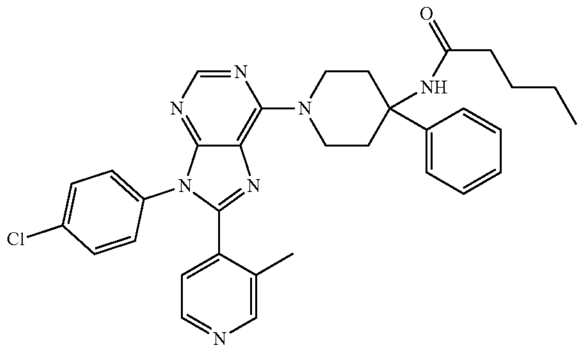 [SMILES: CCCCC(=O)NC1(c2ccccc2)CCN(c2ncnc3c2nc(-c2ccncc2C)n3-c2ccc(Cl)cc2)CC1] | C33H34ClN7O | N-{1-(9-(4-chloro-phenyl)-8-(3-methyl-pyridin-4-yl)-9H-purin-6-yl]-4-phenyl-piperidin-4-yl}-pentanamide |
| 93 | 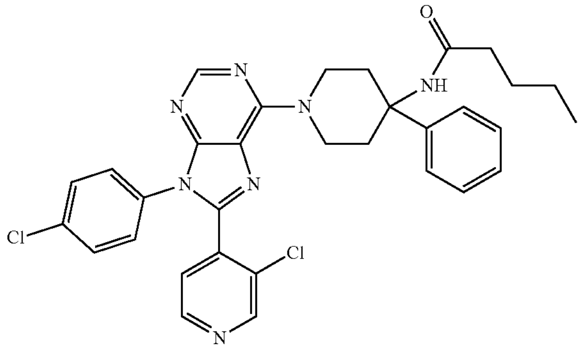 [SMILES: CCCCC(=O)NC1(c2ccccc2)CCN(c2ncnc3c2nc(-c2ccncc2Cl)n3-c2ccc(Cl)cc2)CC1] | C32H31Cl2N7O | N-{1-[9-(4-chloro-phenyl)-8-(3-chloro-pyridin-4-yl)-9H-purin-6-yl]-4-phenyl-piperidin-4-yl}-pentanamide |
| 94 | 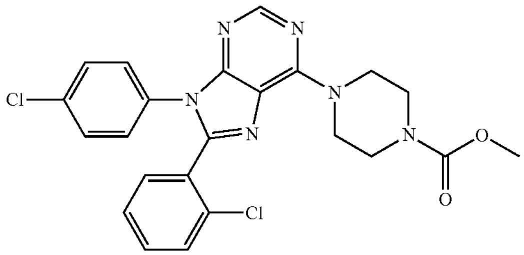 [SMILES: COC(=O)N1CCN(c2ncnc3c2nc(-c2ccccc2Cl)n3-c2ccc(Cl)cc2)CC1] | C23H20Cl2N6O2 | N-{1-[9-(4-chloro-phenyl)-8-(2,4-dichlorophenyl)-9H-purin-6-yl]-4-phenylpiperidin-4-yl}pentanamide |
| 95 | 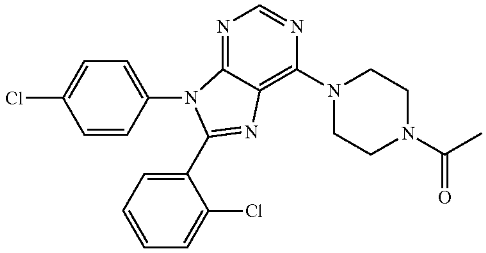 [SMILES: CC(=O)N1CCN(c2ncnc3c2nc(-c2ccccc2Cl)n3-c2ccc(Cl)cc2)CC1] | C23H20Cl2N6O | 6-(4-acetylpiperazin-1-yl)-8-(2-chlorophenyl)-9-(4-chlorophenyl)-9H-purine |
| 96 | 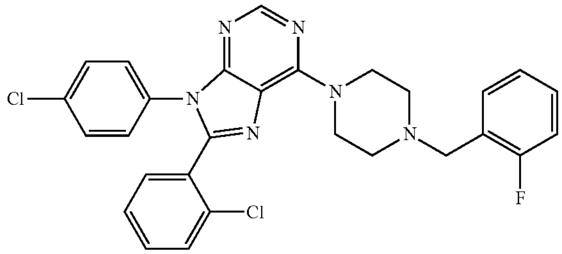 [SMILES: Fc1ccccc1CN1CCN(c2ncnc3c2nc(-c2ccccc2Cl)n3-c2ccc(Cl)cc2)CC1] | C28H23Cl2FN6 | 8-(2-chlorophenyl)-9-(4-chlorophenyl)-6-[4-(2-fluorobenzyl)-piperazin-1-yl]-9H-purine |

TABLE 2-continued

| Structures of CB1 Receptor Antagonists | | | |
|---|---|---|---|
| Cmd # | Structure | MF | Name |
| 97 | 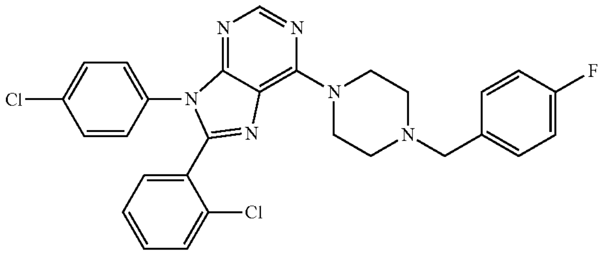 [SMILES: Fc1ccc(CN2CCN(c3ncnc4c3nc(-c3ccccc3Cl)n4-c3ccc(Cl)cc3)CC2)cc1] | C28H23Cl2FN6 | 8-(2-chlorophenyl)-9-(4-chlorophenyl)-6-[4-(4-fluorobenzyl)-piperazin-1-yl]-9H-purine |
| 98 | 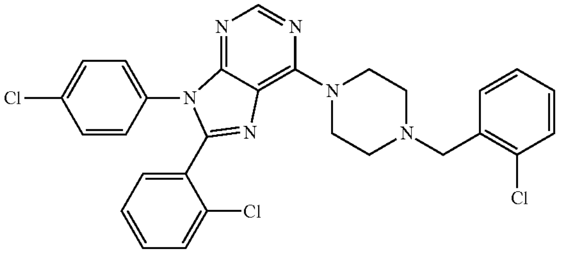 [SMILES: Clc1ccc(-n2c(-c3ccccc3Cl)nc3c(N4CCN(Cc5ccccc5Cl)CC4)ncnc32)cc1] | C28H23Cl3N6 | 6-[4-(2-chlorobenzyl)-piperazin-1-yl]-8-(2-chlorophenyl)-9-(4-chlorophenyl)-9H-purine |
| 99 | 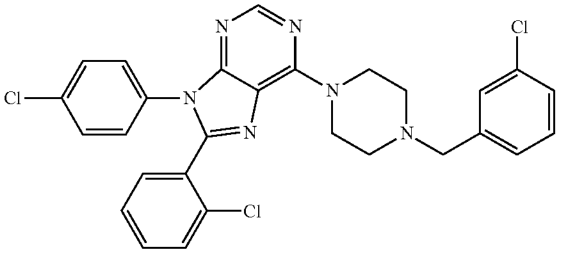 [SMILES: Clc1ccc(-n2c(-c3ccccc3Cl)nc3c(N4CCN(Cc5cccc(Cl)c5)CC4)ncnc32)cc1] | C28H23Cl3N6 | 6-[4-(3-chlorobenzyl)-piperazin-1-yl]-8-(2-chlorophenyl)-9-(4-chlorophenyl)-9H-purine |
| 100 | 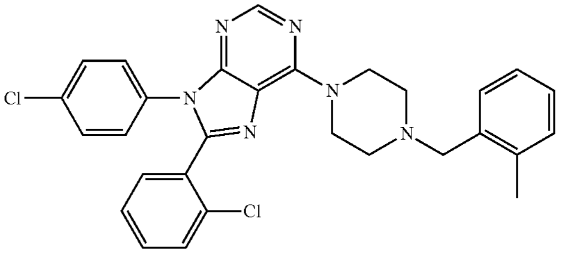 [SMILES: Cc1ccccc1CN1CCN(c2ncnc3c2nc(-c2ccccc2Cl)n3-c2ccc(Cl)cc2)CC1] | C29H26Cl2N6 | 8-(2-chlorophenyl)-9-(4-chlorophenyl)-6-[4-(2-methylbenzyl)-piperazin-1-yl]-9H-purine |
| 101 | 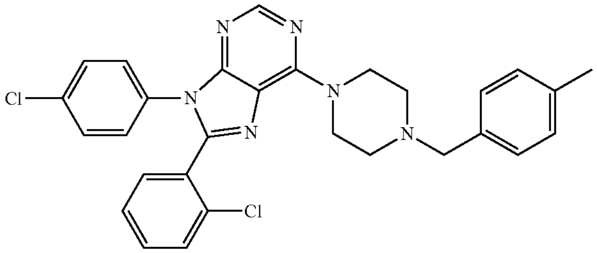 [SMILES: Cc1ccc(CN2CCN(c3ncnc4c3nc(-c3ccccc3Cl)n4-c3ccc(Cl)cc3)CC2)cc1] | C29H26Cl2N6 | 8-(2-chlorophenyl)-9-(4-chlorophenyl)-6-[4-(4-methylbenzyl)-piperazin-1-yl]-9H-purine |
| 102 | 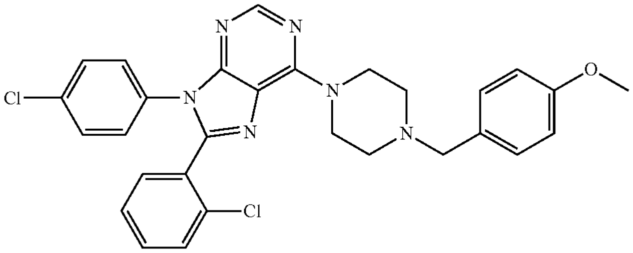 [SMILES: COc1ccc(CN2CCN(c3ncnc4c3nc(-c3ccccc3Cl)n4-c3ccc(Cl)cc3)CC2)cc1] | C29H26Cl2N6O | 8-(2-chlorophenyl)-9-(4-chlorophenyl)-6-[4-(4-methoxybenzyl)-piperazin-1-yl]-9H-purine |

TABLE 2-continued

| Structures of CB1 Receptor Antagonists | | | |
|---|---|---|---|
| Cmd # | Structure | MF | Name |
| 103 | 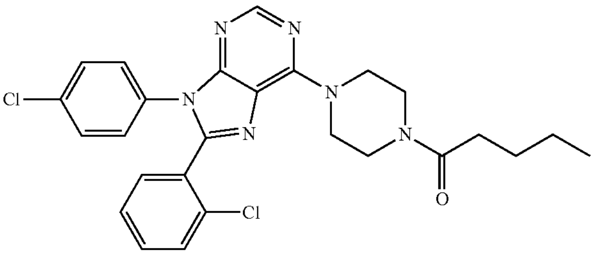 [SMILES: CCCCC(=O)N1CCN(c2ncnc3c2nc(-c2ccccc2Cl)n3-c2ccc(Cl)cc2)CC1] | C26H26Cl2N6O | 8-(2-chlorophenyl)-9-(4-chlorophenyl)-6-(4-pentanoylpiperazin-1-yl)-9H-purine |
| 104 | 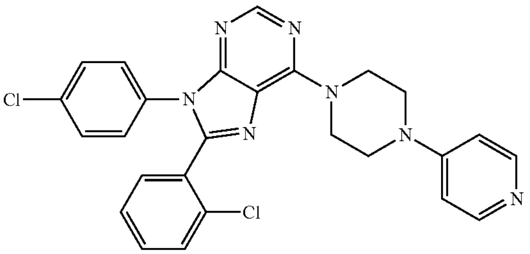 [SMILES: Clc1ccc(-n2c(-c3ccccc3Cl)nc3c(N4CCN(c5ccncc5)CC4)ncnc32)cc1] | C26H21Cl2N7 | 8-(2-chlorophenyl)-9-(4-chlorophenyl)-6-(4-pyridin-4-ylpiperazin-1-yl)-9H-purine |
| 105 | 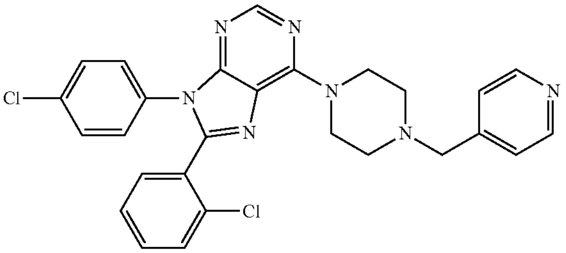 [SMILES: Clc1ccc(-n2c(-c3ccccc3Cl)nc3c(N4CCN(Cc5ccncc5)CC4)ncnc32)cc1] | C27H23Cl2N7 | 8-(2-chlorophenyl)-9-(4-chlorophenyl)-6-[4-(pyridin-4-ylmethyl)-piperazin-1-yl]-9H-purine |
| 106 | 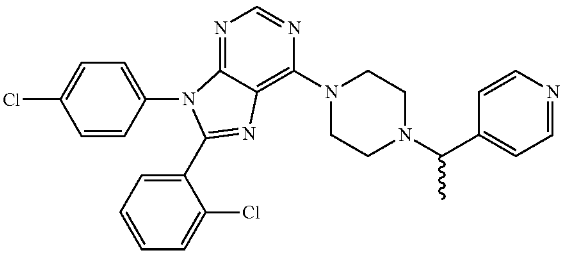 [SMILES: CC(c1ccncc1)N1CCN(c2ncnc3c2nc(-c2ccccc2Cl)n3-c2ccc(Cl)cc2)CC1] | C28H25Cl2N7 | 8-(2-chlorophenyl)-9-(4-chlorophenyl)-6-[4-(1-pyridin-4-ylethyl)-piperazin-1-yl]-9H-purine |
| 107 | 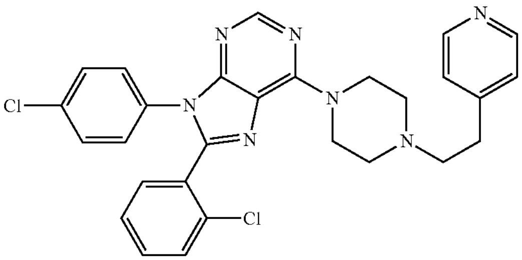 [SMILES: Clc1ccc(-n2c(-c3ccccc3Cl)nc3c(N4CCN(CCc5ccncc5)CC4)ncnc32)cc1] | C28H25Cl2N7 | 8-(2-chlorophenyl)-9-(4-chlorophenyl)-6-[4-(2-pyridin-4-ylethyl)-piperazin-1-yl]-9H-purine |

TABLE 2-continued

Structures of CB1 Receptor Antagonists

| Cmd # | Structure | MF | Name |
|---|---|---|---|
| 108 | 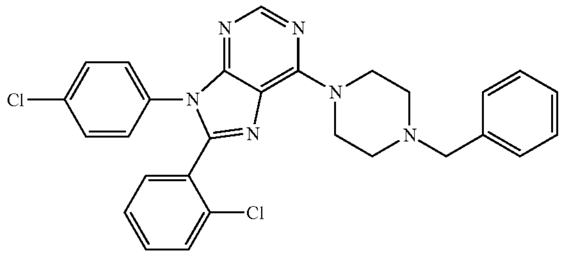 [SMILES: Clc1ccc(-n2c(-c3ccccc3Cl)nc3c(N4CCN(Cc5ccccc5)CC4)ncnc32)cc1] | C28H24Cl2N6 | 6-(4-benzylpiperazin-1-yl)-8-(2-chlorophenyl)-9-(4-chlorophenyl)-9H-purine |
| 109 | 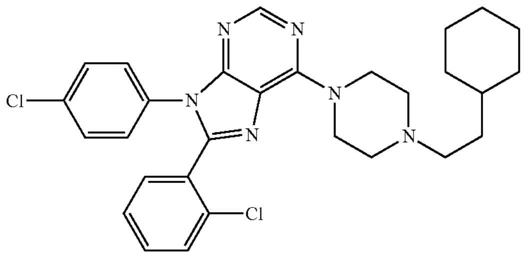 [SMILES: Clc1ccc(-n2c(-c3ccccc3Cl)nc3c(N4CCN(CCC5CCCCC5)CC4)ncnc32)cc1] | C29H32Cl2N6 | 8-(2-chlorophenyl)-9-(4-chlorophenyl)-6-[4-(2-cyclohexylethyl)-piperazin-1-yl]-9H-purine |
| 110 | 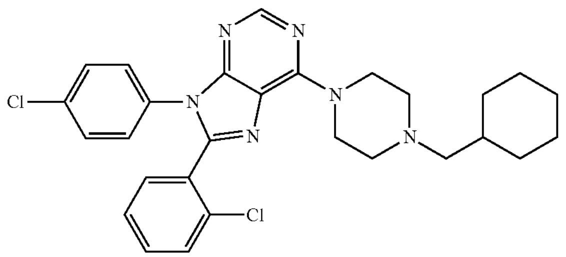 [SMILES: Clc1ccc(-n2c(-c3ccccc3Cl)nc3c(N4CCN(CC5CCCCC5)CC4)ncnc32)cc1] | C28H30Cl2N6 | 8-(2-chlorophenyl)-9-(4-chlorophenyl)-6-[4-(cyclohexylmethyl)-piperazin-1-yl]-9H-purine |
| 111 | | C29H23Cl2F3N6 | 8-(2-chlorophenyl)-9-(4-chlorophenyl)-6-{4-[2-(trifluoromethyl) benzyl]piperazin-1-yl}-9H-purine |
| 112 | | C29H23Cl2F3N6O | 8-(2-chlorophenyl)-9-(4-chlorophenyl)-6-{4-[2-(trifluoromethoxy)-benzyl]piperazin-1-yl}-9H-purine |
| 113 | | C27H22Cl3N7 | 8-(2-chlorophenyl)-9-(4-chlorophenyl)-6-(4-[(3-chloropyridin-4-yl)methyl]piperazin-1-yl}-9H-purine |
| 114 | | C27H26Cl2N8 | 8-(2-chlorophenyl)-9-(4-chlorophenyl)-6-{4-[(1,5-dimethyl-1H-pyrazol-4-yl)methyl]-piperazin-1-yl}-9H-purine |
| 115 | | C25H22Cl2N8O | 8-(2-chlorophenyl)-9-(4-chlorophenyl)-6-{4-[(5-methyl-1,2,4-oxa-diazol-3-yl)methyl]-piperazin-1-yl}-9H-purine |
| 116 | | C28H23Cl2FN8 | 4-[8-(2-chlorophenyl)-9-(4-chlorophenyl)-9H-purin-6-yl]-N-(4-fluoro-phenyl)piperazine-1-carboximidamide |

TABLE 2-continued

| Structures of CB1 Receptor Antagonists | | | |
|---|---|---|---|
| Cmd # | Structure | MF | Name |
| 117 | 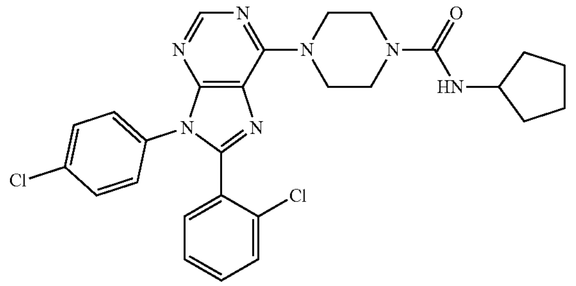 [SMILES: O=C(NC1CCCC1)N1CCN(c2ncnc3c2nc(-c2ccccc2Cl)n3-c2ccc(Cl)cc2)CC1] | C27H27Cl2N7O | 4-[8-(2-Chlorophenyl)-9-(4-chlorophenyl)-9H-purin-6-yl]-N-cyclopentylpiperazine-1-carboxamide |
| 118 | 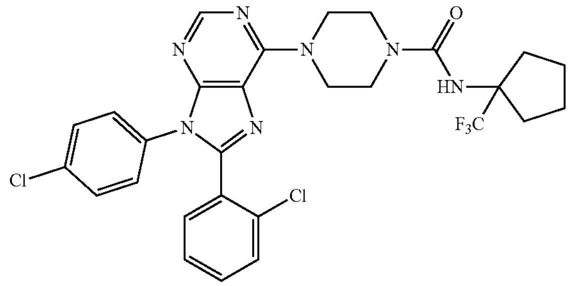 [SMILES: O=C(NC1(C(F)(F)F)CCCC1)N1CCN(c2ncnc3c2nc(-c2ccccc2Cl)n3-c2ccc(Cl)cc2)CC1] | C28H26Cl2F3N7O | 4-[8-(2-Chlorophenyl)-9-(4-chlorophenyl)-9H-purin-6-yl]-N-[1-(trifluoromethyl)cyclopentyl]piperazine-1-carboxamide |
| 119 | 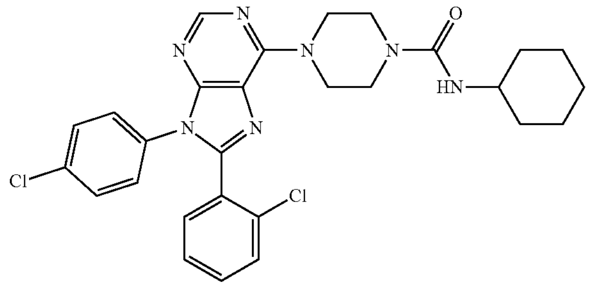 [SMILES: O=C(NC1CCCCC1)N1CCN(c2ncnc3c2nc(-c2ccccc2Cl)n3-c2ccc(Cl)cc2)CC1] | C28H29Cl2N7O | 4-[8-(2-chlorophenyl)-9-(4-chlorophenyl)-9H-purin-6-yl]-N-cyclohexylpiperazine-1-carboxamide |
| 120 | 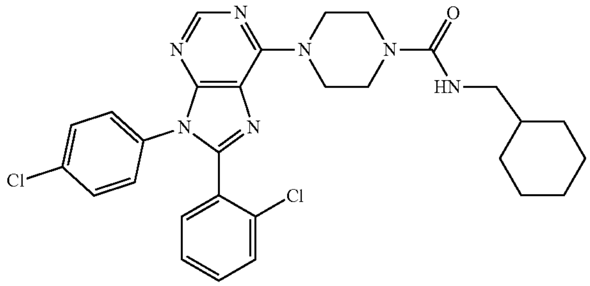 [SMILES: O=C(NCC1CCCCC1)N1CCN(c2ncnc3c2nc(-c2ccccc2Cl)n3-c2ccc(Cl)cc2)CC1] | C29H31Cl2N7O | 4-[8-(2-chlorophenyl)-9-(4-chlorophenyl)-9H-purin-6-yl]-N-(cyclohexylmethyl)piperazine-1-carboxamide |
| 121 | 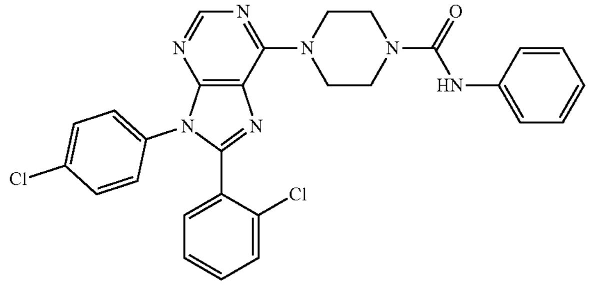 [SMILES: O=C(Nc1ccccc1)N1CCN(c2ncnc3c2nc(-c2ccccc2Cl)n3-c2ccc(Cl)cc2)CC1] | C28H23Cl2N7O | 4-[8-(2-chlorophenyl)-9-(4-chlorophenyl)-9H-purin-6-yl]-N-phenylpiperazine-1-carboxamide |

TABLE 2-continued

| Structures of CB1 Receptor Antagonists | | | |
|---|---|---|---|
| Cmd # | Structure | MF | Name |
| 122 | 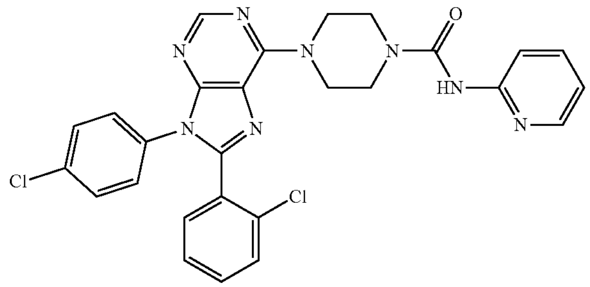 [SMILES: O=C(Nc1ccccn1)N1CCN(c2ncnc3c2nc(-c2ccccc2Cl)n3-c2ccc(Cl)cc2)CC1] | C27H22Cl2N8O | 4-[8-(2-Chlorophenyl)-9-(4-chlorophenyl)-9H-purin-6-yl]-N-(pyridin-2-yl)piperazine-1-carboxamide |
| 123 | 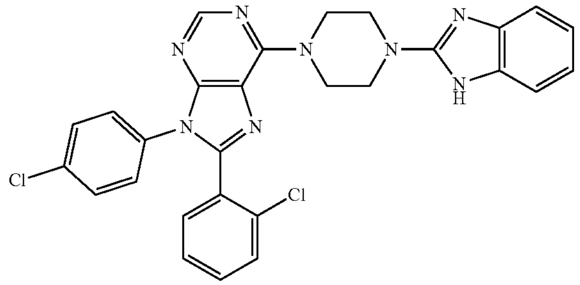 [SMILES: Clc1ccc(-n2c(-c3ccccc3Cl)nc3c(N4CCN(c5nc6ccccc6[nH]5)CC4)ncnc32)cc1] | C28H22Cl2N8 | 6-[4-(1H-benzimidazol-2-yl)piperazin-1-yl]-8-(2-chlorophenyl)-9-(4-chlorophenyl)-9H-purine |
| 124 | 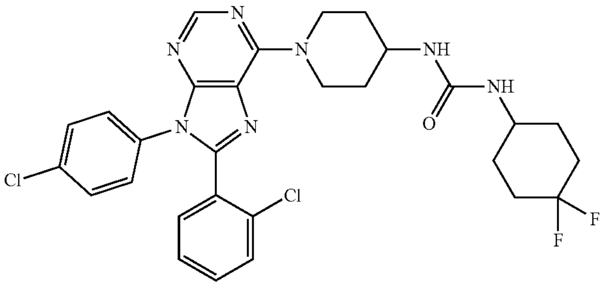 [SMILES: O=C(NC1CCN(c2ncnc3c2nc(-c2ccccc2Cl)n3-c2ccc(Cl)cc2)CC1)NC1CCC(F)(F)CC1] | C29H29Cl2F2N7O | 3-{1-[8-(2-Chloro-phenyl)-9-(4-chloro-phenyl)-9H-purin-6-yl]piperidin-4-yl}-1-(4,4-difluorocyclo-hexyl)urea |
| 125 | 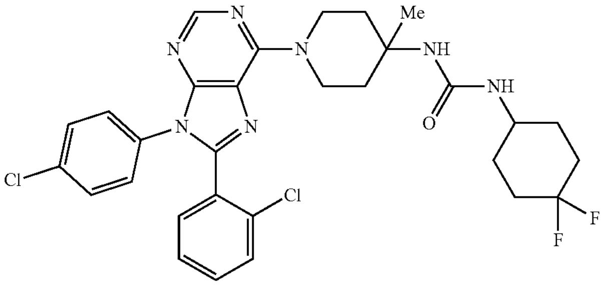 [SMILES: CC1(NC(=O)NC2CCC(F)(F)CC2)CCN(c2ncnc3c2nc(-c2ccccc2Cl)n3-c2ccc(Cl)cc2)CC1] | C30H31Cl2F2N7O | 3-{1-[8-(2-Chloro-phenyl)-9-(4-chloro-phenyl)-9H-purin-6-yl]-4-methylpiperidin-4-yl}-1-(4,4-difluoro-cyclohexyl)urea |
| 126 | 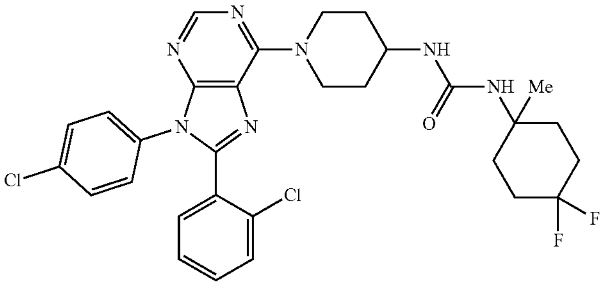 [SMILES: CC1(NC(=O)NC2CCN(c3ncnc4c3nc(-c3ccccc3Cl)n4-c3ccc(Cl)cc3)CC2)CCC(F)(F)CC1] | C30H31Cl2F2N7O | 3-{1-[8-(2-Chloro-phenyl)-9-(4-chloro-phenyl)-9H-purin-6-yl]piperidin-4-yl}-1-(4,4-difluoro-1-methyl-cyclohexyl)urea |

TABLE 2-continued

| Structures of CB1 Receptor Antagonists | | | |
|---|---|---|---|
| Cmd # | Structure | MF | Name |
| 127 | 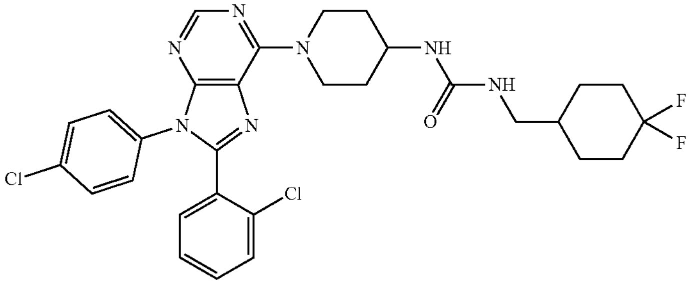 [SMILES: O=C(NCC1CCC(F)(F)CC1)NC1CCN(c2ncnc3c2nc(-c2ccccc2Cl)n3-c2ccc(Cl)cc2)CC1] | C30H31Cl2F2N7O | 3-{1-[8-(2-Chloro-phenyl)-9-(4-chloro-phenyl)-9H-purin-6-yl]piperidin-4-yl}-1-[(4,4-difluorocyclo-hexyl)methyl]urea |
| 128 | 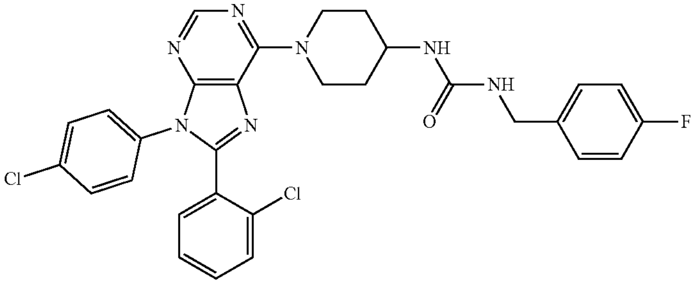 [SMILES: O=C(NCc1ccc(F)cc1)NC1CCN(c2ncnc3c2nc(-c2ccccc2Cl)n3-c2ccc(Cl)cc2)CC1] | C30H26Cl2FN7O | 3-{1-[8-(2-Chloro-phenyl)-9-(4-chloro-phenyl)-9H-purin-6-yl]piperidin-4-yl}-1-[(4-fluorophenyl)-methyl]urea |
| 129 | 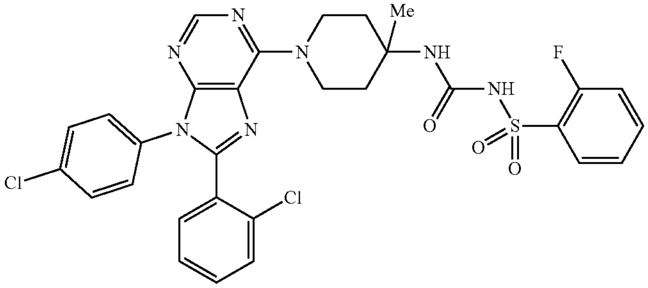 [SMILES: CC1(NC(=O)NS(=O)(=O)c2ccccc2F)CCN(c2ncnc3c2nc(-c2ccccc2Cl)n3-c2ccc(Cl)cc2)CC1] | C30H26Cl2FN7O3S | 3-{1-[8-(2-Chloro-phenyl)-9-(4-chloro-phenyl)-9H-purin-6-yl]-4-methylpiperidin-4-yl}-1-[(2-fluoro-benzene)sulfonyl]urea |

6.2. Example 2. Cell Culture and In Vivo Characterization

All compounds were characterized by $H^1$ NMR and evaluated using a calcium mobilization assay. Each compound was pharmacologically characterized using a functional fluorescent CB1 activated Gαq16-coupled intracellular calcium mobilization assay in CHO-K1 cells as has been previously described and apparent affinity (Ke) values were determined. See Zhang et al., *J. Med. Chem.* 2010, 53, 7048, which is incorporated herein by reference. Further characterization of select compounds was performed using radioligand displacement of [3H]1 and equilibrium dissociation constant (Ki) values were determined. Selectivity of these compounds at CB1 versus CB2 was also determined by obtaining Ki values at either receptor using displacement of [3H]CP55940 in membranes of CHO-K1 cells over-expressing either receptor. Data reported are average values from 3-6 measurements.

Select compounds were chosen for study in radioligand displacement assays using radiolabeled rimonobant, SR141716 ([$^3$H]1). Several of these compounds demonstrated good Ki values in the low nM range, with the thiomorpholine 1,1-dioxide-containing compound having a Ki of 16.8 nM. Selectivity against the CB2 receptor was determined by comparing the compound displacement of radiolabeled CP55940, which is a cannabinoid known to act as a full agonist at both CB1 and CB2 receptors. In general, tested compounds were selective for CB1 over CB2.

TABLE 3

| In Vitro Activity of Compounds | | | | |
|---|---|---|---|---|
| Cmp # | Apparent antagonist dissociation constant (Ke) at hCB1 (nM) | Binding affinity (Ki) at hCB1 (nM)* | Binding affinity (Ki) at hCB2 (nM)* | CB2 Ki/ CB1 Ki selectivity ratio |
| 1 | 0.1 | 0.4 | 8500 | 2100 |
| 3 | 11.3 | 4.8 | 484 | 101 |
| 4 | 1.1 | 3 | 20000 | 67000 |
| 5 | 2 | 2 | 53000 | 26000 |
| 6 | 3.1 | 2.1 | 3933 | 1918 |
| 12 | 140 | | | |
| 17 | 77 | | | |
| 18 | 30 | 7 | >5000 | >710 |
| 19 | 52 | 4 | 17000 | 4200 |
| 20 | 250 | | | |
| 21 | 240 | | | |
| 22 | 4 | 23 | >40000 | >1600 |
| 23 | 45 | 22 | 8200 | 370 |
| 24 | 37 | 28 | >7000 | >250 |
| 25 | 25 | 22 | 39000 | 7600 |
| 26 | 44 | 520 | >6000 | >11 |

TABLE 3-continued

In Vitro Activity of Compounds

| Cmp # | Apparent antagonist dissociation constant (Ke) at hCB1 (nM) | Binding affinity (Ki) at hCB1 (nM)* | Binding affinity (Ki) at hCB2 (nM)* | CB2 Ki/ CB1 Ki selectivity ratio |
|---|---|---|---|---|
| 27 | 600 | | | |
| 28 | 20 | 3 | 11000 | 3700 |
| 29 | 21 | 4 | 10000 | 2500 |
| 30 | 12 | 47 | | |
| 31 | 1.4 | 6 | 19000 | 32000 |
| 32 | 54 | 2 | 4600 | 2300 |
| 36 | 100 | | | |
| 37 | 59 | | | |
| 38 | 360 | | | |
| 39 | 106 | 42 | 4100 | 98 |
| 40 | 82 | | | |
| 41 | 185 | | | |
| 42 | 5 | 5 | 4200 | 840 |
| 43 | 2 | 19 | 2000 | 110 |
| 44 | 13 | 4 | 74000 | 18000 |
| 45 | 8 | 39 | 790 | 30 |
| 46 | 27 | 7 | 240 | 34 |
| 47 | 140 | | | |
| 48 | 440 | | | |
| 49 | 320 | | | |
| 50 | 150 | | | |
| 51 | 380 | | | |
| 52 | 220 | | | |
| 53 | 110 | | | |
| 55 | 869 | 272 | 1568 | 5.8 |
| 56 | 2 | 6 | 1300 | 220 |
| 57 | 10 | 9 | 3200 | 360 |
| 58 | 3.5 | 5.0 | 3353 | 671 |
| 61 | 6.1 | 5.3 | 606 | 115 |
| 62 | 3.6 | 2.2 | inactive | |
| 65 | 11.6 | 4.7 | inactive | |
| 66 | 17.0 | 1.8 | 112 | 64.1 |
| 67 | 13.0 | 2.4 | 2712 | 1136 |
| 69 | 3.8 | 1.1 | 1278 | 1126 |
| 70 | 11.1 | 2.5 | 2138 | 844 |
| 72 | 16.4 | 2.6 | inactive | |
| 74 | 6.7 | 2.4 | inactive | |
| 75 | 21 | 3 | 20000 | 6700 |
| 76 | 5.2 | 2.2 | inactive | |
| 77 | 3.3 | 1.3 | inactive | |
| 78 | 17.0 | 2.7 | 980 | 366 |
| 79 | 2.4 | 1.2 | 848 | 728 |
| 80 | 1.5 | 1.4 | 978 | 699 |
| 81 | 0.4 | 0.6 | 505 | 871 |
| 82 | 0.2 | 2.0 | 2842 | 1407 |
| 84 | 17.0 | 5.3 | 2297 | 434 |
| 86 | 3.4 | 24.4 | 1653 | 68 |
| 87 | 0.4 | 1.0 | 134 | 141 |
| 90 | 42.2 | 12.1 | 620 | 51 |
| 91 | 27.8 | 9.2 | 1154 | 126 |
| 93 | 18.5 | 17.9 | 830 | 46 |
| 96 | 0.9 | 6.8 | 2262 | 335 |
| 97 | 1.5 | 3.6 | inactive | |
| 98 | 13.6 | 8.3 | 775 | 93 |
| 99 | 6.5 | 0.9 | 54 | 59 |
| 100 | 5.8 | 4.5 | 1253 | 282 |
| 101 | 5.1 | 8.2 | inactive | |
| 102 | 14.6 | 12.2 | inactive | |
| 103 | 0.6 | 5.5 | 403 | 75 |
| 105 | 6.0 | 22.4 | 1718 | 77 |
| 106 | 0.5 | 11.9 | 1131 | 95 |
| 111 | 5 | 5 | >50000 | >10000 |
| 112 | 4 | 2 | 76000 | 38000 |
| 113 | 3 | 3 | 38000 | 13000 |
| 114 | 42 | 8 | 990 | 120 |
| 115 | 12 | 24 | 3600 | 150 |
| 116 | 510 | 470 | >6000 | >12 |
| 117 | 54 | 5 | 740 | 150 |
| 118 | 17 | 24 | 1300 | 54 |
| 119 | 41 | 1.4 | 620 | 440 |
| 120 | 35 | 43 | 740 | 17 |
| 121 | 3 | 6 | 2400 | 400 |
| 122 | 8 | 6 | 7100 | 1200 |
| 123 | 53 | | | |
| 124 | 79 | 18 | >10000 | >500 |
| 128 | 51 | 3 | >5000 | >1600 |
| 129 | 7 | 120 | >10000 | >80 |

TABLE 4

MDCK BBB Assay (Basolateral/Apical Peak Area Ratio)

| Compound # | MDCK BBB Assay (Basolateral/Apical Peak Area Ratio) Mean | % Permeable |
|---|---|---|
| 3 | 0.005 | 1% |
| 4 | 0.0006 | 0% |
| 5 | 0.0008 | 0% |
| 6 | 0.025 | 2% |
| 7 | 0 | 0% |
| 18 | 0.0023 | 0% |
| 19 | 0.001 | 0% |
| 22 | 0.0004 | 0% |
| 23 | 0.013 | 1% |
| 25 | 0 | 0% |
| 26 | 0.0019 | 0% |
| 31 | 0 | 0% |
| 32 | 0.001 | 0% |
| 42 | 0.0001 | 0% |
| 58 | 0.028 | 3% |
| 61 | 0.000 | 0% |
| 62 | 0.000 | 0% |
| 65 | 0.082 | 8% |
| 66 | 0.025 | 2% |
| 67 | 0.001 | 0% |
| 69 | 0.000 | 0% |
| 70 | 0.000 | 0% |
| 72 | 0.001 | 0% |
| 74 | 0.000 | 0% |
| 76 | 0.000 | 0% |
| 77 | 3.518 | ~100% |
| 78 | 0.181 | 18% |
| 79 | 0.061 | 6% |
| 80 | 0.000 | 0% |
| 81 | 0.053 | 5% |
| 82 | 0.000 | 0% |
| 84 | 0.038 | 4% |
| 86 | 0.143 | 14% |
| 87 | 4.660 | ~100% |
| 90 | 0.379 | 38% |
| 91 | 0.409 | 41% |
| 93 | 0.000 | 0% |
| 96 | 0.018 | 2% |
| 97 | 0.000 | 0% |
| 98 | 0.000 | 0% |
| 99 | 0.000 | 0% |
| 101 | 0.000 | 0% |
| 103 | 0.000 | 0% |
| 105 | 0.040 | 4% |
| 106 | 0.036 | 4% |
| 117 | 0.03 | 3% |
| 122 | 0.012 | 1% |

6.2.1. Pharmacokinetic Properties of Selected CB1 Receptor Antagonists

Select compounds were chosen for in vivo studies to determine penetration into the CNS. Compounds were cassette dosed orally at 2.5 mg/kg in mice. Brain and plasma samples were collected at 1, 2, 4, and 24 hours post dose and samples were analyzed by LC/MS/MS (Table 5, below). Unperfused brains were used which contain a blood volume of approximately 4%.

TABLE 5

Brain Penetration Data for Select Compounds

| Cmpd # | Maximum Plasma (ng/ml) | Maximum Brain (ng/g) | Brain:Plasma Ratio (%) |
|---|---|---|---|
| 19 | 4200 | 140 | 3% |
| 26 | 50 | 8.0 | 16% |
| 44 | 500 | 90 | 18% |
| 98 | 114 | 6.8 | 6% |
| 99 | 65 | 5.8 | 9% |
| 124 | 2900 | 46 | 1.6% |
| 129 | 14400 | 180 | 1.3% |

6.2.2. Effect of 98 on Alcohol Induced Liver Steatosis

Past studies had indicated that paracrine activation of CB1 on liver hepatocytes by 2-arachidonoylglycerol (2-AG), secreted by hepatic stellate cells (HSC) during alcoholic liver injury, promoted hepatic lipid accumulation (alcoholic steatosis, AS). The prototypical CB1 antagonist rimonabant was effective in reducing AS by blocking transcription of lipogenic genes activated by SREB-1C. Compound 98 was shown to block disease progression/development in a mouse model of AS.

Pathogen-free female C57BL/6J mice, aged 9 weeks (Jackson Laboratories, Bar Harbor, Me., USA) weighing 19-21 g were used in this study. C57BL/6 mice were offered solid PicoLab Certified Rodent LabDiet® 5053 (pellet) ad libitum during the acclimation period following which, all animals were switched to a Lieber-DeCarli 82' Control (Catalog No: F1259SP, BioServ®) diet which was nutritionally complete. Control and ethanol (Catalog No: F1258SP, BioServ®) liquid diets were prepared daily as per instructions provided by manufacturer. Once on the liquid diet for 3 days, ethanol was introduced progressively from 1% to 5% (vol/vol) over 15 days to scheduled animals. The animals were maintained on liquid diet for 4 additional weeks after reaching the final concentration of ethanol and administered the test article for the last two weeks to evaluate its efficacy in limiting/reversing alcoholic steatosis (AS). Compound 98 was formulated as a suspension in 0.5% sodium carboxymethylcellulose with 1% N-Methyl-2-pyrrolidone (NMP) and 0.3% Tween 80 and administered to mice twice daily by oral gavage at a concentration of 1.25 mg/kg based on data from PK experiments and preliminary studies. Control animals were administered the vehicle alone. Pairwise-feeding within groups was conducted to adjust for caloric intake between groups. Following the final day of liquid diet/oral dosing administration, animals were euthanized and necropsied to collect tissue samples. Blood was collected from all animals at the time of scheduled necropsy via cardiac puncture into SAI Infusion Technologies™ collection microtubes with lithium heparin as the anticoagulant and centrifuged at approximately 2,800×g for approximately 10 minutes at 4° C. to obtain plasma within 1 hr of collection. The liver was removed and weighed following which a section of the median lobe of the liver was embedded in optimal cutting temperature solution (OCT, Tissue-Plus®) and preserved in a base mold (24×24×5 mm, Fisherbrand™) for sectioning to examine degree of steatosis and monitor degree of liver damage and general cytotoxicity. For histopathology studies, Oil Red O (ORO) staining was performed on harvested liver tissue to assess the degree of liver steatosis in the ethanol and control diet fed mouse groups. OCT embedded liver sections were stained with ORO and examined under a light microscope. Digitized images of mouse liver sections (10 μm in thickness) were assessed semi-quantitatively for degree of steatosis using Image J software (NIH, Bethesda, Md.). Briefly, a 5 $in^2$ digital grid (Image J Command Menu: Plugin-Analyze-Grid) was placed on each image wherein lipid droplets in 6 grids per image were counted and the average number of oil droplets was recorded for each animal (n=6, per group). Results have been reported as means±SD. Statistical significance was determined through ANOVA between treatment and control groups using Graph Pad Prism 7.0 (GraphPad Software Inc., La Jolla, Calif., USA) at a confidence level of *$p<0.001$.

FIG. 1A-1B shows representative photomicrographs depicting lipid accumulation in liver slices of mice from various treatment groups. Lipid accumulation in livers from animals on the control diet (no ethanol) were minimal, as revealed through Oil Red O (ORO) staining (left panel in FIG. 1A). In contrast, the ethanol containing diet caused significant accumulation of lipid droplets (center panel in FIG. 1A). Liver histology and ORO staining analyses showed obvious microsteatosis and macrosteatosis in the livers from all ethanol diet-fed mice compared to control diet-fed mice, in the absence of drug treatment. Using ethanol diet-fed mice, administration of compound 98 at a dose of 1.25 mg/kg twice daily by oral gavage significantly reduced hepatic lipid accumulation (right panel in FIG. 1A) compared to the vehicle control group (center panel in FIG. 1A). The data are quantified in FIG. 1B.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. A compound represented by the Formula III:

III

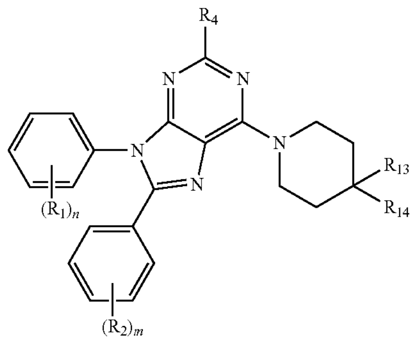

or a pharmaceutically acceptable salt thereof, wherein each $R_1$ and $R_2$ is independently $C_{1-8}$ alkoxy, $C_{1-8}$ alkyl, $C_{3-8}$ cycloalkyl, $C_{3-6}$ heterocycle, —$CONR_5R_6$, —$COR_7$, cyano, H, halo, —$NR_5R_6$, —$NR_8COR_7$, —$NR_8CONR_5R_6$, —$NR_8SO_2R_7$, —$NR_8SO_2NR_5R_6$, —$SO_2NR_5R_6$ or —$SO_2R_7$;

$R_4$ is $C_{1-8}$ alkoxy, $C_{1-8}$ alkyl, $C_{3-8}$ cycloalkyl, or H;

$R_{13}$ is —C(═$NR_9$)$R_{12}$, —C(═$NR_9$)$NR_{10}R_{11}$, heteroaryl, $NHR_{15}$ or $NR_{15}R_{19}$;

$R_{14}$ is aryl, $C_{1-8}$ alkyl, $C_{3-8}$ cycloalkyl, $C_{3-6}$ heterocycle, heteroaryl or H; or $R_{13}$ and $R_{14}$ together make a 3-8 member ring;

$R_{15}$ is $C_{1-8}$ alkyl(heteroaryl), $C_{1-8}$ alkyl(heterocycle), —C(═$NR_9$)$NR_{10}R_{11}$, —C(═$NR_9$)$R_{12}$, $CONR_{16}R_{11}$, —CON($R_{11}$)$SO_2R_{12}$, heteroaryl, heterocycle, or —$SO_2NR_{16}R_{11}$;

each $R_5$, $R_6$, $R_8$ $R_{10}$, $R_{11}$, and $R_{19}$ is independently aryl, $C_{1-8}$ alkyl, $C_{1-8}$ alkyl(aryl), $C_{1-8}$ alkyl(heteroaryl), $C_{1-8}$ alkyl(heterocycle), $C_{1-8}$ alkyl($C_{3-8}$ cycloalkyl), $C_{3-8}$ cycloalkyl, H, heteroaryl or heterocycle; or $R_5$ and $R_6$ together make a 3-8 member ring which may be substituted with one or more heteroatoms; or $R_5$ and $R_8$ together make a 4-8 member ring which may be substituted with one or more heteroatoms; or $R_{10}$ and $R_{11}$ together make a 3-8 member ring which may be substituted with one or more heteroatoms; or $R_{11}$ and $R_{16}$ together make a 3-8 member ring which may be substituted with one or more heteroatoms;

each $R_7$ and $R_{12}$ is independently aryl, $C_{1-8}$ alkyl, $C_{1-8}$ alkyl(aryl), $C_{1-8}$ alkyl(heteroaryl), $C_{1-8}$ alkyl(heterocycle), $C_{1-8}$ alkyl($C_{3-8}$cycloalkyl), $C_{3-8}$ cycloalkyl, heteroaryl or heterocycle; or $R_7$ and $R_8$ together make a 4-8 member ring which may be substituted with one or more heteroatoms; or $R_{11}$ and $R_{12}$ together make a 4-8 member ring which may be substituted with one or more heteroatoms;

$R_9$ is $C_{1-8}$ alkoxy, $C_{1-8}$ alkyl, $C_{3-8}$ cycloalkyl, cyano, H, or hydroxyl;

$R_{16}$ and $R_{18}$ is independently aryl, $C_{1-8}$ alkyl(aryl), $C_{1-8}$ alkyl(heteroaryl), $C_{1-8}$ alkyl(heterocycle), heteroaryl or heterocycle;

$R_{17}$ is $C_{1-8}$ alkyl(heteroaryl), $C_{1-8}$ alkyl(heterocycle), heteroaryl or heterocycle; and wherein n and m are independently integers from 0 to 5.

2. The compound of claim 1, wherein $R_4$ is H.

3. The compound of claim 1, wherein $R_1$ is at the meta and/or para positions.

4. The compound of claim 1, wherein at least one $R_2$ is in the ortho position.

5. The compound of claim 1, wherein $R_1$ is F, Cl, $CF_3$, CN, $OCF_3$ or $OCHF_2$.

6. The compound of claim 1, wherein $R_2$ is F, Cl, $CF_3$ or Me.

7. The compound of claim 1, wherein $R_{13}$ is $NHR_{15}$ or $NR_{15}R_{19}$.

8. The compound of claim 1, wherein $R_{15}$ is —$CONR_{16}R_{11}$.

9. The compound of claim 1, wherein $R_{15}$ is —C(═$NR_9$)$NR_{10}R_{11}$ or —C(═$NR_9$)$R_{12}$.

10. The compound of claim 1, wherein $R_{10}$ is aryl, heteroaryl, $C_{1-8}$ alkyl, $C_{3-8}$ cycloalkyl, or $C_{1-6}$ alkyl($C_{3-8}$ cycloalkyl).

11. The compound of claim 1, wherein $R_{11}$ is H.

12. The compound of claim 1, wherein $R_{14}$ is H.

13. The compound of claim 1, wherein $R_{16}$ is aryl, $C_{1-8}$ alkyl(aryl), $C_{1-8}$ alkyl(heteroaryl) or heteroaryl.

14. The compound of claim 1, wherein n and m are independently 1 or 2.

15. A pharmaceutical composition, comprising a compound of claim 1 and one or more pharmaceutically acceptable carriers.

16. A method for treating or delaying the progression of disorders associated with fatty livers a subject in need thereof that are alleviated by antagonizing the CB1 receptor, the method comprising administering to the subject a therapeutically effective amount of the compound of claim 1 so as to treat or delay the progression of the disorder involving fatty livers in the subject.

17. The method of claim 16, wherein the disorder is diabetes, dyslipidemia, or obesity.

18. The method of claim 17, wherein the disorder is fatty liver disease.

19. The method of claim 18, wherein the fatty liver disease is alcoholic steatosis or nonalcoholic steatohepatitis (NASH).

20. The method of claim 16, wherein the compound is formulated or co-administered with a second agent wherein the second agent is an anti-depressant, a blood pressure lowering agent, or a lipid lowering agent.

* * * * *

UNITED STATES PATENT AND TRADEMARK OFFICE

CERTIFICATE OF CORRECTION

PATENT NO. : 10,696,677 B2
APPLICATION NO. : 16/472155
DATED : June 30, 2020
INVENTOR(S) : Rangan Maitra et al.

It is certified that error appears in the above-identified patent and that said Letters Patent is hereby corrected as shown below:

In the Specification

Please replace the paragraph in Column 1, Lines 7-11 below CROSS REFERENCE TO RELATED APPLICATIONS:
--This application is a §371 U.S. National Stage of International Application PCT/US2017/067602, filed December 20, 2017 having Atty. Docket No. 121-58-PCT, which claims the benefit of US Provisional Appn. 62/437,280 filed December 21, 2016, Maitra et al., entitled "DIARYL PURINE DERIVATIVES WITH IMPROVED BIOAVAILABILITY", Atty. Dkt. No. 121-58-PROV3 which are hereby incorporated by reference in their entireties.--

Please replace the paragraph on Column 1, Lines 16-22 below STATEMENT REGARDING FEDERALLY SPONSORED RESEARCH OR DEVELOPMENT:
--This invention was made with government support under Grant Nos. AA022235 and DK100414 awarded by the National Institutes of Health. The United States Government has certain rights in the invention.--

Signed and Sealed this
Fifteenth Day of August, 2023

Katherine Kelly Vidal

Katherine Kelly Vidal
*Director of the United States Patent and Trademark Office*